(12) United States Patent
Järver et al.

(10) Patent No.: US 11,345,916 B2
(45) Date of Patent: May 31, 2022

(54) SINGLE STRANDED OLIGONUCLEOTIDES INHIBITING ENDOCYTOSIS

(71) Applicant: TIRMED PHARMA AB, Bromma (SE)

(72) Inventors: Peter Järver, Stockholm (SE); Anna-Lena Marie Spetz, Bromma (SE); Aleksandra Maria Dondalska, Solna (SE)

(73) Assignee: TIRMED PHARMA AB, Bromma (SE)

( * ) Notice: Subject to any disclaimer, the term of this patent is extended or adjusted under 35 U.S.C. 154(b) by 6 days.

(21) Appl. No.: 16/644,151

(22) PCT Filed: Sep. 6, 2018

(86) PCT No.: PCT/EP2018/074032
§ 371 (c)(1),
(2) Date: Mar. 3, 2020

(87) PCT Pub. No.: WO2019/048555
PCT Pub. Date: Mar. 14, 2019

(65) Prior Publication Data
US 2021/0062194 A1 Mar. 4, 2021

(30) Foreign Application Priority Data
Sep. 6, 2017 (GB) .................................... 1714330

(51) Int. Cl.
*C12N 15/113* (2010.01)
*A61P 31/16* (2006.01)

(52) U.S. Cl.
CPC .......... *C12N 15/1131* (2013.01); *A61P 31/16* (2018.01); *C12N 15/1138* (2013.01); *C12N 2310/315* (2013.01); *C12N 2310/321* (2013.01); *C12N 2310/322* (2013.01)

(58) Field of Classification Search
CPC ............ C12N 15/1131; C12N 15/1138; C12N 2310/315; C12N 2310/321; C12N 2310/322; C12N 15/113; A61P 31/16
See application file for complete search history.

(56) References Cited

U.S. PATENT DOCUMENTS

| 2004/0219677 A1 | 11/2004 | Drocourt et al. |
| 2012/0184601 A1 | 7/2012 | Vaillant et al. |
| 2016/0275240 A1 | 9/2016 | Huelga et al. |

FOREIGN PATENT DOCUMENTS

| WO | WO 01/47944 A2 | 7/2001 |
| WO | WO 01/47944 A3 | 7/2001 |
| WO | WO 01/51670 A2 | 7/2001 |
| WO | WO 01/51670 A3 | 7/2001 |
| WO | WO 2016/164916 A1 | 10/2016 |
| WO | WO 2016/202779 A1 | 12/2016 |
| WO | WO 2017/140815 A1 | 8/2017 |

OTHER PUBLICATIONS

Jarver et al., "Single-Stranded Nucleic Acids Regulate TLR3/4/7 Activation through Interference with Clathrin-Mediated Endocytosis", Scientific Reports, 2018, 8(1): 15841.
Skold et al., "Single-stranded DNA oligonucleotides inbibit TLR3-mediated responses in human monocyte-derived dendritic cells and in vivo in cynomolgus macaques", Blood, 2012, 120(4): 768-777.
Poux et al., "A Single-Stranded Oligonucleotide Inhibits Toll-Like Receptor 3 Activation and Reduces Influenza A (H1N1) Infection", Front. Immunol., Sep. 2019, 10:2161.

*Primary Examiner* — J. E. Angell

(74) *Attorney, Agent, or Firm* — James S. Keddie; Bozicevic, Field & Francis LLP

(57) ABSTRACT

The invention provides a single-stranded oligonucleotide (ssON) for use in preventing or treating an influenza virus infection in a subject, wherein the single-stranded oligonucleotide is one that inhibits endocytosis. The invention also provides a single-stranded oligonucleotide (ssON) that comprises or consists of a polynucleotide having a sequence sharing at least 60% sequence identity with a sequence of any one of SEQ ID NOs: 13-21 listed in Table 1, or a complementary sequence thereof.

19 Claims, 25 Drawing Sheets

Figure 1:
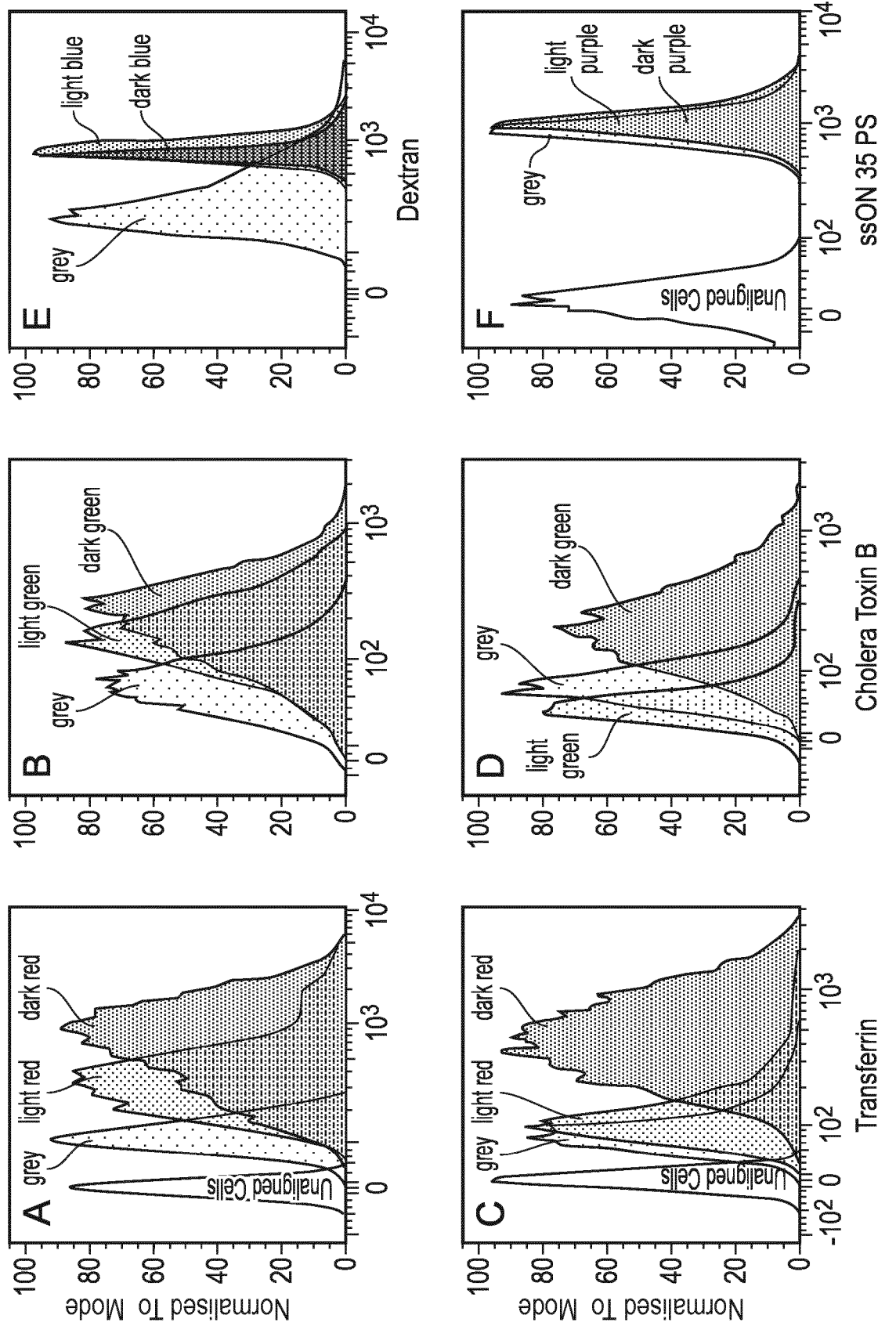
Figure 1:
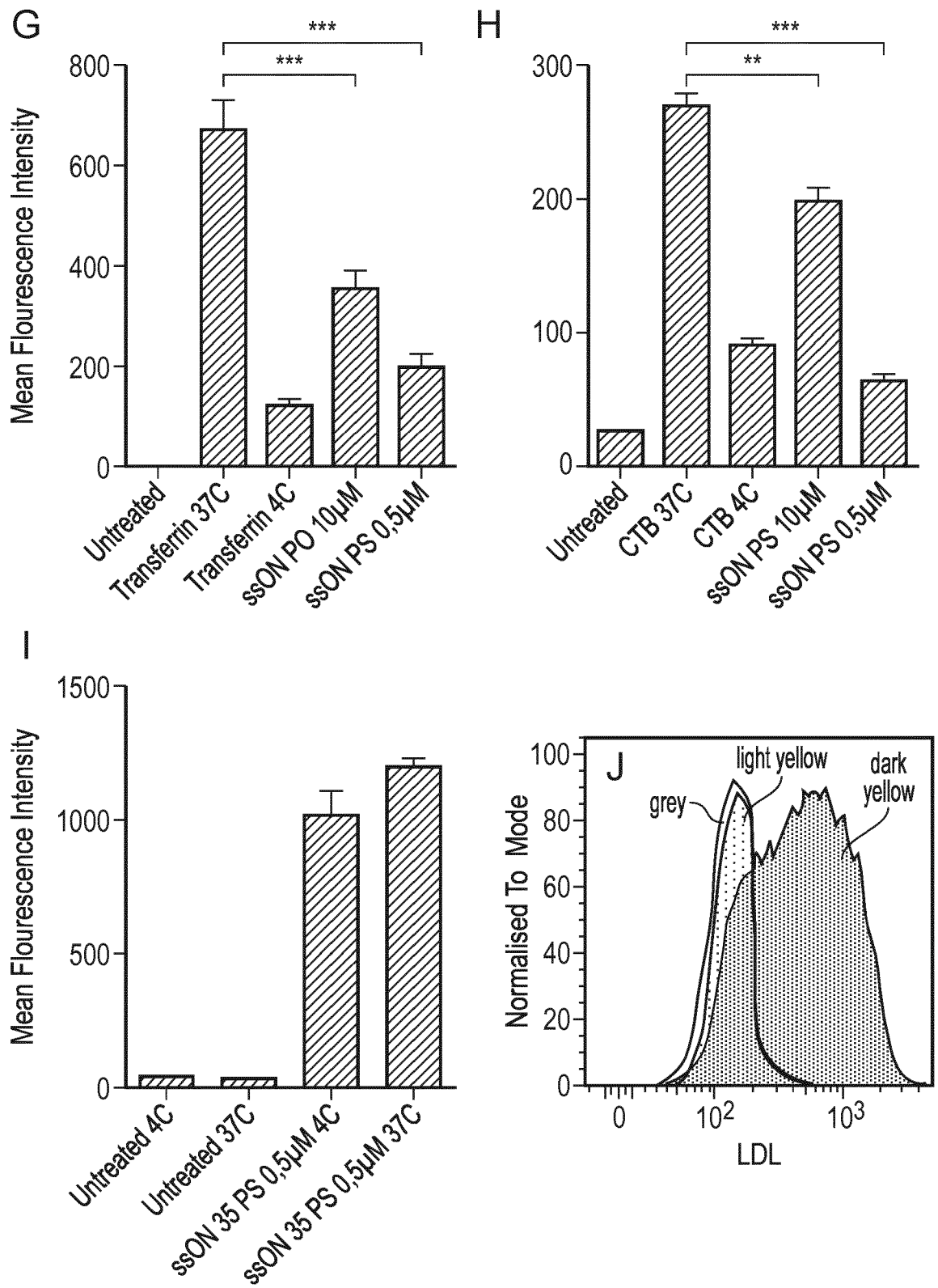

Specification includes a Sequence Listing.

SINGLE STRANDED OLIGONUCLEOTIDES INHIBITING ENDOCYTOSIS

CROSS-REFERENCE TO RELATED APPLICATIONS

This application is a § 371 national phase of International Application No. PCT/EP2018/074032, filed on Sep. 6, 2018, which claims the benefit of United Kingdom Patent Application No. 1714330.6, filed on Sep. 6, 2017, which applications are incorporated by reference herein.

The present invention relates to oligonucleotides, and in particular to oligonucleotides that are useful in preventing or treating influenza infection and disorders of the skin and/or subcutaneous tissue.

Influenza virus (IV) is an enveloped virus with a single-stranded negative sense RNA genome. It is a highly contagious with frequent global outbreaks. The virus belongs to the Orthomyxovirus family and is classified in three antigen types: A, B and C (van de Wakker et al, Eur J Pharmacol, 809:178-190). Only IV A and B subtypes cause large outbreaks and serious illness.

Seasonal IV flu affects up to ~20% of the world population and leads to an excess of 250,000-500,000 deaths each year (van de Wakker et al, Eur J Pharmacol, 809:178-190). The virus proteins constantly mutate due to the unreliability of RNA-polymerases. Because of genetic drift and genetic shift, new IV viruses arise continuously, making previously acquired immunity no longer opportune, and antiviral drugs potentially less effective. Due to the high mutation rate of IV, the efficacy of existing vaccines are variable and annual development of new vaccines is required.

Currently, there are two classes of anti-IV drugs approved by the FDA for clinical use: the M2 protein inhibitors amantadine and rimantadine, and the neuraminidase inhibitors oseltamivir and zanamivir. More and more resistant strains arise against these drugs and their use is often associated with adverse side effects. Therefore, there is an urgent need for development of alternative anti-IV agents with new mechanisms of action to combat IV.

Oligonucleotides are short DNA or RNA molecules or oligomers that have a wide range of applications.

"CpG oligonucleotides" (or CpG-ssON) are short single-stranded synthetic DNA or RNA molecules that contain a cytosine triphosphate nucleotide ("C") followed by a guanine triphosphate nucleotide ("G"). Unmethylated CpG-containing nucleic acids stimulate the immune system and can be used to treat infectious diseases, allergy, asthma and other disorders (Scheiermann, J., and Klinman, D. M. 2014. Vaccine 32:6377-6389; Aryan, Z. and Rezaei, N. 2015. Curr Opin Allergy Clin Immunol. 15:568-74.

CpG sequences in ssDNA-ODN ligands have been shown to be indispensable for activation of Toll-like receptor 9 (TLR9), which plays a fundamental role in pathogen recognition and activation of innate immunity. The stimulatory effect of the ligand is lost when the CpG repeats are removed. The TLR9-mediated immunostimulatory effect has not been shown in single-stranded oligonucleotides lacking CpG motifs ("non-CpG ssON").

Single-stranded DNA oligonucleotides (ssONs) inhibit TLR3-mediated responses in human monocyte-derived dendritic cells and in vivo in cynomolgus macaques (Sköld et al. 2012. Blood 120:768-777). TLR3 is a key receptor for recognition of double-stranded RNA and initiation of immune responses against viral infections. It was shown by Sköld et al. that human monocyte-derived dendritic cells up-regulate maturation markers and secrete proinflammatory cytokines on treatment with the synthetic TLR3 ligand polyinosine-polycytidylic acid (Poly(I:C)). Poly(I:C) is a synthetic agonist to TLR3 and is often used as an adjuvant in vaccines (see e.g. Duthie, M. S. et al. 2011. Immunol. Rev. 239(1):178-196). Sköld et al reported that TLR3-mediated events were inhibited in cultures with ssON, as was Poly(I:C) activation of non-hematopoietic cell. The uptake of Poly(I:C) into cells was reduced in the presence of ssON, preventing TLR3 engagement from occurring. In cynomolgus macaques, the levels of proinflammatory cytokines in nasal secretions were reduced when ssONs were administered via the intranasal route. According to Sköld et al., therefore, treatment with ssONs could lead to significant changes in cytokine levels in mammals.

The ssON sequences used by Sköld et al. were:

5'-GTCGTTTTGTCGTTTTGTCGTTGTTGGTGGTGGTG-3'

(CpG ssON; SEQ ID NO: 25);
and

5'-GAAGTTTTGAGGTTTTGAAGTTGTTGGTGGTGGTG-3'

(non-CpG ssON; SEQ ID NO: 1).

The present inventors have shown (WO 2016/202779) that non-CpG ssONs, such as the one shown as SEQ ID NO: 1, are useful in the treatment or prophylaxis of disorders of the skin and/or subcutaneous tissue, including pruritus. Transcriptional profiling of skin biopsies revealed ssON-dependent selective dampening of dsRNA(Poly(I:C))-induced pro-inflammatory responses in macaques. The ssON-modulated cytokine pattern was confirmed by protein analyses directly ex vivo from skin biopsies and revealed induction of IL-10 and inhibition of IL-6 secretion. This is further evidence that ssONs can produce significant differences in cytokine production when administered to a mammal.

Baharom, F. et al. (J. Immunol. 194:4422-4430) reported that lipopolysaccharide or Poly(I:C) stimulation of monocyte-derived dendritic cells results in type I IFN induction and reduced susceptibility to influenza A virus infection. Such results imply that ssONs that are capable of reducing Poly(I:C)-stimulated effects would increase susceptibility to virus infection, such as influenza infections.

Synthetic oligodeoxynucleotides that can down-regulate cellular elements of the immune system have been developed and studied in preclinical models. These agents vary in sequence, mechanism of action, and cellular target(s) but there is often a lack of understanding on their mechanism of action (Bayik, D. et al. 2016. Pharmacol Res. 105:216-225). For example, it has been shown (Gursel, I. et al. 2003. J Immunol. 171(3):1393-1400) that repetitive elements, such as TTAGGG, present at high frequency in mammalian telomeres, down-regulate CpG-induced immune activation.

Hanecak et al. (US 2011/0124715) discloses chemically modified oligonucleotides that are useful for inhibiting virus activity. The modified oligonucleotides have no more than 27 nucleic acid base units and comprise at least one GGGG sequence or at least two GGG sequences.

Vaillant et al. (US 2012/0184601) discloses random sequence oligonucleotides that have antiviral activity. It was disclosed that a group of viruses, limited to HSV-1, HSV-2, CMV, Coxsackie virus B2, DHBV, Hantavirus, parainfluenza virus, HIV-1, and vaccinia virus, can be inhibited by ssONs in vitro. It was suggested that the random ssONs had a broad-spectrum antiviral activity with viruses where assembly and/or packaging and/or encapsidation of the viral genome was a required step in the replication. However, the authors also stated that while they could inhibit RSV by using ssONs, they failed to inhibit viruses such as Influenza A (H3N2), Corona virus (HCoV-OC43), BVDV, rhinovirus (HGP) and adenovirus (Human Ad5). Further ssONs are described in WO 2006/042418.

In summary, the structures and mechanisms of single-stranded oligonucleotides that are useful in the treatment of different virus infections remains ambiguous.

The present inventors have now found that ssONs inhibit endocytosis and thereby inhibit influenza virus infection. As shown in Example 1, ssONs were found to inhibit some endocytic pathways in human monocyte derived cells (moDCs) while leaving other pathways unaffected. The studies revealed a regulatory role for extracellular ssONs in the endocytic uptake of Toll-like receptor (TLR) ligands and provide a mechanistic explanation for their immunomodulation. In Example 2, dendritic cells were pre-treated with ssON and then exposed to influenza A virus (IAV). There was a marked and highly significant reduction in viral load compared with untreated dendritic cells. Further, as shown in Example 3, there was a significant reduction of viral load in mice when ssON was given either as a prophylactic treatment or as a therapeutic treatment three days after influenza challenge. Example 4 demonstrates that the reduction in viral load in influenza A infected mice occurred without significant changes in cytokine responses.

Without wishing to be bound by any theory, the inventors believe that ssONs that inhibit endocytosis will have a higher anti-viral potency than other oligonucleotides that act by directly binding to the virus to prevent cellular fusion.

Accordingly, a first aspect of the invention provides a single-stranded oligonucleotide (ssON) for use in preventing or treating an influenza virus infection in a subject, wherein the single-stranded oligonucleotide is one that inhibits endocytosis.

By ssON we include the meaning of any single stranded oligonucleotide. The oligonucleotide may be an oligodeoxynucleotide (ODN) or an oligoribonucleotide or an oliogdeoxyribonucleotide. The term oligonucleotide includes to an oligomer or polymer of ribonucleic acid (RNA) or deoxyribonucleic acid (DNA,) or a mimetic thereof. The term includes oligonucleotides composed of naturally occurring nucleo-bases, sugars and covalent internucleoside (backbone) linkages as well as oligonucleotides having non-naturally occurring portions which function similarly. Such modified or substituted oligonucleotides are often preferred over native forms because of desirable properties such as, for example, enhanced cellular uptake, enhanced affinity for nucleic acid target and increased stability in the presence of nucleases. Examples of modifications that can be used are described further below.

Oligonucleotides that include backbone and/or other modifications can also be referred to as oligonucleosides.

Endocytosis is a form of active transport in which a cell transports molecules (such as proteins) into the cell (endo-+cytosis) by engulfing them in an energy-using process.

Endocytosis pathways can be subdivided into four categories: namely, "classical" receptor-mediated endocytosis (also known as clathrin-mediated endocytosis), caveolae (can also be receptor-mediated as described below), macropinocytosis, and phagocytosis.

Clathrin-mediated endocytosis is mediated by the production of small (approx. 100 nm in diameter) vesicles that have a morphologically characteristic coat made up of the cytosolic protein clathrin. Clathrin-coated vesicles (CCVs) are found in virtually all cells and form domains of the plasma membrane termed clathrin-coated pits. Coated pits can concentrate large extracellular molecules that have different receptors responsible for the receptor-mediated endocytosis of ligands, e.g. low density lipoprotein, transferrin, growth factors, antibodies and many others.

Caveolae are the most common reported non-clathrin-coated plasma membrane buds, which exist on the surface of many, but not all cell types. They consist of the cholesterol-binding protein caveolin (Vip21) with a bilayer enriched in cholesterol and glycolipids. Caveolae are small (approx. 50 nm in diameter) flask-shape pits in the membrane that resemble the shape of a cave (hence the name caveolae). They can constitute up to a third of the plasma membrane area of the cells of some tissues, being especially abundant in smooth muscle, type I pneumocytes, fibroblasts, adipocytes, and endothelial cells. Uptake of extracellular molecules is also believed to be specifically mediated via receptors in caveolae.

Potocytosis is a form of receptor-mediated endocytosis that uses caveolae vesicles to bring molecules of various sizes into the cell. Unlike most endocytosis that uses caveolae to deliver contents of vesicles to lysosomes or other organelles, material endocytosed via potocytosis is released into the cytosol.

Macropinocytosis, which usually occurs from highly ruffled regions of the plasma membrane, is the invagination of the cell membrane to form a pocket, which then pinches off into the cell to form a vesicle (0.5-5 µm in diameter) filled with a large volume of extracellular fluid and molecules within it (equivalent to ~100 CCVs). The filling of the pocket occurs in a non-specific manner. The vesicle then travels into the cytosol and fuses with other vesicles such as endosomes and lysosomes.

Phagocytosis is the process by which cells bind and internalize particulate matter larger than around 0.75 µm in diameter, such as small-sized dust particles, cell debris, micro-organisms and apoptotic cells. These processes involve the uptake of larger membrane areas than clathrin-mediated endocytosis and caveolae pathway.

The endocytic pathway of mammalian cells consists of distinct membrane compartments, which internalize molecules from the plasma membrane and recycle them back to the surface (as in early endosomes and recycling endosomes), or sort them to degradation (as in late endosomes and lysosomes).

The endocytosis that is inhibited may be the endocytosis of a particular endocytosis pathway or pathways such as CME and/or CDE as described below. Preferably, the endocytosis that is inhibited is CME and CDE. It is appreciated that not all endocytosis pathways will be inhibited. For example, the ssON does not typically affect macropinocytosis. Thus in a preferred embodiment, the ssON inhibits CDE and CME but does not inhibit macropinocytosis.

By an ssON that inhibits endocytosis we include the meaning of an ssON that reduces the level of endocytosis in a cell to a level less than the level of endocytosis in the cell in the absence of the inhibitor. For example, the ssON may reduce the level of endocytosis to less than 95% or 90% of the level of endocytosis in the cell in the absence of the ssON, such as less than 80%, 70%, 60%, 50%, 40%, 30%, 20% or 10% of the level of endocytosis in the cell in the absence of the ssON. Preferably, the ssON reduces the level of endocytosis in the cell to a substantially undetectable level.

It is appreciated that the cell is one that makes use of endocytosis to transport molecules into the cell. Preferably, the cell is one that may be infected by an influenza virus and where the virus uses endocytosis to infect the cell (eg to avoid recognition by cytoplasmic RNA sensors such as RIG-1 and MDA/5 that trigger high INF-alpha production). Thus, the cell may be an influenza virus host cell. Influenza viruses infect airway epithelial cells, monocytes and monocyte derived dendritic cells, and so it is preferred if the ssON inhibits endocytosis in a cell selected from the group consisting of a monocyte derived dendritic cell, a monocyte and an epithelial cell. Other cells whose endocytosis may be inhibited include keratinocytes and fibroblasts.

Methods of measuring endocytosis are well known in the art and any suitable method can be used. Generally, the methods involve labelling components of the endocytic machinery of the host cell such as early endosomes, late endosomes or lysosomes, directly; measuring the internalisation of molecules that are known to rely on endocytosis for cell entry; or measuring downstream signalling events that are known to rely on endocytosis for their activation.

In terms of direct labelling of the endocytic machinery, the specific structures within the cell may be targeted by transgenic expression of labelled fusion proteins (eg fluorescently labelled fusion proteins such as GFP). For example, several components of the protein machinery thought to be involved endocytosis have been identified such as certain Rab isoforms and the proteins Hrs/STAM, TSG101 and the ESCRT complexes. Labelling of such proteins can allow direct monitoring of the endocytic machinery, and changes in the signal may be used as a readout for endocytosis. It will be appreciated that endocytic structures can be monitored in live cells, or the cells can be fixed, for example for additional analysis such as immunohistochemical analysis.

In relation to the internalisation of molecules known to rely on endocytosis for cell entry, any such molecule can be used and can be easily identified by the skilled person, for example by interrogating the scientific literature. Suitable endocytic markers include low-density lipoprotein (LDL), transferrin, dsRNA, poly(I:C), albumin, tetanus toxin, cholera toxin subunit B (CTB), and dextran. It will be understood that different markers may be used to monitor different endocytic pathways by selecting the markers based on the pathway of interest. For example, LDL, transferrin, dsRNA and poly(I:C) are internalised by clarthrin mediated endocytosis (CME), and so can be used to assess CME; albumin, tetanus toxin and CTB are internalised by caveolin dependent endocytosis (CDE), and so can be used to assess CDE; and fluid phase markers such as dextran are internalised by macropinocytosis, and so can be used to assess macropinocytosis.

Typically, the molecules are detectably labelled so that their fate can be readily detected. For example, the molecules may be labelled with a fluorescent moiety, a radioactive moiety, a chemiluminescent label, an antibody or biotin, or a detectable enzyme. Preferably, the molecule is labelled with a fluorescent moiety such as Alexa fluorophores (647, 488 etc) Texas Red, 6/5'-FAM, Dil, PE, APC, PerCP and FITC. It will be appreciated that when the molecule is labelled, internalisation can be monitored by assessing the decrease in signal outside of the cell, for example at the cell membrane (as the labelled molecule is internalised) and/or the increase in signal inside the cell, for example in the cytosol or a specific compartment such as the endosome (as the labelled molecule is internalised).

Accordingly, in one embodiment, the ssON is one that inhibits the internalisation of an endocytic marker or molecule into a cell such as any one or more of low-density lipoprotein (LDL), transferrin, dsRNA, poly(I:C), albumin, tetanus toxin, and cholera toxin subunit B (CTB). As described in Example 1, the inventors demonstrated that the ssONs of the invention inhibited internalisation of transferrin and CTB, and so in a preferred embodiment, the ssON is one that inhibits CME (eg as demonstrated by inhibition of internalisation of transferrin) and/or CDE (eg as demonstrated by inhibition of internalisation of CTB). The inventors also demonstrated that the ssONs did not inhibit internalisation of dextran, and so in a preferred embodiment, the ssON is one that does not inhibit macropinocytosis (eg as demonstrated of dextran).

Flow cytometry is a preferred technique to measure internalisation of molecules because data can be efficiently quantified, but other methods may be used such as microscopy based methods.

A yet further way of assessing endocytosis is by measuring a downstream signalling event that is known to rely on endocytosis for its activation. For example, a ligand that initiates a signalling cascade may be dependent on endocytosis for its entry into a cell, and so a reporter of the signalling cascade may be used as a readout for endocytosis. If endocytosis is inhibited, less ligand will be internalised and so the signalling through the signalling cascade will be decreased. Often, the signalling cascades are ones that involve the endosome and so can be considered downstream cellular pathways from "signalling endosomes". Thus, assessing endocytosis may involve measuring a cellular pathway downstream of a signalling endosome. Cell signalling from endosomes occurs for receptors, such as NOTCH-family members, tumour necrosis factor receptor (TNFR) 1 and some Toll-like receptors (eg TLR3, TLR7, TLR8 and TLR9), and so it will be appreciated that signalling through any of the NOTCH, TNFR 1, TLR3, TLR7, TLR8 and TLR9 pathways may be used to assess endocytosis.

Measuring cellular signalling is standard practice in the art and may involve measuring the amounts of molecular mediators within the signalling cascade (eg proteins) and/or the amounts of products (eg mRNA and/or proteins) of the signalling cascade. For example, a particular protein whose expression is known to be under the control of a specific signalling pathway may be quantified. Assaying protein levels in a biological sample can occur using any suitable method known in the art. For example, protein concentration can be studied by a range of antibody based methods including immunoassays, such as ELISAs and radioimmunoassays. In some signalling pathways, the cellular location of molecular mediators may change (eg from cytoplasm to nucleus), and so assessing the cellular location of one or more molecular mediators of a signalling pathway may also be used to assess cellular signalling, for example using immunohistochemistry. In addition, many signalling pathways control a specific promoter, and so for these signalling pathways a reporter gene may be used to assess signalling as is well known in the art. Several techniques are available in the art to detect and measure expression of a reporter gene which would be suitable for use in the present invention. Many of these are available in kits both for determining expression in vitro and in vivo.

Accordingly, in another embodiment, the ssON is one that inhibits a downstream signalling event that is known to rely on endocytosis for its activation. As described in Example 1, the inventors measured endocytosis by assessing TLR3 signalling, using expression of co-stimulatory molecules CD86, CD83 and CD80, and secretion of the pro-inflammatory cytokine IL-6 as a readout. Hence, in a preferred embodiment, the ssON is one which inhibits TLR3 signalling. Thus, preferably the invention relates to an ssON, methods and/or uses as defined herein in which the ssON is an inhibitor of TLR3. Therefore, in an embodiment, the invention provides a ssON which is an inhibitor of TLR3 for use in preventing or treating an influenza virus infection in a subject, wherein the single-stranded oligonucleotide is one that inhibits endocytosis.

Other TLRs that are known to be dependent on endocytosis are TLR7 and TLR8, and so in an additional or alternative embodiment, the ssON is one that inhibits any one or both of TLR7 and TLR8. TLR4 is partially dependent on endocytosis since it has two distinct signalling pathways, one reliant on CME and the other being MyD88 dependent from the plasma membrane. Thus, the ssON may be one that inhibits the CME-mediated signalling of the TLR4 signalling pathway.

It will be appreciated that other techniques may also be used to assess endocytosis. A direct method is the capacitance technique which measures change in membrane surface area associated with fusion and retrieval of vesicles (Llobet et al Neuron 40:1075-1086). Another approach involves fluorescence imaging of vesicles labelled with a membrane dye such as FM1-43 or a detectable fusion protein (eg GFP fusion protein) (Llobet et al, Neuron 40:1075-86). Real measurement of endocytosis may be carried out using interference of light. The method uses interference reflection microscopy (IRM) to visualise areas of destructive interference occurring when light is reflected from the region of surface membrane in close apposition to a glass coverslip. (Llobet et al, Neuron 40: 1075-86). Other assays include biochemical assays such as covalent modification of surface receptors with biotin and immunofluorescence assays that follow receptors down the endosomal pathway using antibodies that recognise epitopes in the extracellular domain of particular receptors. Any suitable method may be used.

As demonstrated in the Examples, the inventors have shown that ssONs inhibit endocytosis and thereby prevent a key route of entry of an influenza virus into a cell. Without wishing to be bound by any theory, the inventors believe that this makes the antiviral activity of the ssONs more potent than known antiviral ssONs (eg from WO 2006/042418) which rely on direct binding to virions to have their effect. It will be appreciated that electron microscopy can be used to assess the location of viruses during infection, eg by super time lapse microscopy, and so can be used to probe whether an ssON inhibits virus infection by inhibiting endocytosis or by direct binding to the virus.

It is preferred if the ssONs used in the context of the invention described herein do not stimulate the innate immune response in monocyte derived dendritic cells. For example it is preferred if the ssON do not stimulate one or more of the innate immune sensors such as TLR3, TLR7 or TLR9. Methods for assessing whether an ssON would stimulate one or more innate immune sensors are well known in the art, and include, for example, measuring signalling pathways associated with an innate immune sensor such as the TLR9 signalling pathway. Methods for assessing the activity of a signalling pathway are also well known in the art and are described elsewhere herein. Whether the ssON stimulates one or more immune sensors can also be assessed by measuring the secretion of cytokines known to be associated with the innate immune response. Techniques that can be used also include cytokine secretion by ELISA, Luminex or intracellular staining and quantification by flow cytometry, and RNA quantification such as by RT-PCR, RNAseq or microarrays.

Thus, it will be appreciated that the ssON used in the context of the present invention are preferably ones which inhibit endocytosis and which do not stimulate an innate immune response in monocyte derived dendritic cells. Without wishing to be bound by any theory, the inventors believe that naturally occurring non-coding sequences in the human genome would inhibit endocytosis of human cells, and so the invention is based on a natural mechanism to temporarily shut down endocytosis. By being based on natural sequences, the oligonucleotides are less likely to trigger an innate immune response. Such natural sequences can then be modified to make them more stable as described further below.

In an embodiment, the length of the ssON is between 20 and 70 nucleotides, such as between 25 and 70 nucleotides.

It is preferred if the length of the ssON is at least 25 nucleotides. Thus, the invention provides an ssON for use in preventing or treating an influenza virus infection in a subject, wherein the ssON is one that inhibits endocytosis and is at least 25 nucleotides in length.

Preferably, the length of the ssON is between 25 and 70 nucleotides, such as between 25 and 60 nucleotides, 25 and 50 nucleotides, 25 and 40 nucleotides or 25 and 35 nucleotides.

In a preferred embodiment, the length of the ssON is between 28 and 70 nucleotides, such as between 28 and 60 nucleotides, 28 and 50 nucleotides, 28 and 40 nucleotides or 28 and 35 nucleotides.

In a particularly preferred embodiment, the length of the ssON is between 25 and 40 nucleotides such as between 25 and 39 nucleotides, or between 28 and 40 nucleotides. For example, the length of the ssON may be between 29 and 38 nucleotides or between 30 and 36 nucleotides. The length of the ssON may be at least 25, 26, 27, 28, 29, 30, 31, 32, 33, 34, 35, 36, 37, 38, 39 or 40 nucleotides, and/or the length of the ssON may be no more than 40, 39, 38, 37, 36, 35, 34, 33, 32, 31, 30, 29, 28, 27, 26 or 25 nucleotides. Further preferred ranges of length include 30-70, such as 30-60, 30-50, 30-40 or 30-35 nucleotides. A further preferred range is 25-39 nucleotides.

Many of the ssONs shown in Table 1 below are 35 nucleotides in length and so in a preferred embodiment, the length of the ssON is 35 nucleotides in length.

It is preferred that at least 50%, 60%, 70%, 80% or 90% of the internucleotide linkages in the ssON are phosphorothioate internucleotide linkages. The terms "phosphorothioate internucleotide linkages" and "PS linkages" refer to internucleotide linkages in which one of the non-bridging oxygens in the DNA phosphate (PO) backbone is replaced by sulfur. Preferably, 95% or more preferably 100% of the internucleotide linkages in the ssON to be used according to the invention are PS internucleotide linkages. Consequently, the invention includes the use of ssONs wherein some internucleotide linkages (such as one, two, three, or more internucleotide linkages) are PO linkages without sulfur, while the remaining linkages are PS linkages. In cases where the ssON comprises phosphate groups in the 5'-terminal and/or 3'-terminal, such phosphate groups may be modified (PS) or unmodified (PO) groups.

It will be appreciated that the ssON may comprise 2'-O-methyl modifications, such as at least 2, 3, 4, 5 or 6 2'-O-methyl modifications. By 2'-O-methyl modifications, we include the meaning of nucleotide modifications where a methyl group is added to the 2'-hydroxyl group of the ribose moiety of a nucleoside.

In an embodiment, the ssON comprises at least four phosphorothioate internucleotide linkages (eg at least 5 or 6

PS linkages) and at least four 2'-O-methyl modifications (eg at least 5 or 6 2'-O-methyl modifications).

In a further embodiment, the ssON comprises at least six phosphorothioate internucleotide linkages and at least six 2'-O-methyl modifications.

The ssON to be used according to the invention may comprise additional chemical modifications. Chemically modified oligonucleotides are known in the art and disclosed in e.g. Jarver, P. et al. 2014. Nucleic acid therapeutics 24:37-47; and Deleavey, G. F. & Damha, M. J. 2012. Chemistry & Biology 19:937-954. Possible chemical modifications include e.g. LNA (Locked Nucleic Acid), wherein the ribose moiety is modified with an extra bridge connecting the 2' oxygen and 4' carbon. Further, the ssON could comprise a mix of ribose and deoxyribose as the five-carbon sugar. In addition, one or more nucleobases in the ssON could be modified. Oligonucleotide base modifications include methylation of cytosine to form 5-methylcytosine, and methylation of adenosine to form N6-methyladenosine.

It is preferred if the ssON does not contain a CpG motif. By CpG motif we include the meaning of an oligonucleotide (eg a short single-stranded nucleic acid molecule) that contains a cytosine triphosphate deoxynucleotide ("C") followed by a guanine triphosphate deoxynucleotide ("G"). The "p" refers to the phosphodiester or phosphorothioate link between consecutive nucleotides. CpG motifs are considered pathogen-associated molecular patterns (PAMPs) due to their abundance in microbial genomes but their rarity in vertebrate genomes. The CpG PAMP is recognized by the pattern recognition receptor (PRR) Toll-Like Receptor 9 (TLR9), which is constitutively expressed primarily in B cells and plasmacytoid dendritic cells (pDCs) in humans and other higher primates. Preferably, therefore, the invention does not include the use of ssONs comprising CpG motifs capable of stimulating a TLR9 response.

It is preferred if the ssON has a "sequence independent" mode of action, does not have antisense activity and is not complementary to a gene. More specifically, it is preferred if not more than 16 consecutive nucleotides in the ssON are complementary with any human mRNA sequence (eg human mRNA coding sequence) or virus (eg influenza such as influenza A) gene. Preferably, the ssON is essentially "non-complementary" with any human mRNA sequence (eg human mRNA coding sequence) or virus (eg influenza such as influenza A) gene. The term "non-complementary" will be understood to refer to nucleic acid sequences that are not capable of precise pairing (of purine or pyrimidine bases between the two strands of nucleic acids sequences) under moderate or stringent hybridization conditions (eg 5-10° C. below Tm), as are well known in the art. For example, the ssON is preferably non-complementary to nucleotide sequences coding for receptor proteins, e.g. Toll-like receptors, such as TLR3 or TLR9, or any other protein which recognize DAMPs (Damage-associated molecular pattern) or PAMPs (Pathogen-associated molecular pattern molecules). It will thus be understood that the ssONs to be used according to the invention are not "antisense" molecules that are complementary to a messenger RNA (mRNA) strand transcribed within a cell or encoded by viral (eg influenza such as influenza A) nucleic acids.

A person having ordinary skill in the art will be able to identify oligonucleotide sequences which are "non-complementary" as defined according to the present invention. For instance, the skilled person could use well-known tools such as the BLAST algorithm as implemented online by the US National Center for Biotechnology Information. See e.g. Madden, T. 2013. The BLAST Sequence Analysis Tool. The NCBI Handbook [Internet], $2^{nd}$ edition (www.ncbi.nlm.nih.gov/bookiNBK153387).

In a preferred embodiment, the ssON to be used according to the invention does not target (eg bind specifically to) any specific viral (eg influenza such as influenza A) gene or polypeptide. As mentioned above, it is known in the art that virus infections can be treated with oligonucleotides, polynucleotides or aptamers that specifically target virus-encoded molecules. For instance, Arnon et al (US 2013/0079390) discloses a nucleic acid aptamer molecule capable of binding to hemagglutinin (a surface antigen on influenza virus). Thus, it is particularly preferred that the ssON does not target (eg bind specifically to) an influenza (eg influenza A) virus gene or polypeptide, such as any one or more of neuraminidase (NA), hemagglutnin and an envelope protein such as M2. Binding of oligonucleotides to other nucleic acid molecules and polypeptides can be tested using routine techniques in the art.

It will thus be understood that according to the invention, the ssON is typically useful based on its tertiary structure, eg the spatial organisation, and not solely dependent on its primary structure, ie the sequence of nucleotides.

In yet a further preferred embodiment, the ssON for use according to the invention is not self-complementary. The term "not self-complementary" will be understood to mean that the ssON does not have any self-complementary sequences that would allow two ssONs to dimerize, or that would allow parts of the oligonucleotide to fold and pair with itself to form stem loops. It is well-known that stem loop (also referred to as "hair-pin" loop) base pairing can occur in single-stranded DNA or RNA. It occurs when two regions of the same strand, usually complementary when read in opposite directions, base-pair to form a double helix that ends in an unpaired loop.

A person having ordinary skill in the art will be able to identify self-complementary sequences by comparing parts of the ssON sequence and detecting whether Watson-Crick base pairing (CG and AT/AU) could occur. Alternatively, a software tool such as Oligo Calc: Oligonucleotide Properties Calculator (www.basic.northwestern.edu/biotools/oligocalc.html) could be used to detect self-complementary sequences. Models for self-dimerization and hairpin formation in oligonucleotides are known in the art and are described in e.g. Hilbers, C. W. 1987. Anal Chem 327:70; Serra, M. J. 1993. Nucleic Acids Res 21:3845-3849; and Vallone, P. M. 1999. Biopolymers. 50:425-442. As a general rule, at least 5 base pairs would be required for self-dimerization, and at least 4 base pairs would be required for hair-pin formation. Consequently, preferably the ssON as defined above does not comprise more than 3 consecutive nucleotides that could form base pairs with another sequence of 3 consecutive nucleotides within the same ssON molecule.

Preferably, the said ssON is a single-stranded oligodeoxynucleotide (ssODN). However, the invention also provides the use of ssONs that are stabilized single-stranded RNA (ribonucleic acid) molecules. As will be understood by the skilled person, when the ssON is an oligodeoxynucleotide, the monosaccharides in the ssON are 2'-deoxyribose. Thus, the monosaccharides in the ssON may be selected from the group consisting of 2'-deoxyribose and 2'-O-methylribose. In the present context the term "ssODN" also includes oligonucleotides comprising one or more modified monosaccharides such as 2'-O-methylribose.

It is preferred if the ssON for use according to the invention does not contain TTAGGG.

It is preferred if the ssON for use according to the invention does not comprise at least one GGGG sequence and/or does not comprise at least one GGG sequence (eg TTAGGG).

It is also preferred that the ssON for use according to the invention comprises at least three different nucleotides selected from the group consisting of A, C, G and T, or at least four different nucleotides selected from the group consisting of A, C, G and T. In this case, it will be appreciated that the ssON is not composed of single repeats or dinucleotide repeats, such as repeats of the formula A(x), C(x), G(x), T(x), AC(x), AG(x), AT(x), CG(x), CT(x), or GT(x), wherein x is an integer.

In an embodiment, at least 30% of the nucleobases in the ssON are chosen from A (Adenine) and T (Thymine) and U (Uracil). Preferably, at least 35%, 40%, 45%, 50%, 55%, or 60% of the nucleobases in the ssON are chosen from A, T and U. When the ssON is an oligodeoxynucleotide (ssODN), containing deoxyribose as its pentose component, the nucleobases are normally chosen from A and T. When the ssON is a ribonucleotide containing ribose, the nucleobases are normally chosen from A and U. However, the ssONs according to the invention could include synthetic variants which may differ from naturally occurring oligonucleotides. For instance, the ssON could comprise a deoxyuridine moiety (i.e. uracil bound to deoxyribose). The ssON could also comprise nucleobase analogues, which are well known in the art and include e.g. xanthine, hypoxanthine, 7-methylguanine, 5-methylcytosine, and 5-hydroxymethylcytosine.

In a particularly preferred embodiment, the ssON is one wherein:
(a) the length of the ssON is at least 25 nucleotides (eg at least 28 nucleotides);
(b) either (i) at least 90% of the internucleotide linkages in the ssON are phosphorothioate internucleotide linkages; or (ii) the ssON comprises at least four phosphorothioate internucleotide linkages and at least four 2'-O-methyl modifications; and
(c) the ssON does not contain any CpG motifs. Preferably, (i) the ssON does not comprise at least one GGGG sequence and/or does not comprise at least one GGG sequence (eg TTAGGG); and/or (ii) the ssON comprises at least three different nucleotides selected from the group consisting of A, C, G and T, or at least four different nucleotides selected from the group consisting of A, C, G and T.

In a particularly preferred embodiment, the ssON (eg ss ODN) is one wherein:
(a) the length of the ssON is at least 25 nucleotides (eg at least 28 nucleotides);
(b) either (i) at least 90% of the internucleotide linkages in the ssON are phosphorothioate internucleotide linkages; or (ii) the ssON comprises at least four phosphorothioate internucleotide linkages and at least four 2'-O-methyl modifications;
(c) the ssON does not contain any CpG motifs; and
(d) (i) the ssON is non-complementary to any human mRNA and/or influenza gene and/or (ii) the ssON is not self-complementary. Preferably, (i) the ssON does not comprise at least one GGGG sequence and/or does not comprise at least one GGG sequence (eg TTAGGG); and/or (ii) the ssON comprises at least three different nucleotides selected from the group consisting of A, C, G and T, or at least four different nucleotides selected from the group consisting of A, C, G and T.

In a particularly preferred embodiment, the ssON (eg ss ODN) is one wherein:
(a) the length of the ssON is at least 25 nucleotides (eg at least 28 nucleotides);
(b) either (i) at least 90% of the internucleotide linkages in the ssON are phosphorothioate internucleotide linkages; or (ii) the ssON comprises at least four phosphorothioate internucleotide linkages and at least four 2'-O-methyl modifications; and
(c) the ssON does not contain any CpG motifs; and
(d) the ssON does not target (eg bind specifically to) any specific viral (eg influenza such as influenza A) gene or polypeptide. Preferably, (i) the ssON does not comprise at least one GGGG sequence and/or does not comprise at least one GGG sequence (eg TTAGGG); and/or (ii) the ssON comprises at least three different nucleotides selected from the group consisting of A, C, G and T, or at least four different nucleotides selected from the group consisting of A, C, G and T.

In a particularly preferred embodiment, the ssON (eg ss ODN) is one wherein:
(a) the length of the ssON is at least 25 nucleotides (eg at least 28 nucleotides);
(b) either (i) at least 90% of the internucleotide linkages in the ssON are phosphorothioate internucleotide linkages; or (ii) the ssON comprises at least four phosphorothioate internucleotide linkages and at least four 2'-O-methyl modifications; and
(c) the ssON does not contain any CpG motifs;
(d) the ssON does not target (eg bind specifically to) any specific viral (eg influenza such as influenza A) gene or polypeptide; and
(e) (i) the ssON is non-complementary to any human mRNA and/or influenza gene and/or (ii) the ssON is not self-complementary. Preferably, (i) the ssON does not comprise at least one GGGG sequence and/or does not comprise at least one GGG sequence (eg TTAGGG); and/or (ii) the ssON comprises at least three different nucleotides selected from the group consisting of A, C, G and T, or at least four different nucleotides selected from the group consisting of A, C, G and T.

As described in the Examples, the inventors have exemplified the invention in the context of 24 ssONs. Thus, in an especially preferred embodiment, the ssON comprises or consists of a polynucleotide having a sequence of any one of SEQ ID NOs: 1-24 listed in Table 1, or the complementary sequence thereof. Particularly preferred ssONs amongst these sequences are SEQ ID NOs: 1, 3, 4, 7, 8, 10, 11, 13-22 and 24.

In a further embodiment, the ssON comprises or consists of a polynucleotide having a sequence sharing at least 60% sequence identity with a sequence of any one of SEQ ID NOs: 1-24 listed in Table 1, or a complementary sequence thereof, such as at least 65%, 70%, 71%, 72%, 73%, 74%, 75%, 76%, 77%, 78%, 79%, 80% sequence identity, and more preferably at least 81%, 82%, 83%, 84%, 85%, 86%, 87%, 88%, 89% or 90% sequence identity, and even more preferably at least 91%, 92%, 93%, 94%, 95%, 96%, 97%, 98%, or 99% sequence identity with a sequence of any one of SEQ ID NOs: 1-24 listed in Table 1, or a complementary sequence thereof. Again, particularly preferred ssONs amongst these sequences are SEQ ID NOs: 1, 3, 4, 7, 8, 10, 11, 13-22 and 24.

By the term "sequence identity", we include the meaning of a quantitative measure of the degree of homology between two nucleic acid sequences or between two nucleic acid sequences of equal length. If the two sequences to be compared are not of equal length, they must be aligned to give the best possible fit, allowing the insertion of gaps or, alternatively, truncation at the ends of the nucleotide sequences. The sequence identity can be calculated, wherein Ndif is the total number of non-identical residues in the two sequences when aligned and wherein Nref is the number of residues in one of the sequences, preferably sequence identity is calculated over the full length reference as provided herein. A gap is typically counted as non-identity of the specific residue(s).

With respect to all embodiments of the invention relating to nucleotide sequences, the percentage of sequence identity between one or more sequences may also be based on alignments using the NCBI BLAST software https://blast.ncbi.nlm.nih.qov/Blast.cqi?PAGE_TYPE=BlastSearch&BLAST_SPEC=blast2seq &LINK_LOC=aliqn2seq) or the clustalW software (http:/www.ebi.ac.uk/clustalW/index.html), for example with default settings. Default settings for nucleotide sequence alignments in clustalW are:

Alignment=3Dfull, Gap Open 10.00, Gap Ext. 0.20, Gap separation Dist. 4, DNA weight matrix: identity (IUB).

In a further embodiment, the ssON comprises or consists of a polynucleotide having a sequence of any one of SEQ ID NOs: 1-24 listed in Table 1, or a complementary sequence thereof, wherein up to ten nucleotides are replaced by another nucleotide (eg up to 2, 3, 4, 5, 6, 7, 8, 9 or 10 nucleotides are replaced by another nucleotide). For example, the ssON may comprise or consist of a polynucleotide having a sequence of any one of SEQ ID NOs: 1-24 listed in Table 1, or a complementary sequence thereof, wherein between 2-10, such as 3-9 or 4-8 nucleotides are replaced by another nucleotide. Again, particularly preferred ssONs amongst these sequences are SEQ ID Nos: 1, 3, 4, 7, 8, 10, 11, 13-22 and 24.

For the avoidance of doubt, when ssONs are defined by reference to any of the sequences in Table 1 below, it will be appreciated that the ssONs do not need to contain each and every modification depicted in Table 1 in respect of any of those sequences. Preferably, when the ssONs are defined by reference to any of the sequences in Table 1 below, they do contain each and every modification depicted in Table 1 in respect of whichever sequence, however, it is not essential. The ssON may simply be defined by reference to the nucleotide sequence of a particular sequence depicted in Table 1, without any chemical modifications or with different chemical modifications to those depicted in Table 1.

The first aspect of the invention includes the use of an ssON in the manufacture of a medicament for preventing or treating an influenza virus infection in a subject, wherein the ssON is one that inhibits endocytosis.

The first aspect of the invention also includes a method for preventing or treating an influenza virus infection in a subject, comprising administering an ssON to the subject, wherein the ssON is one that inhibits endocytosis.

In both instances, preferences for the ssON include those described above. Particularly preferred ssONs are SEQ ID NOs: 1, 3, 4, 7, 8, 10, 11, 13-22 and 24.

For the avoidance of doubt, it will be appreciated that, in any aspects of the invention described herein, the ssON does not include any of the ssONs mentioned in Table 21 of WO2006/042418 (see pages 127-129c, for example REP2006, REP2018, REP2029, REP2028, REP2033, REP2055, REP2056 and REP2057) incorporated herein by reference, and does not include any of the ssONs mentioned in Table 1 and/or Table 7 of US2011/0124715 (see pages 6, 7, 15 and 16) incorporated herein by reference.

In a preferred embodiment, the influenza virus is influenza A virus (eg H1N1 subtype). However, it will be appreciated that the invention is also applicable to influenza B virus, and influenza C virus, and so in another embodiment, the influenza virus is influenza B virus or influenza C virus, or a subtype thereof.

It will also be appreciated that the influenza is preferably on which relies upon endocytosis for cell entry (eg CDE and/or CME). Methods for assessing the endocytic pathways of influenza viruses include molecule biology and optical microscopy techniques and are described in Lakadamyali et al, 2004 (Microbes Infect 6(1): 929) and Matlin et al, 1981 (J Cell Biol 91(3): 601).

By preventing or treating an influenza virus infection we include the meaning of reducing or alleviating symptoms in a patient (i.e. palliative use), preventing symptoms from worsening or progressing, treating the disorder (e.g. by inhibition or elimination of the causative virus), or prevention of the condition or disorder in a subject who is free therefrom.

It will be appreciated that in this therapeutic aspect of the invention, the method or use may include identifying a subject who has or is likely to have an influenza virus infection or who is free of an influenza virus infection or is at risk of developing an influenza virus infection (eg during an epidemic or pandemic), administering the ssON according to the first aspect of the invention to the subject, and monitoring the levels of the influenza virus in the subject either by conducting tests to determine the viral load or by monitoring the clinical symptoms of the subject. Depending on the results of the monitoring step, it may be necessary to administer more of the ssON.

By viral load, also known as viral burden, viral titre or viral titer, we include the meaning of a numerical expression of the quantity of virus in a given volume. It is often expressed as viral particles, or infectious particles per mL depending on the type of assay. The viral load in a subject can be determined according to any suitable method known in the art, and typically involve nucleic acid tests. For example, a sample may be obtained from the subject (eg lung fluid or blood sample) and the viral nucleic acid amplified by PCR, or probes specific for viral nucleic acid may be added and amplified or detected after a wash step. Further details and examples of such tests are provided in the Examples below.

It will also be appreciated that the invention lends itself to selecting the most appropriate ssON to be administered to patients, for example during a virus epidemic or pandemic. In this case, the efficacy of the ssON (or a range thereof) against a virus strain in question (eg a particular influenza virus strain that has been isolated from a patient, for example during an epidemic or pandemic) can be tested. Typically, this would be carried out in vitro or in an animal model whereby cells in vitro or an animal model are infected with the virus, and the effect of one or more ssONs on viral load monitored. The ssON with the most efficacy can then be used to treat the patient(s) or to prevent influenza infection in one or more subjects during an epidemic or pandemic. A suitable in vitro test involving human monocyte-derived dendritic cells is described in detail in the Examples below.

Preferably, in the context of any aspect of the invention described herein, the subject to be treated is a human. Alternatively, the subject may be an animal, for example a domesticated animal (for example a dog or cat), a laboratory animal (for example laboratory rodent, for example ferret, mouse, rat, rabbit, a monkey, a pig, a lamb or a bird), an animal important in agriculture (i.e. livestock), for example horses, cattle, sheep, pigs, lambs, chickens, swine, or goats, a bird, or a non-human primate (eg a monkey). It will be appreciated that non-human primates could be administered the ssON in a laboratory context or in the wild.

In one embodiment, the ssON is administered as a monotherapy.

In another embodiment, the ssON is administered in combination with an additional therapeutic agent.

Thus, the invention provides an ssON for use in preventing or treating an influenza virus infection in a subject, wherein the ssON is one that inhibits endocytosis, and wherein the subject is administered an additional therapeutic agent. It is appreciated that the ssON and the additional therapeutic agent need not be part of the same composition, but may be administered separately as discussed further below.

Similarly, the invention includes the use of an ssON in the manufacture of a medicament for preventing or treating an influenza virus infection in a subject, wherein the ssON is one that inhibits endocytosis, and wherein the subject is administered an additional therapeutic agent.

Likewise, the invention includes a method of preventing or treating an influenza virus infection in a subject, comprising administering to the subject an ssON that inhibits endocytosis and an additional therapeutic agent.

Preferences for the ssON and influenza virus are as described above.

In one embodiment, the ssON and additional therapeutic agent are administered substantially simultaneously to the subject In an alternative embodiment, the ssON and the additional therapeutic agent are administered sequentially to the subject. Thus, the individual may be one who has already been administered the ssON, and the additional therapeutic agent is subsequently administered to the subject. Alternatively, the subject may be one who has already been administered the additional therapeutic agent, and the ssON is subsequently administered to the individual.

It will be appreciated that the subject may be one who is suffering from asthma, and so it may be desirable to also administer to the subject a steroid, a beta-2-agonist, a leukotriene antagonist or an anti-histamine. Thus, in one embodiment, the additional therapeutic agent is one or more of a steroid, a beta-2-agonist, a leukotriene antagonist or an anti-histamine.

Similarly, it will be appreciated that the subject may be one who is suffering from a fever, and so it may be desirable to administer to the subject a non-steroidal anti-inflammatory drug (NSAID) or paracetamol. Thus, in another embodiment, the additional therapeutic agent is one or more of a NSAID or paracetamol.

The additional therapeutic agent may be a further antiviral agent. The term "antiviral agent" includes the meaning of any substance that reduces or blocks the function, or growth, of a virus or causes destruction of a virus For example, other antivirals may be used that target different steps in the viral life cycle such as neuraminidase inhibitors, inhibitors of RNA polymerase, inihibitors of acid polymerase (PA) endonuclease inhibitor, polymerase basic protein 2 (PB2) inhibitor, alpha-glucosidase inhibitor, a treatment targeting haemagglutinin or M2, for example therapeutic antibodies (including antibody binding fragments), interferon-alpha or beta based products. Particular examples of antiviral agents are acyclovir, penciclovar, lamivudine, ribavirin, zanamivir, laninamivir, peramivir, idoxuridine, oseltamivir, roflual, amantadine, remantidine, relenza, GR-121167, GC167, neu5ac2en, maxamine, peramivir, or thymalfasin. Any one or more of the antiviral agents listed herein may constitute the additional therapeutic agent in the context of the invention.

In an embodiment, the subject is not administered a dsRNA analogue such as poly (I:C).

Typically, the route of administration is selected from parenteral, intramuscular, subcutaneous, epidermal, intradermal intraperitoneal, intravenous, mucosal delivery, oral, sublingual, dermal, transdermal, topical, buccal, inhalation, intranasal, aerosol, intraocular, intratracheal, intrarectal, vaginal, gene gun, dermal patch, eye drop or mouthwash. Desirably, the said ssON is soluble in water and has effects after local delivery to mucosal surfaces.

The ssON can be systemically administered in an amount from about 1 µg/kg to 10 mg/kg body weight; preferably from about 1 µg/kg to about 1 mg/kg; and more preferably from about 1 µg/kg to about 100 µg/kg. Other preferred ranges include from about 10 µg/kg to about 10 mg/kg; from about 10 µg/kg to about 1 mg/kg; and from about 10 µg/kg to about 100 µg/kg body weight.

The inventors have identified new ssONs that inhibit endocytosis and which are therefore useful in preventing or treating influenza virus infection.

Accordingly, a second aspect of the invention provides an ssON that comprises or consists of a polynucleotide having a sequence sharing at least 60% sequence identity with a sequence of any one of SEQ ID NOs: 13-21 listed in Table 1, or a complementary sequence thereof, such as at least 65%, 70%, 71%, 72%, 73%, 74%, 75%, 76%, 77%, 78%, 79%, 80% sequence identity, and more preferably at least 81%, 82%, 83%, 84%, 85%, 86%, 87%, 88%, 89% or 90% sequence identity, and even more preferably at least 91%, 92%, 93%, 94%, 95%, 96%, 97%, 98%, or 99% sequence identity with a sequence of any one of SEQ ID NOs: 13-21 listed in Table 1, or a complementary sequence thereof.

In a preferred embodiment, the ssON comprises or consists of a polynucleotide having a sequence sharing at least 85% sequence identity with a sequence of any one of SEQ ID NOs: 13-21 listed in Table 1, or a complementary sequence thereof, and more preferably 90%, 91%, 92%, 93%, 94%, 95%, 96%, 97%, 98%, or 99% sequence identity with a sequence of any one of SEQ ID NOs: 13-21 listed in Table 1, or a complementary sequence thereof.

It will be appreciated that this aspect of the invention includes a ssON that comprises or consists of a polynucleotide having a sequence of any one of SEQ ID NOs: 13-21 listed in Table 1, or a complementary sequence thereof, wherein up to ten nucleotides are replaced by another nucleotide (eg up to 2, 3, 4, 5, 6, 7, 8, 9 or 10 nucleotides are replaced by another nucleotide). For example, the ssON may comprise or consist of a polynucleotide having a sequence of any one of SEQ ID NOs: 13-21 listed in Table 1, or a complementary sequence thereof, wherein between 2-10, such as 3-9 or 4-8 nucleotides are replaced by another nucleotide.

Most preferably, the ssON of the second aspect of the invention comprises or consists of a polynucleotide having a sequence of any one of SEQ ID NOs: 13-21 listed in Table 1, The length of the ssON of the second aspect of the invention may be between 20 and 70 nucleotides, such as between 25 and 70 nucleotides. It is preferred if the length of the ssON is at least 25 nucleotides.

Preferably, the length of the ssON is between 25 and 70 nucleotides, such as between 25 and 60 nucleotides, 25 and 50 nucleotides, 25 and 40 nucleotides or 25 and 35 nucleotides.

Preferably, the length of the ssON is between 28 and 70 nucleotides, such as between 28 and 60 nucleotides, 28 and 50 nucleotides, 28 and 40 nucleotides or 28 and 35 nucleotides.

In a particularly preferred embodiment, the length of the ssON is between 25 and 40 nucleotides, or between 28 and 40 nucleotides. For example, the length of the ssON may be between 29 and 38 nucleotides or between 30 and 36 nucleotides. The length of the ssON may be at least 25, 26, 27, 28, 29, 30, 31, 32, 33, 34, 35, 36, 37, 38, 39 or 40 nucleotides, and/or the length of the ssON may be no more than 40, 39, 38, 37, 36, 35, 34, 33, 32, 31, 30, 29, 28, 27, 26 or 25 nucleotides. Further preferred ranges of length include 30-70, such as 30-60, 30-50, 30-40 or 30-35 nucleotides.

Many of the ssONs of SEQ ID NOs: 13-21 shown in Table 1 below are 35 nucleotides in length and so in a preferred embodiment, the length of the ssON is 35 nucleotides in length.

It is preferred that at least 50%, 60%, 70%, 80% or 90% of the internucleotide linkages in the ssON of the second aspect of the invention are phosphorothioate internucleotide linkages, as described above. Preferably, 95% or more preferably 100% of the internucleotide linkages in the ssON are PS internucleotide linkages. Thus the ssON of the second aspect of the invention may have some internucleotide linkages (such as one, two, three, or more internucleotide linkages) which are PO linkages without sulfur, while the remaining linkages are PS linkages.

Other preferences for the ssON of the second aspect of the invention include those described above in relation to the first aspect of the invention.

For example, the ssON of the second aspect of the invention may comprise 2'-O-methyl modifications, and/or other chemical modifications. Preferably, the ssON comprises at least four phosphorothioate internucleotide linkages (eg at least 5 or 6 PS linkages) and at least four 2'-O-methyl modifications (eg at least 5 or 6 2'-O-methyl modifications).

Also, it is preferred if the ssON of the second aspect of the invention does not contain a CpG motif.

It is preferred if the ssON of the second aspect of the invention has a "sequence independent" mode of action, does not have antisense activity and is not complementary to a gene. More specifically, it is preferred if not more than 16 consecutive nucleotides in the ssON are complementary with any human mRNA sequence (eg human mRNA coding sequence) or virus (eg influenza such as influenza A) gene.

In an embodiment, the ssON of the second aspect of the invention does not target (eg bind specifically to) any specific viral (eg influenza such as influenza A) gene or polypeptide.

In yet a further preferred embodiment, the ssON according to the second aspect of the invention is not self-complementary.

Preferably, the ssON of the second aspect of the invention is a single-stranded oligodeoxynucleotide (ssODN), although it is appreciated that it may be a single-stranded RNA (ribonucleic acid) molecule as described above.

In an embodiment, the ssON of the second aspect of the invention does not contain TTAGGG.

In an embodiment, the ssON of the second aspect of the invention does not comprise at least one GGGG sequence and/or does not comprise at least one GGG sequence (eg TTAGGG).

It is preferred that the ssON of the second aspect of the invention comprises at least three different nucleotides selected from the group consisting of A, C, G and T, or at least four different nucleotides selected from the group consisting of A, C, G and T. In this case, it will be appreciated that the ssON is not composed of single repeats or dinucleotide repeats, such as repeats of the formula A(x), C(x), G(x), T(x), AC(x), AG(x), AT(x), CG(x), CT(x), or GT(x), wherein x is an integer.

As described in the Examples below, the inventors have demonstrated that ssONs inhibit endocytosis, and so it will be appreciated that the ssON of the second aspect of the invention may inhibit endocytosis. Preferences for the sub-types of endocytosis, and how to measure inhibition are described above in relation to the first aspect of the invention. In a particularly preferred embodiment, the ssON of the second aspect of the invention is one wherein:

(a) the ssON comprises or consists of a polynucleotide having a sequence sharing at least 60% sequence identity (preferably 100% sequence identity) with a sequence of any one of SEQ ID NOs: 13-21 listed in Table 1, or a complementary sequence thereof;

(b) either (i) at least 90% of the internucleotide linkages in the ssON are phosphorothioate internucleotide linkages; or (ii) the ssON comprises at least four phosphorothioate internucleotide linkages and at least four 2'-O-methyl modifications; and (c) the ssON does not contain any CpG motifs. Preferably, (i) the ssON does not comprise at least one GGGG sequence and/or does not comprise at least one GGG sequence (eg TTAGGG); and/or (ii) the ssON comprises at least three different nucleotides selected from the group consisting of A, C, G and T, or at least four different nucleotides selected from the group consisting of A, C, G and T.

In a particularly preferred embodiment, the ssON of the second aspect of the invention is one wherein:

(a) the ssON comprises or consists of a polynucleotide having a sequence sharing at least 60% sequence identity (preferably 100% sequence identity) with a sequence of any one of SEQ ID NOs: 13-21 listed in Table 1, or a complementary sequence thereof;

(b) either (i) at least 90% of the internucleotide linkages in the ssON are phosphorothioate internucleotide linkages; or (ii) the ssON comprises at least four phosphorothioate internucleotide linkages and at least four 2'-O-methyl modifications;

(c) the ssON does not contain any CpG motifs; and (d) (i) the ssON is non-complementary to any human mRNA and/or influenza gene and/or (ii) the ssON is not self-complementary. Preferably, (i) the ssON does not comprise at least one GGGG sequence and/or does not comprise at least one GGG sequence (eg TTAGGG); and/or (ii) the ssON comprises at least three different nucleotides selected from the group consisting of A, C, G and T, or at least four different nucleotides selected from the group consisting of A, C, G and T.

In a particularly preferred embodiment, the ssON of the second aspect of the invention is one wherein:

(a) the ssON comprises or consists of a polynucleotide having a sequence sharing at least 60% sequence identity (preferably 100% sequence identity) with a sequence of any one of SEQ ID NOs: 13-21 listed in Table 1, or a complementary sequence thereof;

(b) either (i) at least 90% of the internucleotide linkages in the ssON are phosphorothioate internucleotide linkages;

or (ii) the ssON comprises at least four phosphorothioate internucleotide linkages and at least four 2'-O-methyl modifications; and (c) the ssON does not contain any CpG motifs; and (d) the ssON does not target (eg bind specifically to) any specific viral (eg influenza such as influenza A) gene or polypeptide. Preferably, (i) the ssON does not comprise at least one GGGG sequence and/or does not comprise at least one GGG sequence (eg TTAGGG); and/or (ii) the ssON comprises at least three different nucleotides selected from the group consisting of A, C, G and T, or at least four different nucleotides selected from the group consisting of A, C, G and T.

In a particularly preferred embodiment, the ssON of the second aspect of the invention is one wherein:

(a) the ssON comprises or consists of a polynucleotide having a sequence sharing at least 60% sequence identity (preferably 100% sequence identity) with a sequence of any one of SEQ ID NOs: 13-21 listed in Table 1, or a complementary sequence thereof;

(b) either (i) at least 90% of the internucleotide linkages in the ssON are phosphorothioate internucleotide linkages; or (ii) the ssON comprises at least four phosphorothioate internucleotide linkages and at least four 2'-O-methyl modifications; and (c) the ssON does not contain any CpG motifs;

(d) the ssON does not target (eg bind specifically to) any specific viral (eg influenza such as influenza A) gene or polypeptide; and (e) (i) the ssON is non-complementary to any human mRNA and/or influenza gene and/or (ii) the ssON is not self-complementary. Preferably, (i) the ssON does not comprise at least one GGGG sequence and/or does not comprise at least one GGG sequence (eg TTAGGG); and/or (ii) the ssON comprises at least three different nucleotides selected from the group consisting of A, C, G and T, or at least four different nucleotides selected from the group consisting of A, C, G and T.

A third aspect of the invention provides an ssON according to the second aspect of the invention for use in medicine.

A fourth aspect of the invention provides a pharmaceutical composition comprising an ssON according to the second aspect of the invention, and a pharmaceutically acceptable carrier. The pharmaceutical composition is typically adapted for use in the treatment or prophylaxis of an infection caused by an influenza virus. By pharmaceutical composition we include the meaning of a pharmaceutically active compound that is admixed with a conventional pharmaceutical carrier and/or excipient (eg vehicles) and used in the form of aqueous solutions, tablets, capsules, and the like. Optionally, the pharmaceutical composition may contain other pharmaceutically acceptable components, such as buffers, surfactants, antioxidants, viscosity modifying agents, preservatives and the like.

A fifth aspect of the invention provides a composition comprising an ssON according to the second aspect of the invention, and an additional therapeutic agent. Suitable additional therapeutic agents include those described above in relation to the first aspect of the invention. For example, the additional therapeutic agent could be a further anti-viral agent. The composition of the fifth aspect of the invention may also be a pharmaceutical composition, further comprising a pharmaceutically acceptable carrier.

The inventors have also demonstrated that ssONs have utility in treating or preventing a disease or condition of the skin and/or subcutaneous tissue. Hence, a sixth aspect of the invention provides an ssON according to the second aspect of the invention, for use in treating or preventing a disease or condition of the skin and/or subcutaneous tissue.

It will be appreciated that this aspect of the invention includes the use of an ssON according to the second aspect of the invention in the manufacture of a medicament for treating or preventing a disease or condition of the skin and/or subcutaneous tissue.

Similarly, it will be appreciated that this aspect of the invention includes a method of preventing or treating a disease or condition of the skin and/or subcutaneous tissue, the method comprising administering a ssON according to the second aspect of the invention to the subject.

The term disease or condition of the skin and/or subcutaneous tissue includes the medical conditions coded in ICD-10 (International Statistical Classification of Diseases and Related Health Problems, 10threvision). Such conditions include e.g. infections of the skin and subcutaneous tissue (e.g. cellulitis); dermatitis and eczema (e.g. atopic dermatitis and/or pruritus); bullous disorders (e.g. pemphigus); papulosquamous disorders (e.g. psoriasis); urticaria and erythema; disorders of skin appendages (e.g. rosacea); or other disorders of the skin and subcutaneous tissue (e.g. lupus erythematosus). These examples are purely illustrative from each category and are not meant to limit the scope of the invention. In a preferred embodiment, the disease or condition of the skin and/or subcutaneous tissue comprises a medical disease or condition coded in ICD-10, Chapter XII, L20-L30 "Dermatitis and eczema", such as in particular L20 "Atopic dermatitis" and/or L29 "Pruritus". Thus, it is particularly preferred if the disease or condition is dermatitis and/or eczema, such as atopic dermatitis or pruritus.

It is appreciated that an infection may be associated with the disease or condition of the skin and/or subcutaneous tissue. For example, the infection may be cause by a disrupted skin barrier, the initial treatment or by changes in the immune system. In this case, it may be desirable to also administer to the subject a further therapeutic agent to treat the infection.

In one embodiment, the ssON is administered in combination with an additional therapeutic agent.

Thus, the invention provides an ssON according to the second aspect of the invention, for use in preventing or treating a disease or condition of the skin and/or subcutaneous tissue, wherein the subject is administered an additional therapeutic agent. It is appreciated that the ssON and the additional therapeutic agent need not be part of the same composition, but may be administered separately as discussed further below.

Similarly, the invention includes the use of an ssON according to the second aspect of the invention in the manufacture of a medicament for preventing or treating a disease or condition of the skin and/or subcutaneous tissue in a subject, wherein the subject is administered an additional therapeutic agent.

Likewise, the invention includes a method of preventing or treating a disease or condition of the skin and/or subcutaneous tissue in a subject, comprising administering to the subject an ssON according to the second aspect of the invention and an additional therapeutic agent.

In one embodiment, the ssON and additional therapeutic agent are administered substantially simultaneously to the subject In an alternative embodiment, the ssON and the additional therapeutic agent are administered sequentially to the subject. Thus, the individual may be one who has already been administered the ssON, and the additional therapeutic agent is subsequently administered to the subject. Alternatively, the subject may be one who has already been administered the additional therapeutic agent, and the ssON is subsequently administered to the individual.

Preferences for additional therapeutic agents include those described above in relation to the first aspect of the invention. Also, the additional therapeutic agent may be one that is known to be suitable to prevent or treat a disease or condition of the skin and/or subcutaneous tissue. The additional therapeutic agent may be an anti-inflammatory agent or an anti-pruritic agent. Examples of additional therapeutic agents include a calcineurin inhibitor, a corticosteroid, an anti-IL31 inhibitor, a PDE-4 inhibitor, an IL-4R antibody, an anti-IL13 antibody, an anti-IL22 antibody, an anti-IL12/23 antibody, SB011 (which cleaves GATA-3 mRNA), an agent to remove or suppress/inhibit the effects of IgE, a DP2 antagonist, a neurokinin-1 receptor antagonist, a topical non-steroidal anti-inflammatory reagents such as LE032731 and GSK2894512, Clonidine, Naltrexone, a 5-HT2B receptor antagonist, and/or an anti-histamine treatments A seventh aspect of the invention provides a method for identifying an ssON for use in the treatment or prevention of an influenza virus infection, the method comprising:

(a) providing a test ssON; and (b) assessing whether the test ssON inhibits endocytosis;

wherein a test ssON that inhibits endocytosis is an ssON that is useful in the treatment or prevention of an influenza virus infection.

It will be appreciated that the test ssON is preferably one that has many of the features of the ssON described above in relation to the first aspect of the invention.

For example, the length of the test ssON may be between 20 and 70 nucleotides, such as between 25 and 70 nucleotides. It is preferred if the length of the test ssON is at least 25 nucleotides.

Preferably, the length of the test ssON is between 25 and 70 nucleotides, such as between 25 and 60 nucleotides, 25 and 50 nucleotides, 25 and 40 nucleotides or 25 and 35 nucleotides.

Preferably, the length of the test ssON is between 28 and 70 nucleotides, such as between 28 and 60 nucleotides, 28 and 50 nucleotides, 28 and 40 nucleotides or 28 and 35 nucleotides.

In a particularly preferred embodiment, the length of the test ssON is between 25 and 40 nucleotides, or between 28 and 40 nucleotides. For example, the length of the test ssON may be between 29 and 38 nucleotides or between 30 and 36 nucleotides. The length of the test ssON may be at least 25, 26, 27, 28, 29, 30, 31, 32, 33, 34, 35, 36, 37, 38, 39 or 40 nucleotides, and/or the length of the test ssON may be no more than 40, 39, 38, 37, 36, 35, 34, 33, 32, 31, 30, 29, 28, 27, 26 or 25 nucleotides. Further preferred ranges of length include 30-70, such as 30-60, 30-50, 30-40 or 30-35 nucleotides.

It will be appreciated that the test ssON may be a variant or derivative of any of the ssONs of SEQ ID NOs: 1-24 shown in Table 1 below.

It is preferred that at least 50%, 60%, 70%, 80% or 90% of the internucleotide linkages in the test ssON are phosphorothioate internucleotide linkages, as described above. Preferably, 95% or more preferably 100% of the internucleotide linkages in the test ssON are PS internucleotide linkages. Thus the test ssON may have some internucleotide linkages (such as one, two, three, or more internucleotide linkages) which are PO linkages without sulfur, while the remaining linkages are PS linkages.

The test ssON of the second aspect of the invention may comprise 2'-O-methyl modifications, and/or other chemical modifications. Preferably, the test ssON comprises at least four phosphorothioate internucleotide linkages (eg at least 5 or 6 PS linkages) and at least four 2'-O-methyl modifications (eg at least 5 or 6 2'-O-methyl modifications).

Also, it is preferred if the test ssON does not contain a CpG motif.

It is preferred if the test ssON has a "sequence independent" mode of action, does not have antisense activity and is not complementary to a gene. More specifically, it is preferred if not more than 16 consecutive nucleotides in the ssON are complementary with any human mRNA sequence (eg human mRNA coding sequence) or virus (eg influenza such as influenza A) gene.

In an embodiment, the test ssON does not target (eg bind specifically to) any specific viral (eg influenza such as influenza A) gene or polypeptide.

In yet a further preferred embodiment, the test ssON is not self-complementary. It is desirable that the test ssON does not form any loop structures.

Preferably, the test ssON is a single-stranded oligodeoxynucleotide (ssODN), although it is appreciated that it may be a single-stranded RNA (ribonucleic acid) molecule as described above.

In an embodiment, the test ssON does not contain TTAGGG.

In an embodiment, the test ssON does not comprise at least one GGGG sequence and/or does not comprise at least one GGG sequence (eg TTAGGG).

It is preferred that the test ssON comprises at least three different nucleotides selected from the group consisting of A, C, G and T, or at least four different nucleotides selected from the group consisting of A, C, G and T. In this case, it will be appreciated that the test ssON is not composed of single repeats or dinucleotide repeats, such as repeats of the formula $A(x)$, $C(x)$, $G(x)$, $T(x)$, $AC(x)$, $AG(x)$, $AT(x)$, $CG(x)$, $CT(x)$, or $GT(x)$, wherein x is an integer.

Assessing whether the test ssON inhibits endocytosis may be carried out by any suitable method known in the art, including those described above in relation to the first aspect of the invention. For example, the methods may involve labelling components of the endocytic machinery of a host cell such as early endosomes, late endosomes or lysosomes, directly, and assessing the effect of the test ssON on the components of the endocytic machinery. The methods may involve measuring the internalisation of molecules that are known to rely on endocytosis for cell entry, and assessing the effect of the test ssON on such internalisation. The methods may involve measuring downstream signalling events that are known to rely on endocytosis for their activation, and assessing the effect of the test ssON on such downstream signalling events. Particular methods that may be used are described in more detail in the Examples.

It is appreciated that screening assays which are capable of high throughput operation are particularly preferred.

The assay is typically cell based.

The assay is conveniently conducted in vitro. For example, the assay may be performed on human monocyte-derived dendritic cells in vitro. Such an assay is described in more detail in the Examples below. Alternatively, the assay may be carried out in vivo.

It will be appreciated that if the test ssON reduces the level of endocytosis in a cell to a level less than the level of endocytosis in the cell in the absence of the inhibitor, the test ssON may be an ssON that is useful in preventing or treating an influenza virus infection (eg influenza virus A infection). For example, the test ssON may reduce the level of endocytosis to less than 95% or 90% of the level of endocytosis in the cell in the absence of the test ssON, such as less than 80%, 70%, 60%, 50%, 40%, 30%, 20% or 10% of the level of endocytosis in the cell in the absence of the test ssON. Preferably, the test ssON reduces the level of endocytosis in the cell to an undetectable level.

It is appreciated that the identification of a test ssON that inhibits endocytosis, may be an initial step in a drug screening pathway, and the identified ssON may be further selected e.g. for the ability to prevent or treat influenza infection. Thus, the method may further comprise the step of testing the test ssON in an influenza infection assay (eg an in vitro cell based assay) and/or testing the test ssON for efficacy in an animal model (eg mouse model) of an influenza infection. Suitable models are known in the art and an example is given in the Examples below. Thus the method may further comprise the step of assessing the viral load in a cell or animal that has been infected with an influenza virus.

It will be appreciated that in the method of the seventh aspect of the invention, the ssONs described above in relation to the first and second aspects of the invention may be used as positive controls, for example to assist in optimisation of the experimental setup.

The invention may comprise the further step of synthesising and/or purifying the identified test ssON. The invention may further comprise the step of formulating the test ssON into a pharmaceutically acceptable composition. ssONs may also be subjected to other tests, for example toxicology or metabolism tests, as is well known to those skilled in the art.

The invention includes a method for preparing an ssON that is useful in the treatment or prevention of an influenza virus infection, the method comprising identifying an ssON using the screening methods described above and synthesising, purifying and/or formulating the identified ssON.

The invention also includes a method of making a pharmaceutical composition comprising the step of mixing the ssON identified using the methods described above with a pharmaceutically acceptable carrier.

The listing or discussion in this specification of an apparently prior-published document should not necessarily be taken as an acknowledgement that the document is part of the state of the art or is common general knowledge.

Preferred, non-limiting examples which embody certain aspects of the invention will now be described, with reference to the following figures:

FIG. 1. Extracellular ssON inhibit CME and CDE, and spare MPC in human moDCs this needs updating to be understandable in black/white Human moDCs were treated for 45 min at +37° C. or +4° C. with endocytic uptake markers (Transferrin-red, Cholera toxin B-green, Dextran-blue and LDL-yellow) with or without addition of ssON 35 or ssON 35 alone (purple). Histograms show representative data from at least three donors. Dark coloured area (red, green, yellow, blue and purple) depict uptake of indicated molecules at +37° C. whereas addition of ssON is depicted with dashed line (light colour). Background, with experiment conducted at +4° C. is displayed as grey.

(A, B) 10 µM ssON 35 PO (MedON02) partly inhibited uptake of CME and CDE dependent uptake (Transferrin, Cholera toxin B).

(C, D) 0.5 µM ssON 35 PS (MedON01) completely inhibited uptake of CME and CDE dependent uptake (Transferrin, Cholera toxin B).

(E) 0.5 µM ssON 35 PS (MedON01) did not influence MPC (Dextran). Complete overlap dark and light blue.

(F) Fluorescently labelled ssON 35 PS had the same uptake at +37° C. and +4° C. Complete overlap dark and light purple.

(G, H) Quantitative analysis of Transferrin, Cholera toxin B uptake in the presence of 10 µM ssON 35 PO, 0.5 µM ssON 35 PS at +37° C. or +4° C.

(I) Quantitative analysis of fluorescently labelled ssON 35 PS uptake at +37° C. and +4° C.

(J) 0.5 µM ssON 35 PS (MedON-01) completely inhibited uptake of LDL.

Error bars are given in SEM. Non-parametric Mann-Whitney test was used to compare the data. P-value: not significant (n.s) P>0.05; *P≤5 0.05; P≤5 0.01; *P≤5 0.001.

Figure 2:
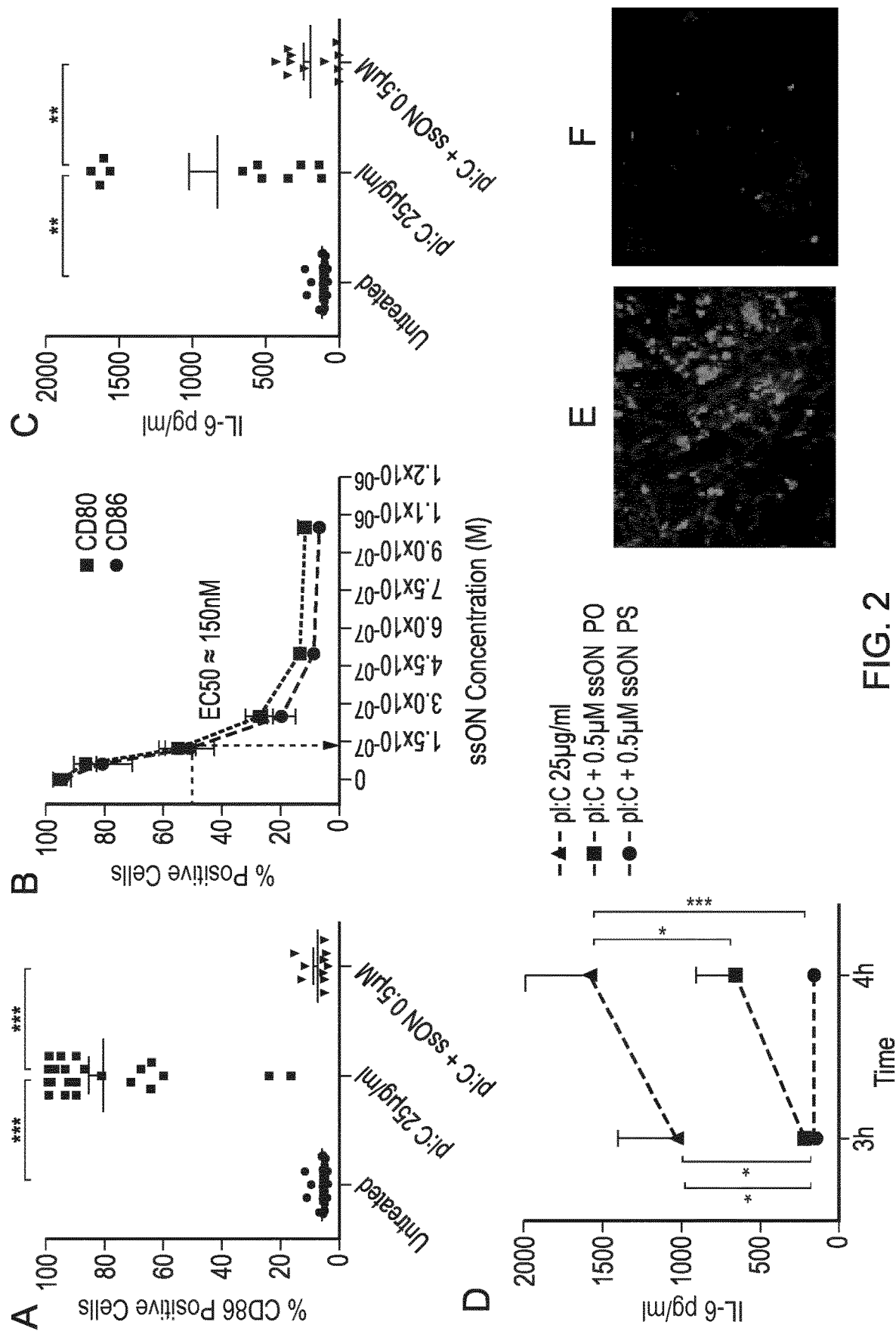
Figure 2:
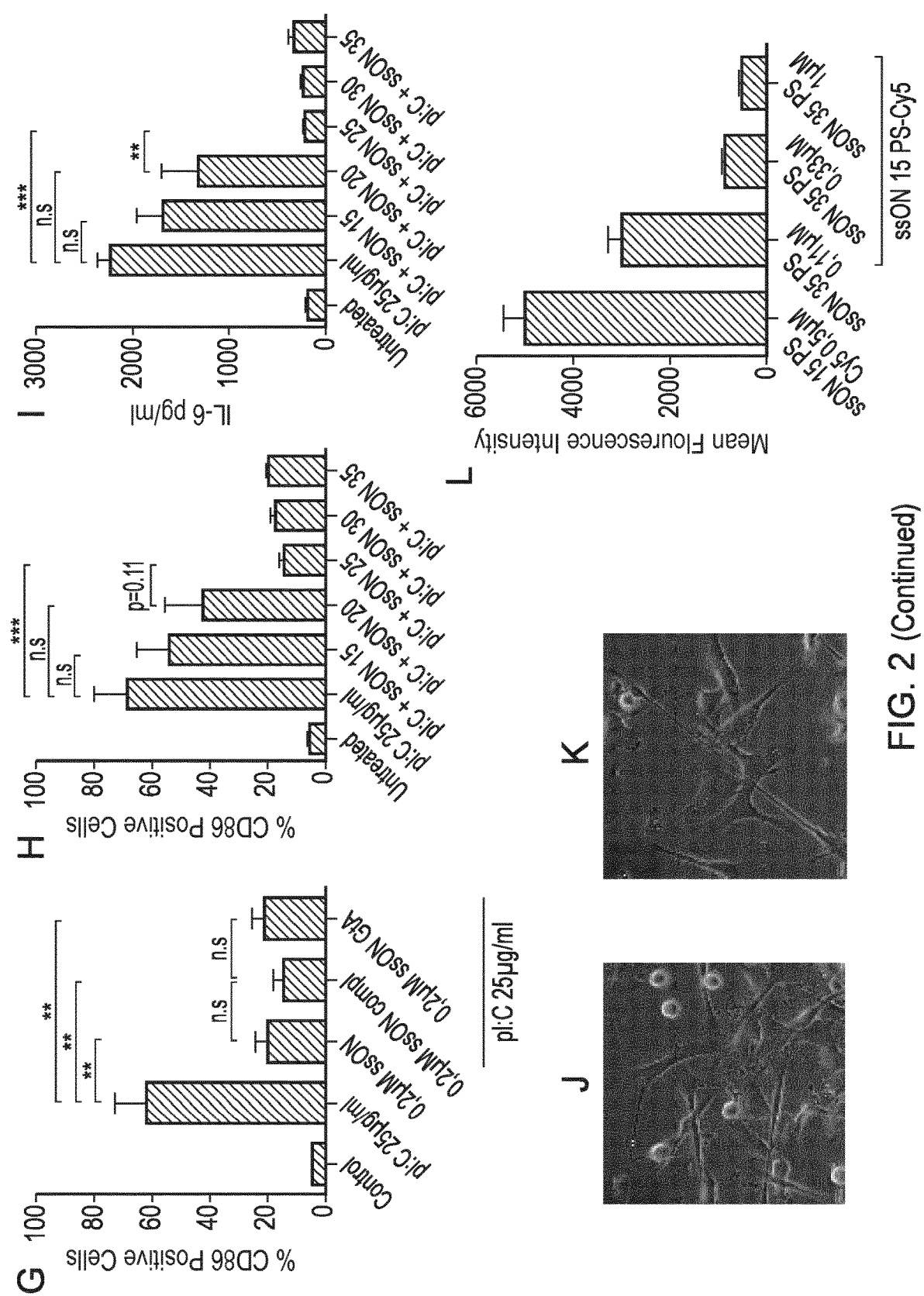

FIG. 2. SsON inhibited cellular uptake of polyI:C pI:C and decreased subsequent maturation of human moDC (A) 0.5 µM ssON 35 PS completely inhibited pI:C induced CD86 expression.

(B) The ssON 35 PS mediated inhibition of CD86 expression in pI:C exposed moDC was concentration dependent ($EC_{50}$ between 100-200 nM).

(C) SsON 35 PS completely inhibited pI:C induced IL-6 secretion.

(D) PS modification was not essential for the inhibitory effect.

(E) Uptake of fluorescent pI:C in moDCs (F) in the presence of 0.5 µM ssON 35 PS.

(G) The inhibition of pI:C induced CD86 expression was sequence independent (for sequences, see Table A).

(H, I) The inhibition of pI:C induced CD86 expression was dependent on the ssON length (ssON PS 15-35).

(J) Uptake of fluorescent ssON 15 PS in moDCs (K) in the presence 0.5 µM ssON 35 PS.

(L) Inhibition of fluorescent ssON 15 PS uptake was dependent on ssON 35 PS concentration. Error bars are given in SEM. Non-parametric Mann-Whitney test was used to compare the data. P-value: not significant (n.s) P>0.05; *P≤5 0.05; P≤5 0.01; *P≤5-0.00.

Figure 3:
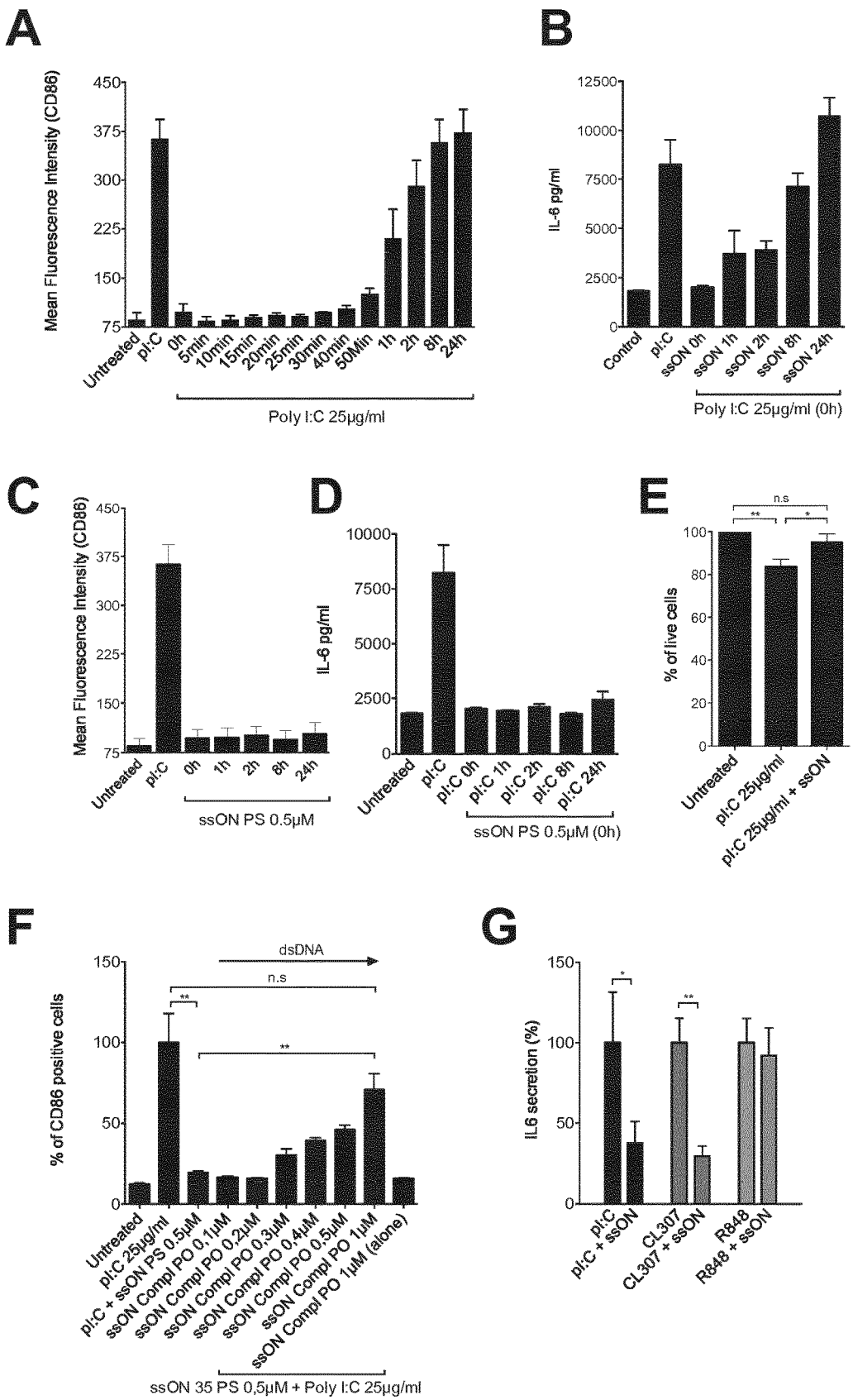

FIG. 3. Biokinetics of ssON mediated inhibition of TLR3 signalling (A, B) CD86 expression and IL-6 secretion from moDCs exposed to pI:C and subsequently challenged with ssON 35 PS at time-points from 5 min to 24 h.

(C, D) MoDCs treated in the opposite way, ssON 35 PS and subsequently challenged with pI:C.

(E) PI:C induced cell death in moDCs was reversed by the addition of 0.5 µM ssON 35 PS (n>25).

(F) Introduction of the complementary strand (ssON Compl PO) abolished the inhibitory effect on pI:C induced CD86 expression of 0.5 µM ssON 35 PS.

(G) SsON mediated inhibition of IL-6 secretion in PBMCs was limited to agonists that are taken up by endocytosis.

Error bars are given in SEM. Non-parametric Mann-Whitney test was used to compare the data. P-value: not significant (n.s) P>0.05; *P 5 0.05; P 5 0.01; *P 5 0.001.

Figure 4:
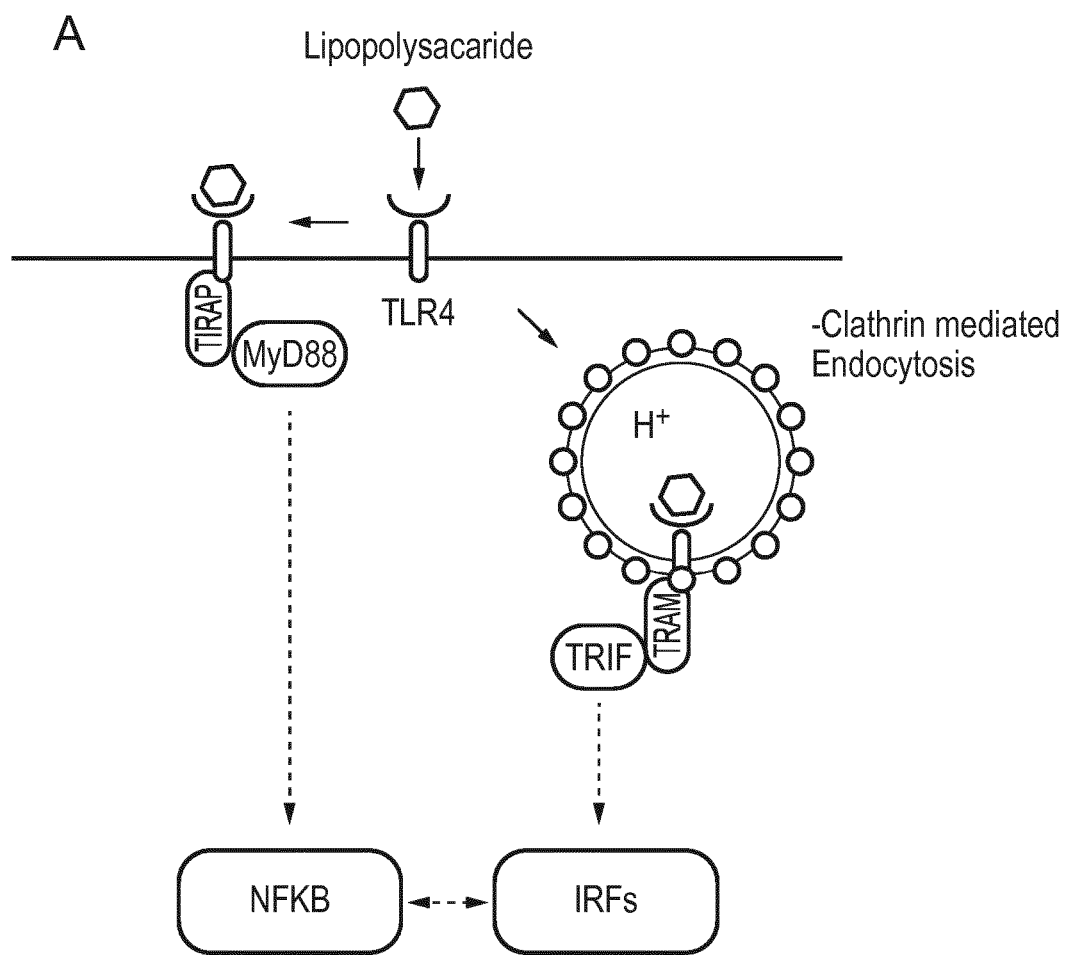
Figure 4:
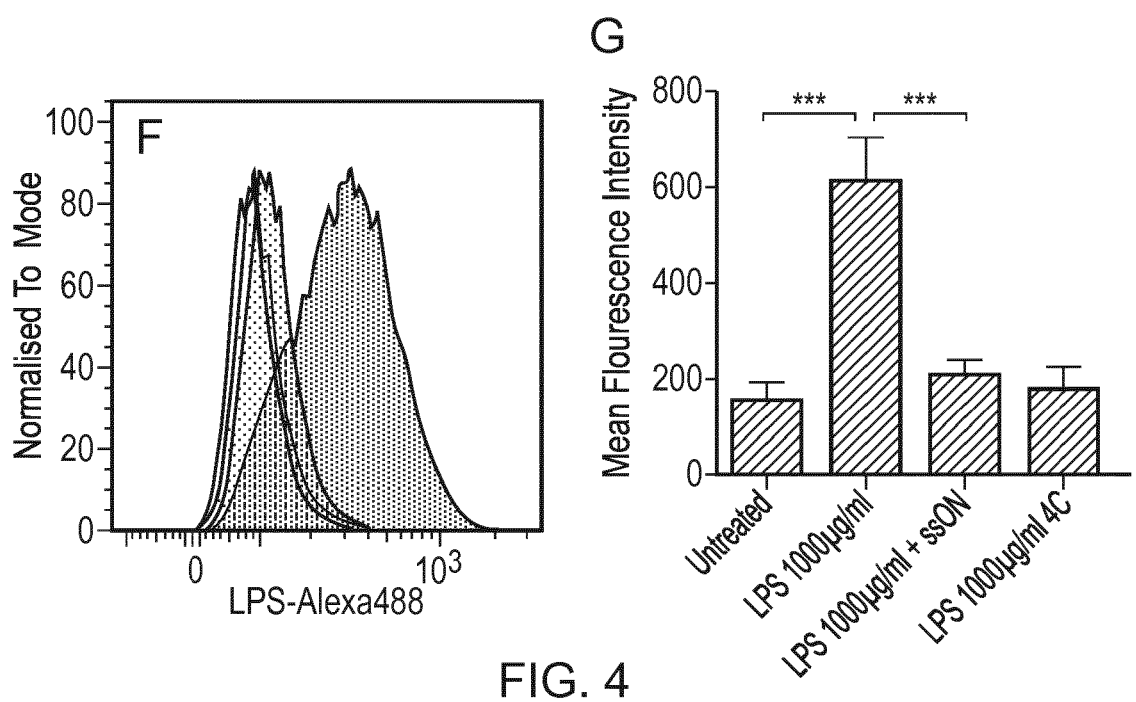
Figure 4:
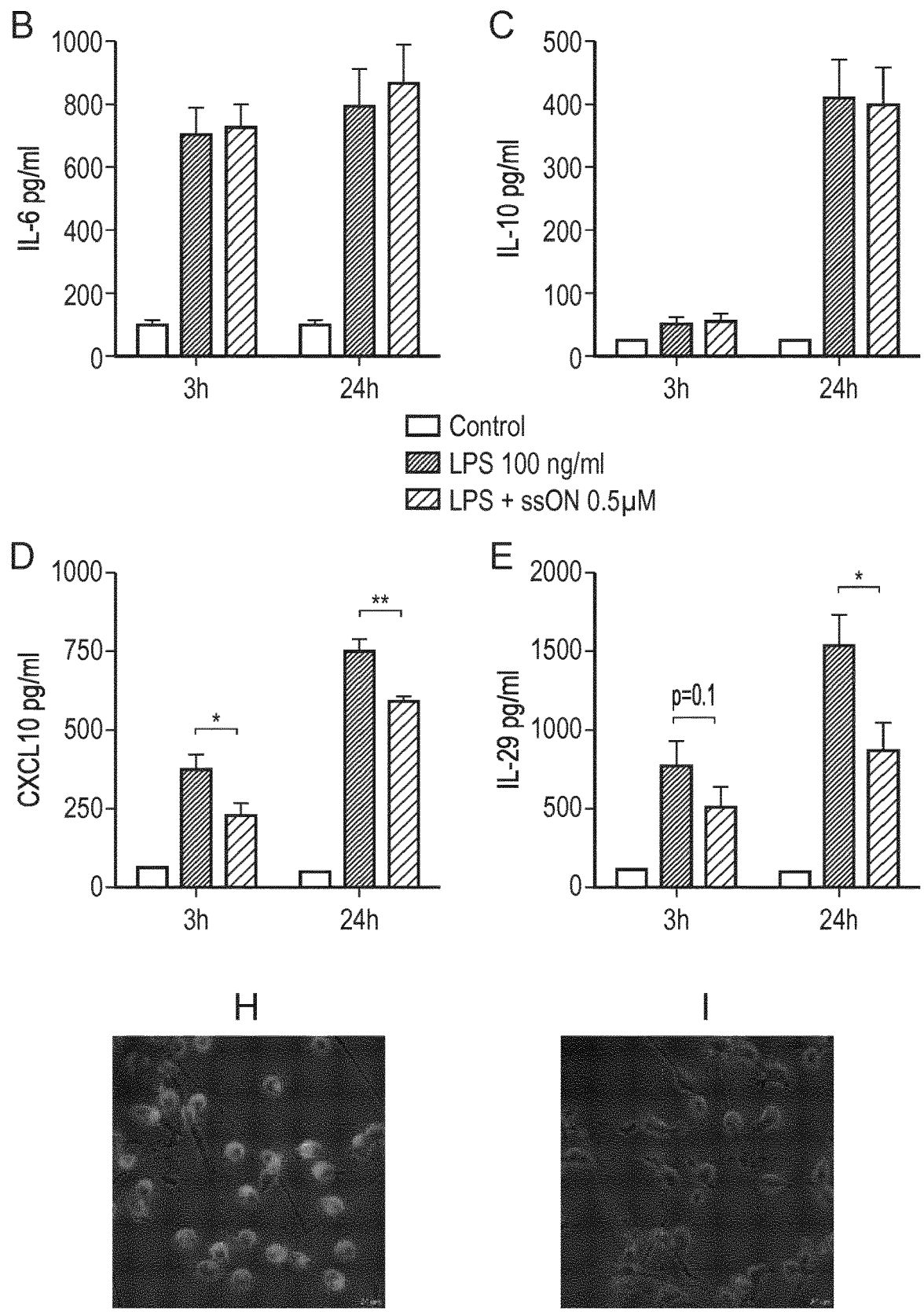

FIG. 4. Immunostimulation in moDCs exposed to the TLR4 agonist LPS with or without ssON 35 PS (A) Schematic view of TLR4 mediated cell signalling.

(B, C) 0.5 µM ssON 35 PS had no influence on secretion of cytokines/chemokines that are downstream of NFkB mediated signalling pathways (IL-6 and IL-10).

(D, E) 0.5 µM ssON 35 PS reduced secretion of cytokines/chemokines that are downstream of TRIF mediated signalling pathways (IL-29 and CXCL10).

(F) 0.5 µM ssON 35 PS inhibited uptake of fluorescently labelled LPS. Histogram shows representative data from at least three donors.

(G) Quantitative analysis of LPS uptake in the presence of 10 µM ssON 35 PO, 0.5 µM ssON 35 PS at +37° C. or +4° C.

(H) Uptake of fluorescent LPS in moDCs (I) in the presence of 0.5 µM ssON 35 PS.

Error bars are given in SEM. Non-parametric Mann-Whitney test was used to compare the data. P-value: not significant (n.s) P>0.05; *P 0.05; P≤0.01; *P≤0.001.

Figure 5:
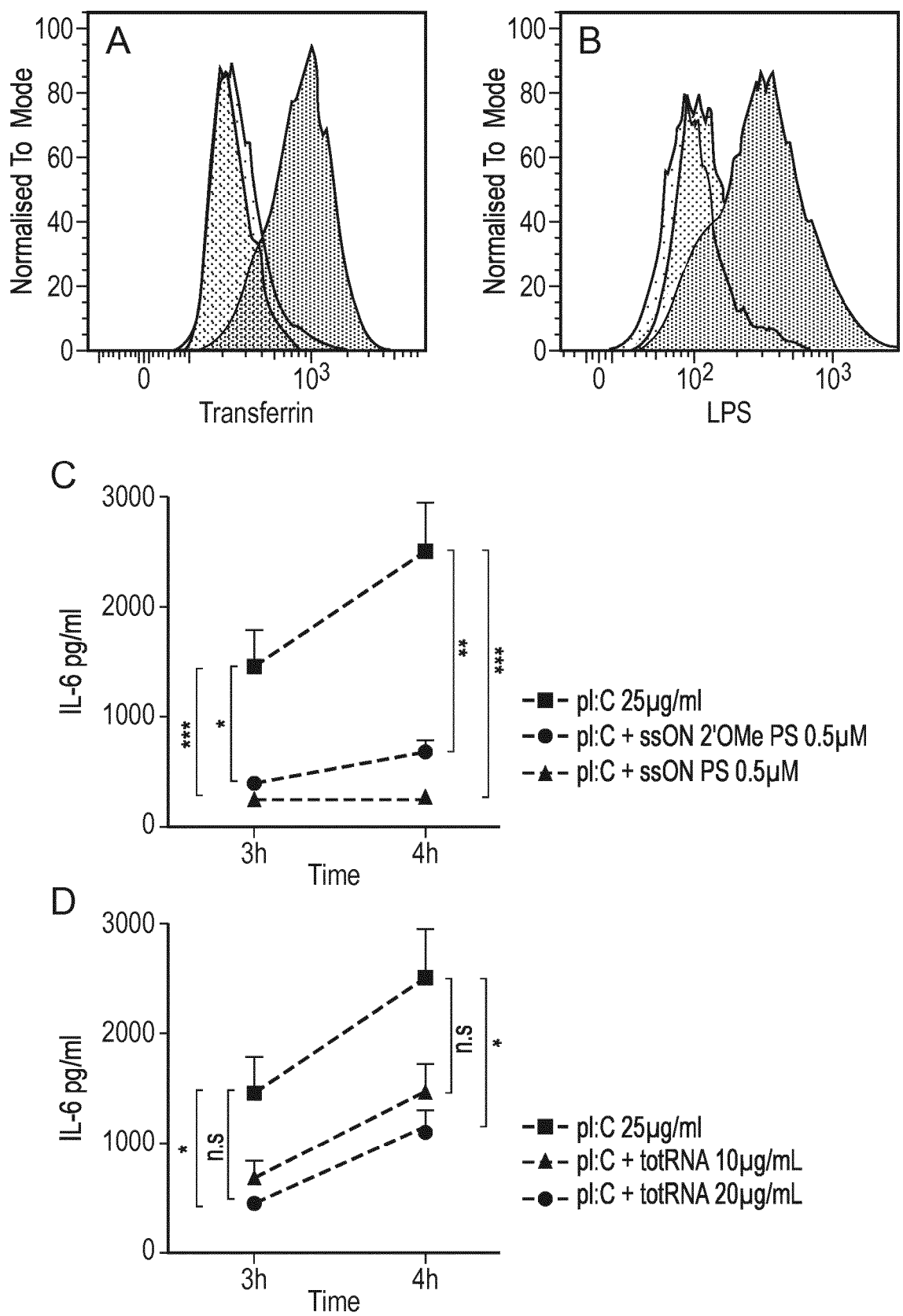

FIG. 5. RNA had similar ability as DNA to inhibit endocytic uptake in human moDCs Human moDCs were treated for 45 min at +37° C. or +4° C. with Transferrin (red) or LPS (orange) with or without addition of ssON 2'OMe PS (Table A). Histograms show representative data from at least three donors.

(A, B) 0.5 µM ssON 2'OMe PS completely inhibited uptake of fluorescently labelled Transferrin and LPS.

(C) SsON 2'OMe PS displayed the same efficacy as ssON 35 PS in blocking pI:C induced secretion of IL-6 from moDC.

(D) Total RNA inhibited pI:C induced IL-6 secretion from moDCs in a concentration dependent manner.

Error bars are given in SEM. Non-parametric Mann-Whitney test was used to compare the data. P-value: not significant (n.s) P>0.05; *P≤0.05; P≤0.01; *P≤0.001.

Figure 6:
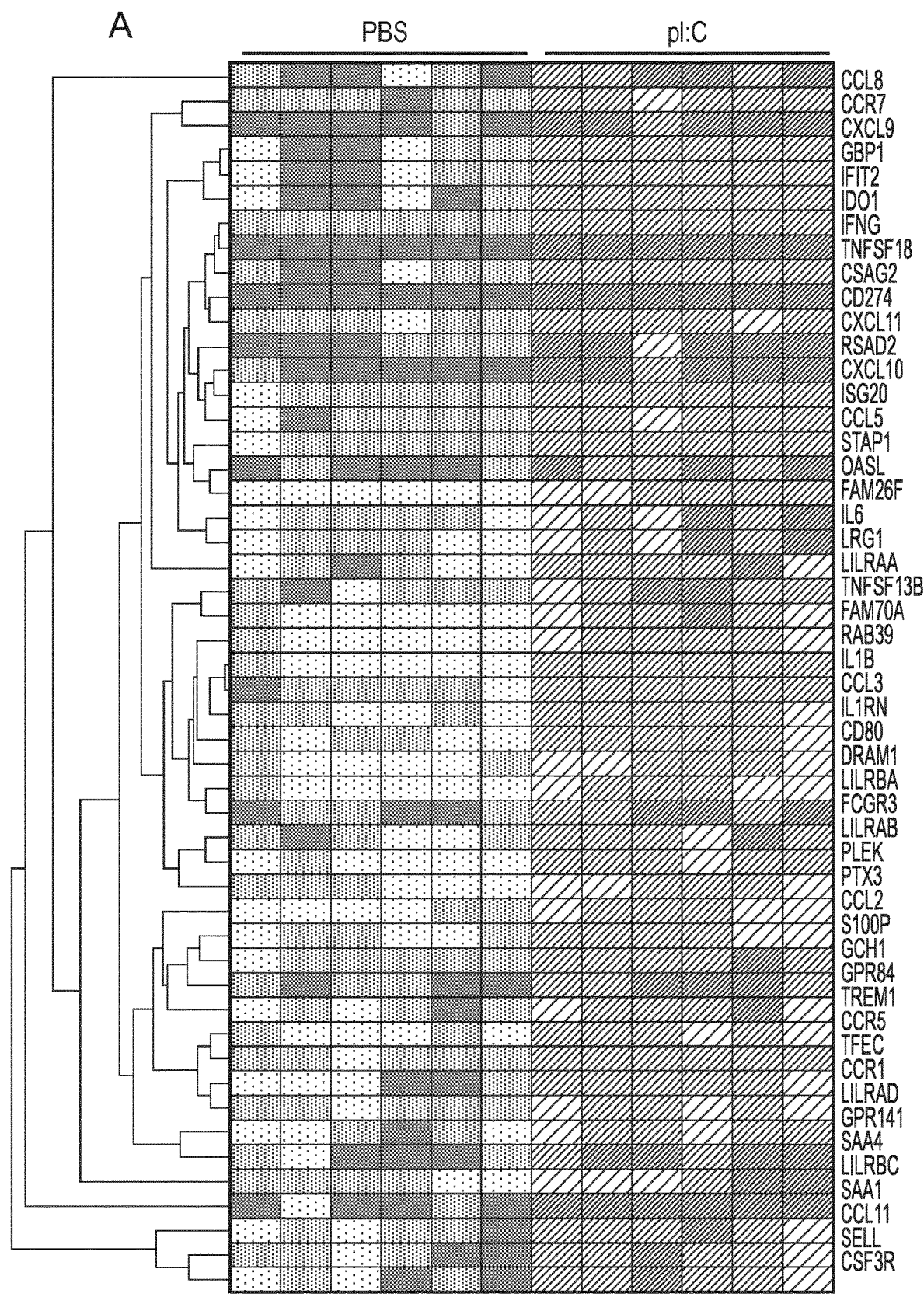
Figure 6:
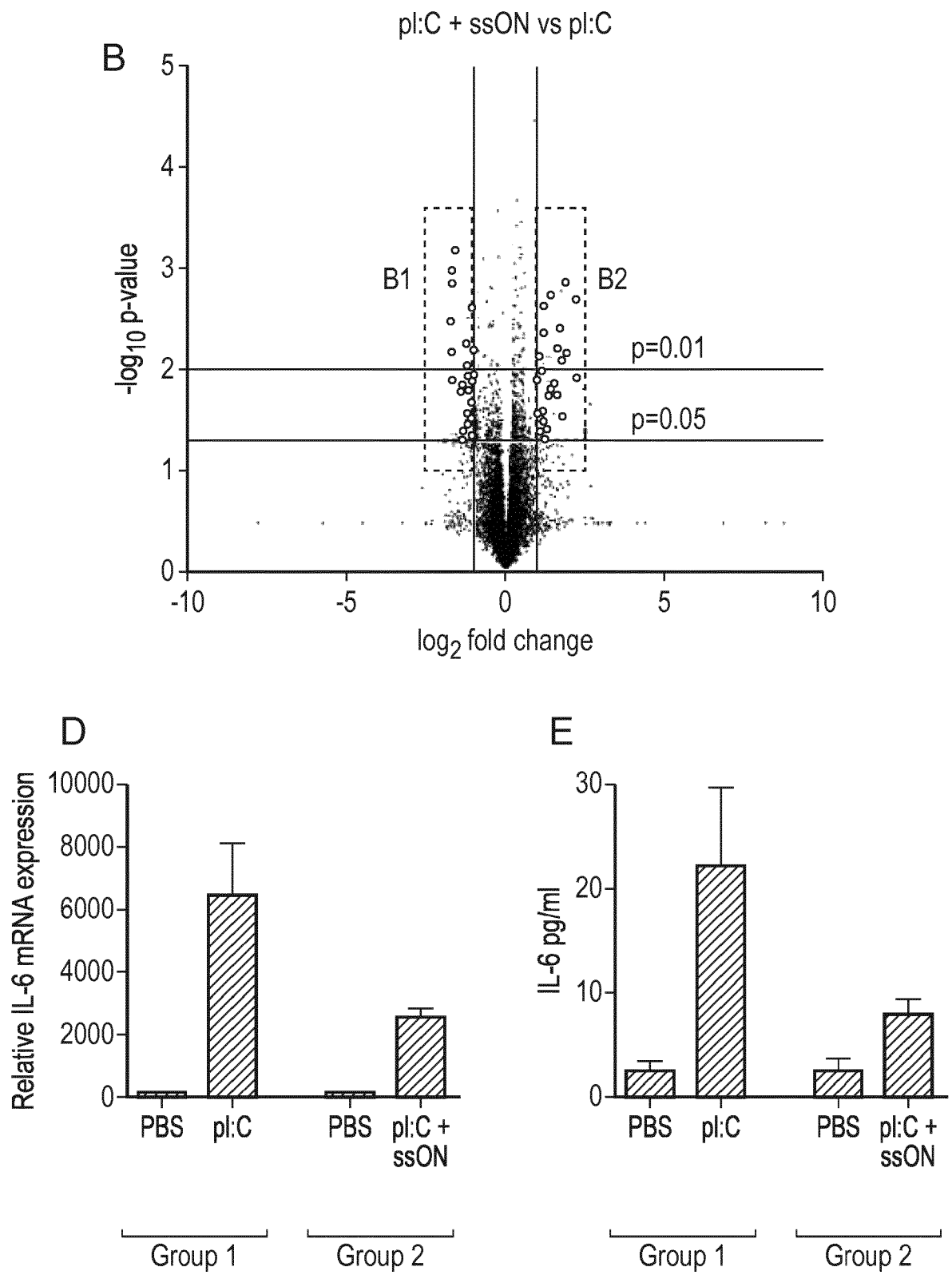
Figure 6:
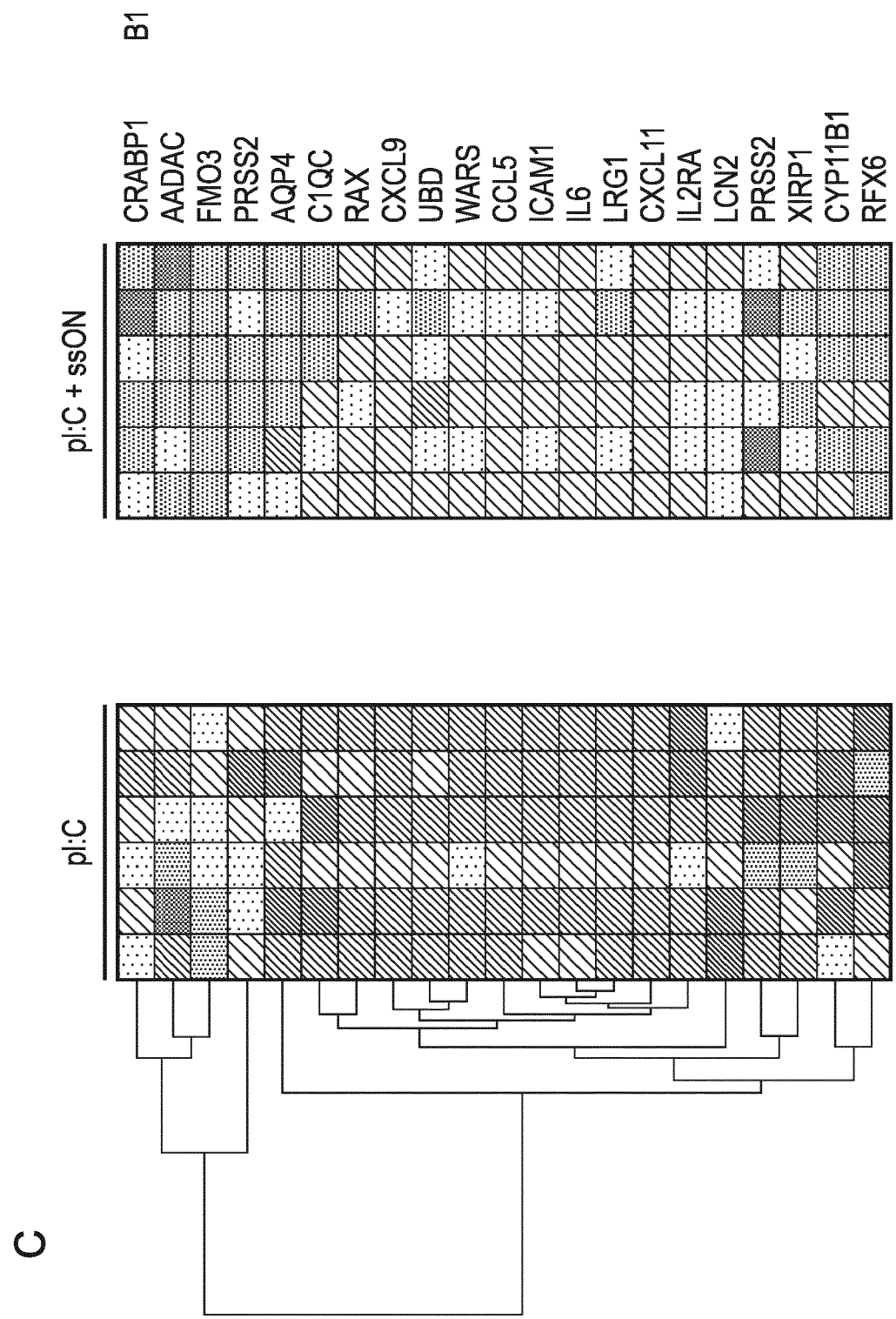
Figure 6:
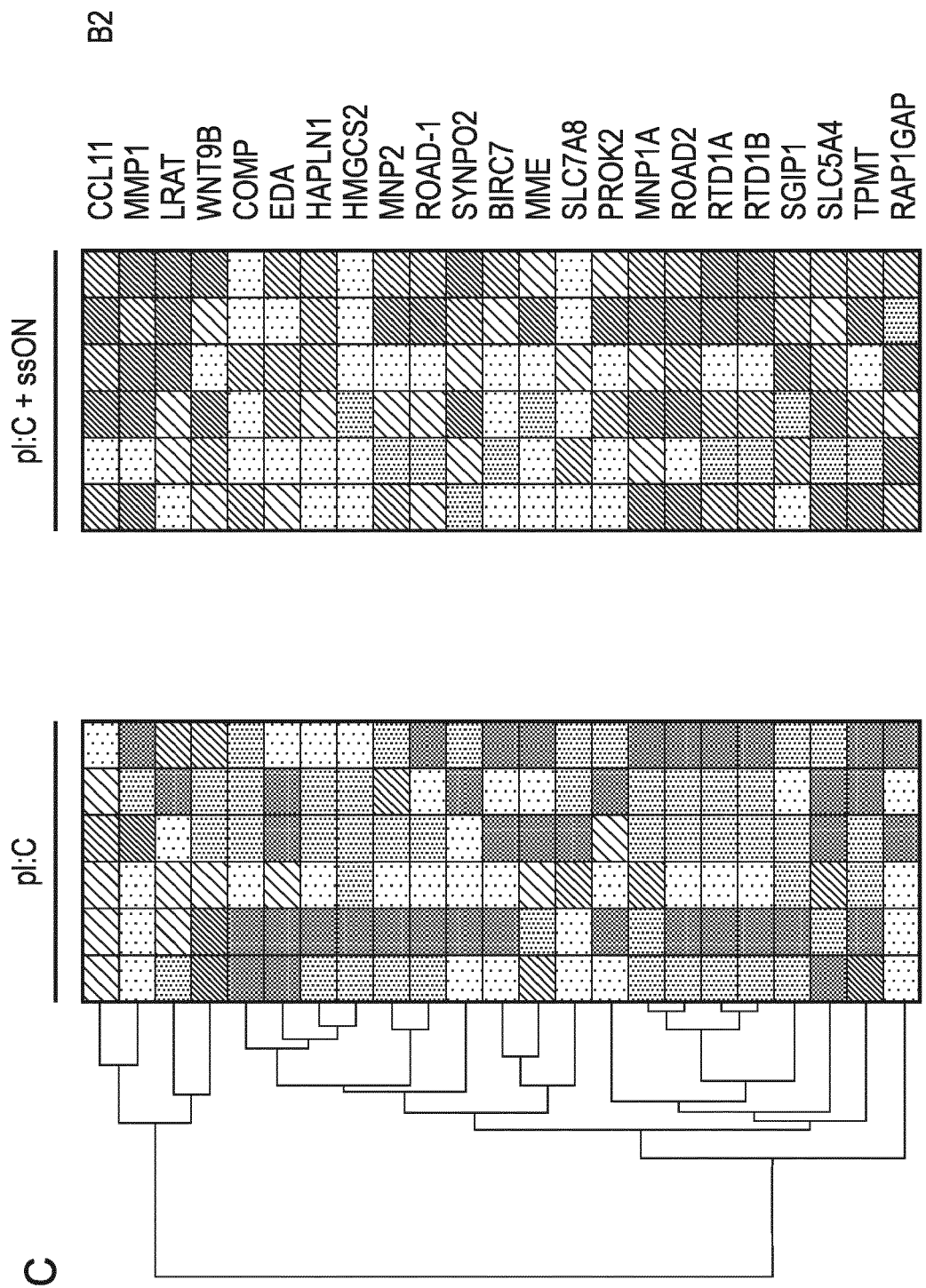

FIG. 6. The ssON 35 PS treatment dampened pI:C mediated inflammatory signatures locally in skin of macaques (A) Analysis of RNA expression in skin following injection with pI:C in the presence or absence of ssON 35 PS by microarrays.

(B) Volcano plot illustrating log 2 fold change and statistical significance across genes: genes with fold change>1 or <−1 and uncorrected p-value<0.05 highlighted in red (B1, B2).

(C) Clustering of genes showing the highest differential expression comparing pI:C treatment alone or in combination with ssON 35 PS, as determined by the Volcano plot (B1-top, B2-below).

Each row (in A, C,) represents a gene (probe); each column represents a sample.

The expression level for each gene was standardized by subtracting row mean expression and dividing by the standard deviation. This scaled expression value, (row z-score), is plotted in red-blue color scale with red indicating high expression and blue indicating low expression. Unsupervised hierarchical clustering of genes was based on Spearman correlation and are shown with means±SEM.

(D) Relative IL-6 mRNA expression values of individual macaque skin biopsies collected 24 hours post-stimulation.

(E) Concentrations of IL-6 protein present in supernatants of enzymatically digested dermis were measured by Bio-Plex technology.

Two skin biopsies (left and right side of the back) were obtained from each animal, where one of the biopsies were taken after injection of PBS and the other biopsy was taken from the site injected with the compound as indicated in the figures. Significant differences were assessed by non-parametric Kruskal-Wallis test and Dunn's post-test (* P<0.05,  P<0.01 and * P<0.001). Different treatment groups were compared using nonparametric Mann-Whitney unpaired test, as indicated (dash arrows).

Figure 7:
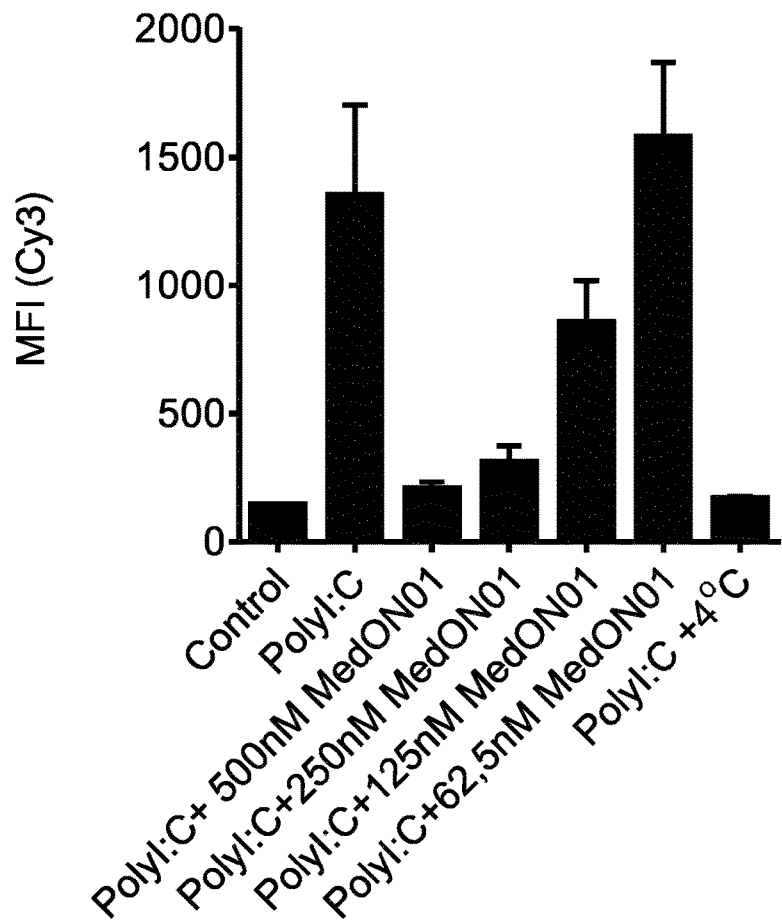

FIG. 7. MedON01 inhibits the uptake of poly (I:C) in human moDCs in a dose-dependent way.

Human moDCs were treated for 45 min at +37° C. or +4° C. with fluorescently labelled PolyI:C-Cy3 with or without addition of MedON01 (concentrations range 500-62.5 nM). Uptake was quantified by flow cytometry (MFI). Quantitative analysis of PolyI:C uptake in the presence of 500-62.5 nM MedON01 at +37° C., control PolyI:C alone at +4° C. (baseline negative control) or positive control PolyI:C alone at 37° C.

Figure 8:
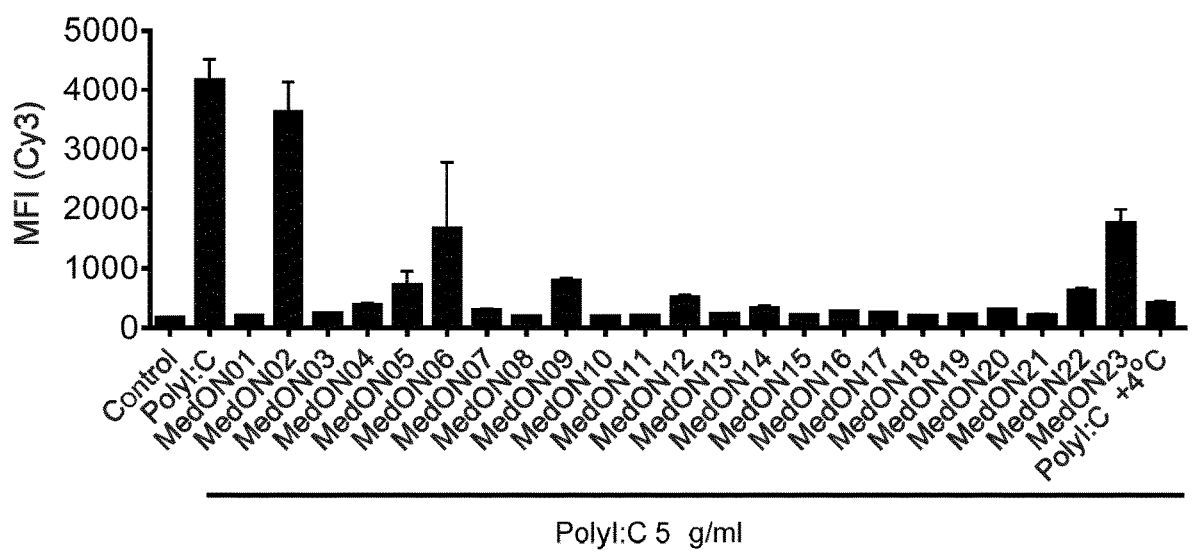

FIG. 8. Capacity to inhibit uptake of poly(I:C) is sequence independent Human moDCs were treated for 45 min at +37° C. or +4° C. with fluorescently labelled PolyI:C-Cy3 with or without addition of MedON01-23 (concentration 500 nM). Uptake was quantified by flow cytometry (MFI). Quantitative analysis of PolyI:C uptake in the presence of 500 nM MedONs01-23 at +37° C., control PolyI:C alone at +4° C. (baseline negative control) or positive control PolyI:C alone at 37° C.

Figure 9:
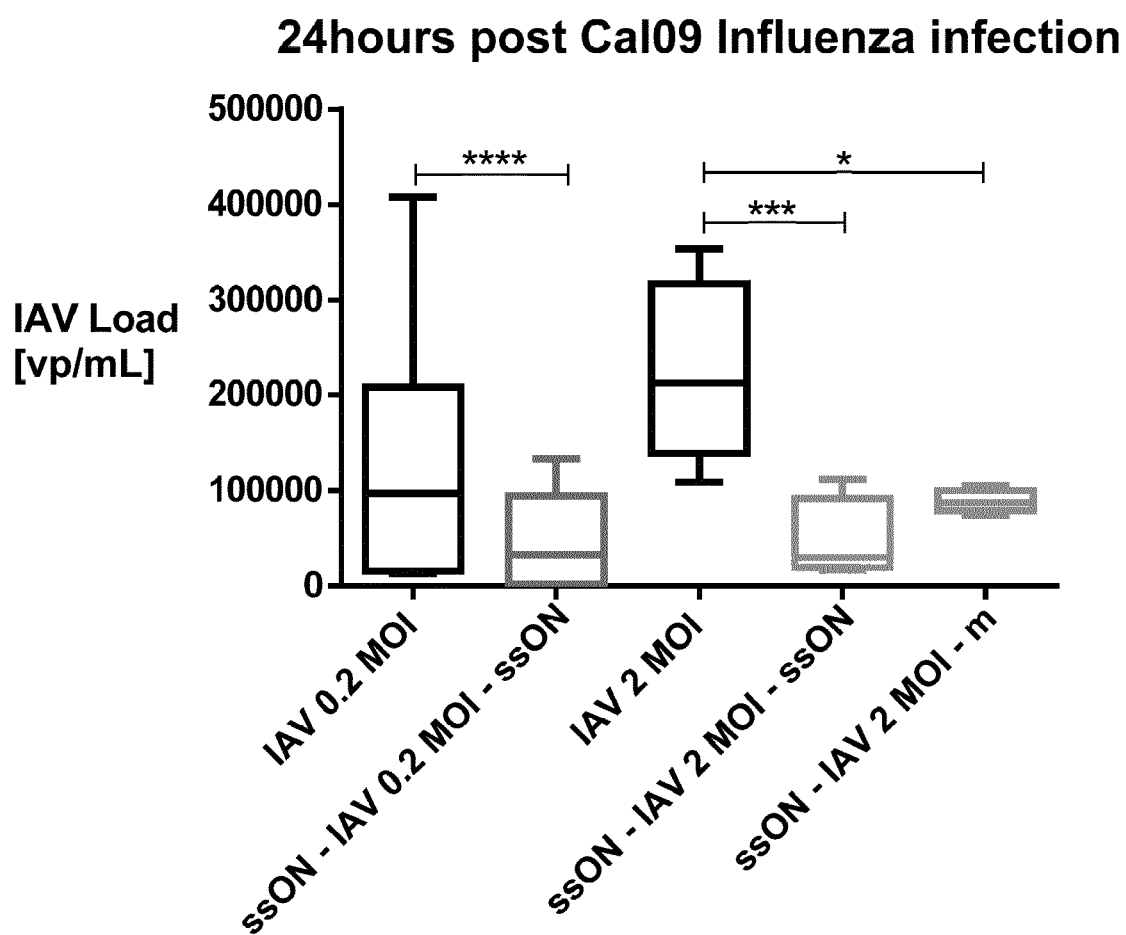

FIG. 9. Inhibition of influenza A by pre-treatment with MedON-01

Human monocyte derived DCs were infected in vitro with Influenza H1N1 Cal2009 (IAV) using MOI 0.2 or MOI 2. MoDC were either untreated or pre-treated with MedON-01 (0.5 µM) for 2 hours before infection. Infection with IAV was then carried out during another 2 hours. Cells were washed and incubated for 24 hours either with MedON-01 added again or not (m=medium). The viral load in the culture supernatants were quantified by real time PCR. Data were obtained in four independent experiments using six different donors analyzed in triplicate. Statistical calculations were made using non-parametric paired Wilcoxon text.

Figure 10:
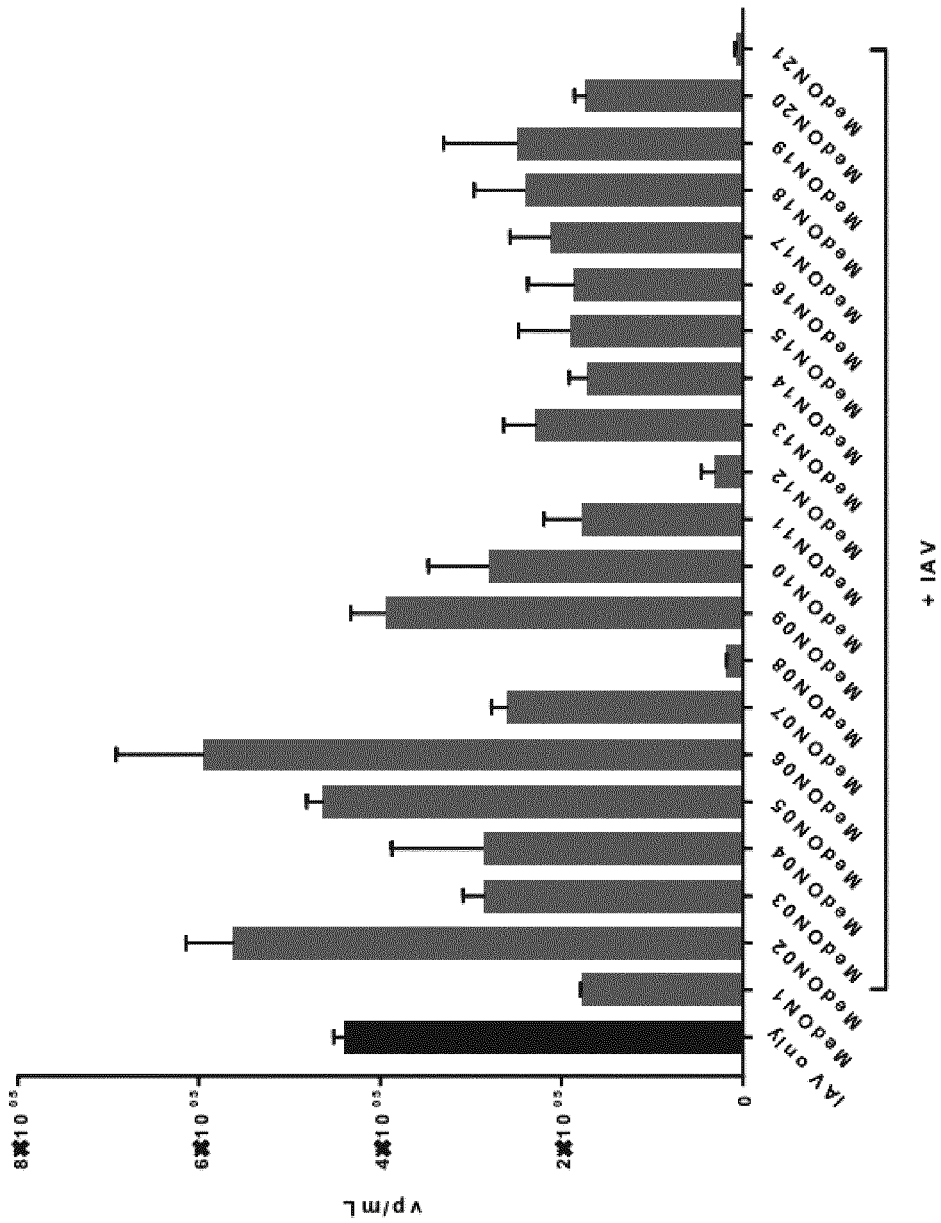

FIG. 10. Length requirement and chemical modification requirements for inhibition of influenza A infection.

Human monocyte derived DCs were infected in vitro with Influenza H1N1 Cal2009 (IAV) using MOI 1. MoDC were either untreated or pre-treated with MedON's 01-21 shown as SEQ ID Table 1 (1 µM) for 2 hours before infection. Infection with IAV was then carried out during another 2 hours. Cells were washed and incubated for 24 hours either with MedON's added again or not (m=medium). The viral load in the culture supernatants were quantified by real time PCR. Data were obtained i using two different donors analyzed in triplicate.

Figure 11:
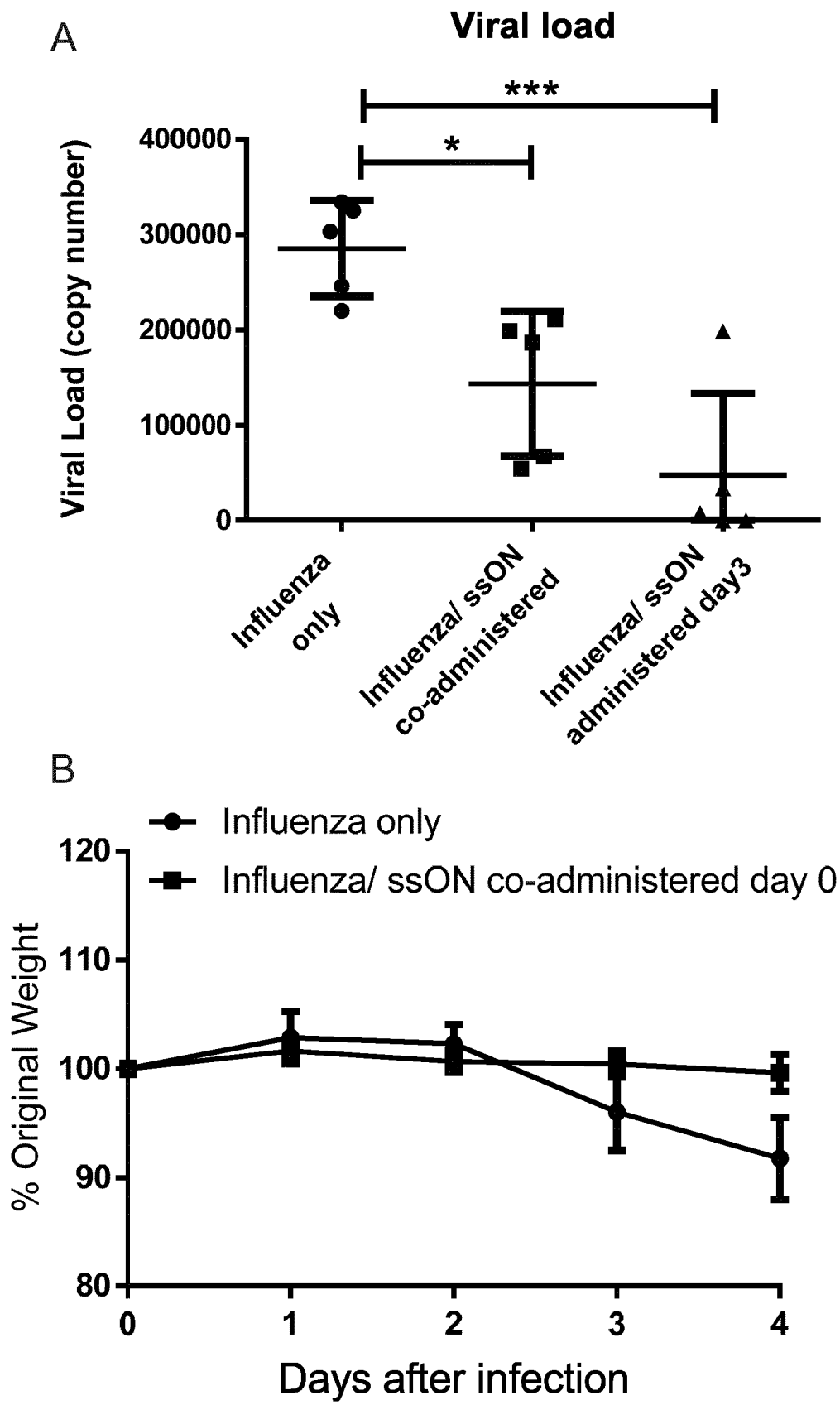

FIG. 11. Inhibition of influenza A viral load by MedON-01 treatment in vivo.

Balb/c mice were infected intranasal with Influenza H1N1 (Cal09). One group were untreated (FIG. 11A; circles), a second group received 25 µg of ssON (MedON01 SEQ ID No 1 Table 1) intranasal at the same time as the viral challenge (FIG. 11A; squares) and a third group received an intranasal treatment of 25 µg ssON day 3 (FIG. 11A; triangles). The mice were sacrificed day 4 after infection and the viral load was measured in the lungs. Statistical calculations were made using 1-way ANOVA. The untreated mice had a marked loss of weight at day 3 (FIG. 11 B circles) while the mice that received the prophylactic treatment with MedON-01 were able to maintain their weight (FIG. 11B; squares).

Figure 12:
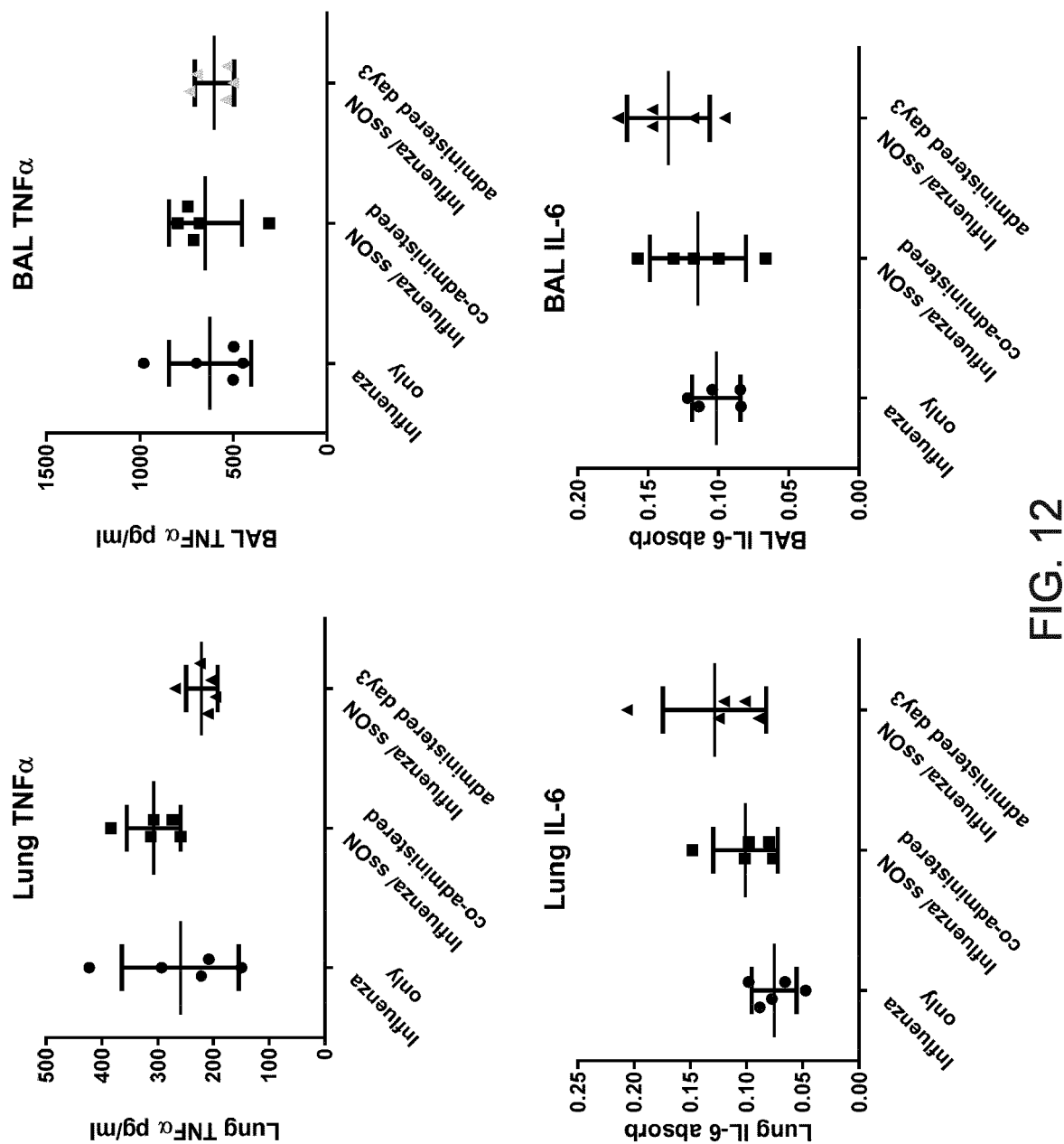

FIG. 12. TNF-alpha and IL-6 production in MedON-01 treated influenza A infected mice.

Balb/c mice were infected intranasally with Influenza H1N1 (Cal09). One group were untreated (FIG. 12; circles). The second group received 25 µg of ssON (MedON01) intranasally at the same time as the viral challenge (FIG. 12; squares). The third group received an intranasal treatment of 25 µg MedON-01on day 3 (FIG. 12; triangles). The mice were sacrificed day 4 after infection. The levels of TNF-α and IL-6 released from lung cells (LUNG) or present in the bronchoalveolar lavage (BAL) was measured by ELISA. Statistical calculations were made using 1-way ANOVA.

Figure 13:
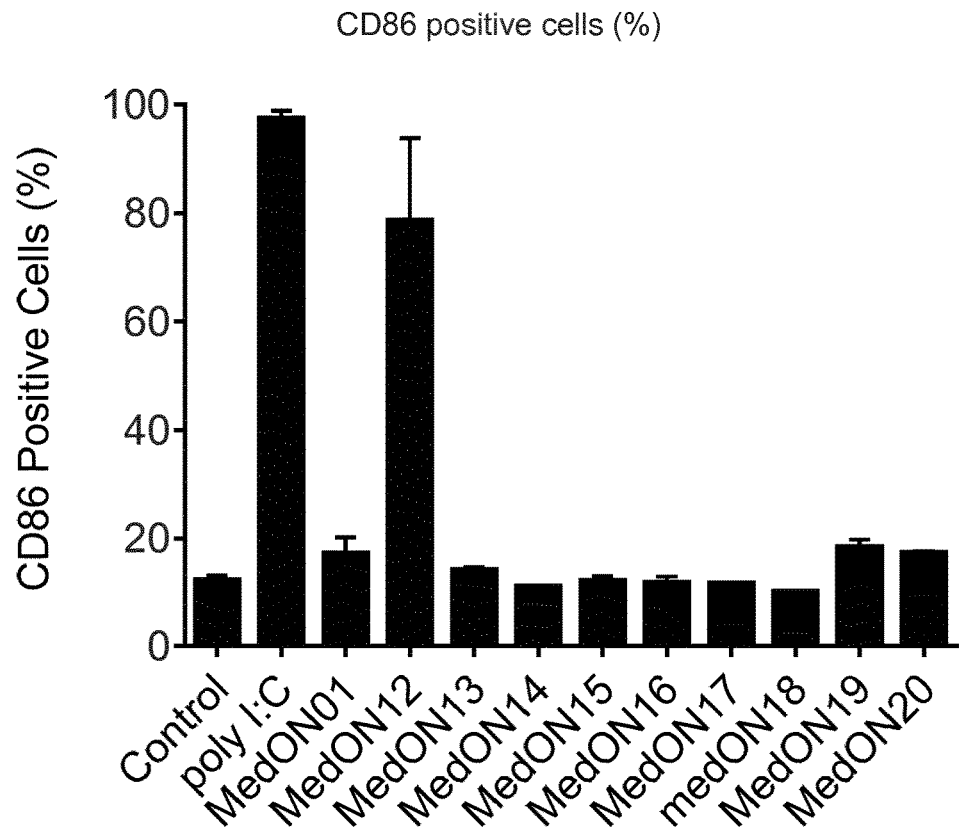

FIG. 13. Effect of ssONs on secretion of IL-6 by MoDCs.

MoDCs were treated with the TLR3 agonist poly I:C (25 µg/ml) in the absence or presence of 0.5 µM MedONs and incubated at +37° C. 24 h post treatments, the supernatant was collected and assessed for secretion of the pro-inflammatory cytokine IL-6 by using ELISA. MedON-01 and MedON-13-20 are able to inhibit poly I:C mediated induction of IL-6.

Figure 14:
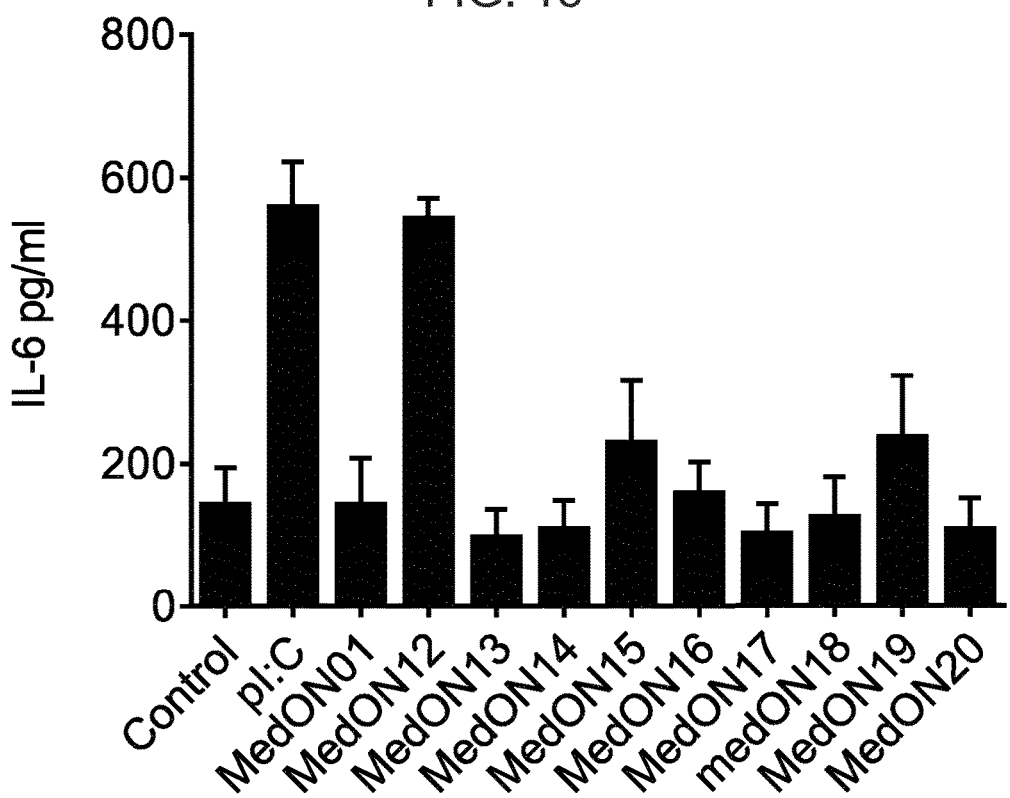

FIG. 14. Effect of ssONs on expression of CD86.

MoDCs were treated with the TLR3 agonist poly I:C (25 µg/ml) in the absence or presence of 0.5 µM MedONs and incubated at +37° C. 48 h post treatments, the cells were harvested and stained for immuno-maturation marker CD86. Surface expression of CD86 was quantified by flow cytometry. MedON-01 and MedON-13-20 are able to inhibit poly I:C mediated immune-maturation.

Figure 15:
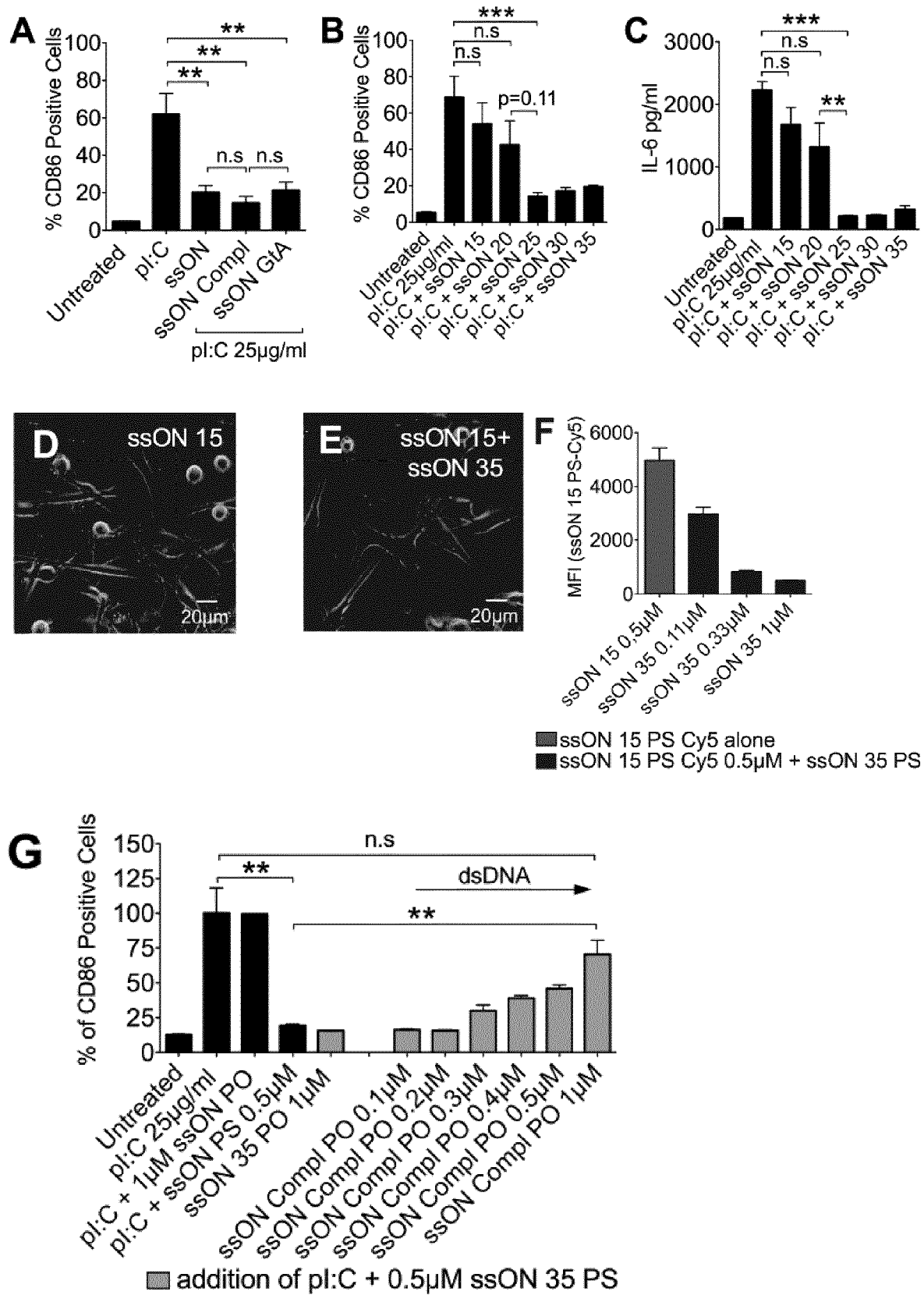

FIG. 15. SsON, but not dsDNA, of at least 20-25 bases inhibit TLR3 activation.

(A) The inhibition of pI:C-induced CD86 expression (48 h) in moDC was not dependent on a canonical sequence (for sequences, see Table 2).

(B, C) The inhibition of pI:C-induced CD86 expression (48 h) (B) and IL-6 production (24 h) (C) in moDC was dependent on the ssON length (ssON PS 15-35).

(D) Uptake of fluorescent ssON-color Cy5 15 PS in moDC (E) in the presence 0.5 µM ssON 35 PS.

(F) Inhibition of fluorescent ssON 15 PS uptake was dependent on ssON 35 PS concentration.

(G) Introduction of the complementary strand (ssON Compl PO) abolished the inhibitory effect on pI:C-induced CD86 expression (48 h) of 0.5 µM ssON 35 PS.

All data are from at least three donors in duplicate. Error bars are given in SEM. Nonparametric Mann-Whitney test was used to compare the data. P-value: not significant (n.s) P>0.05; *P≤0.05; P≤0.01; *P≤5 0.001.

Figure 16:
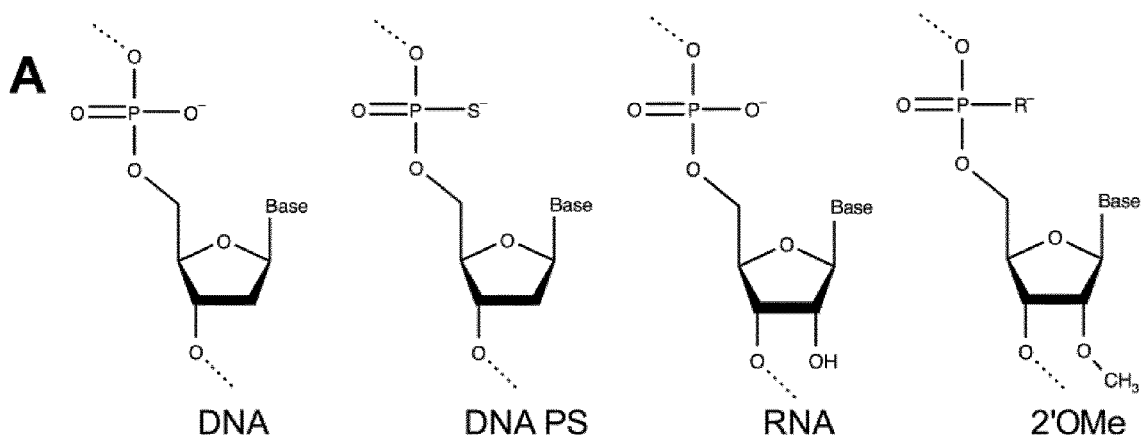
Figure 16:
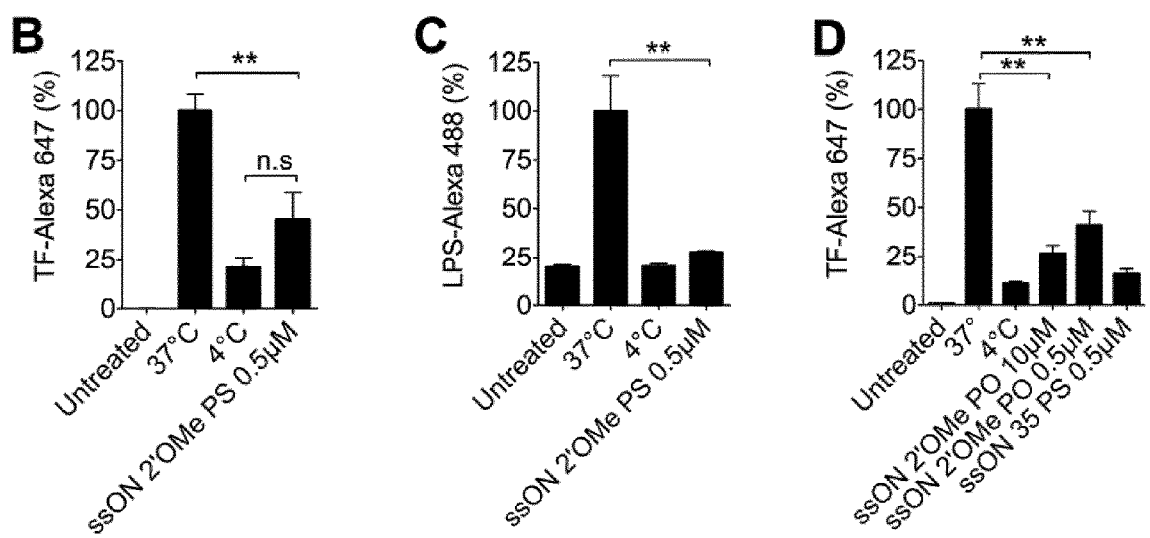
Figure 16:
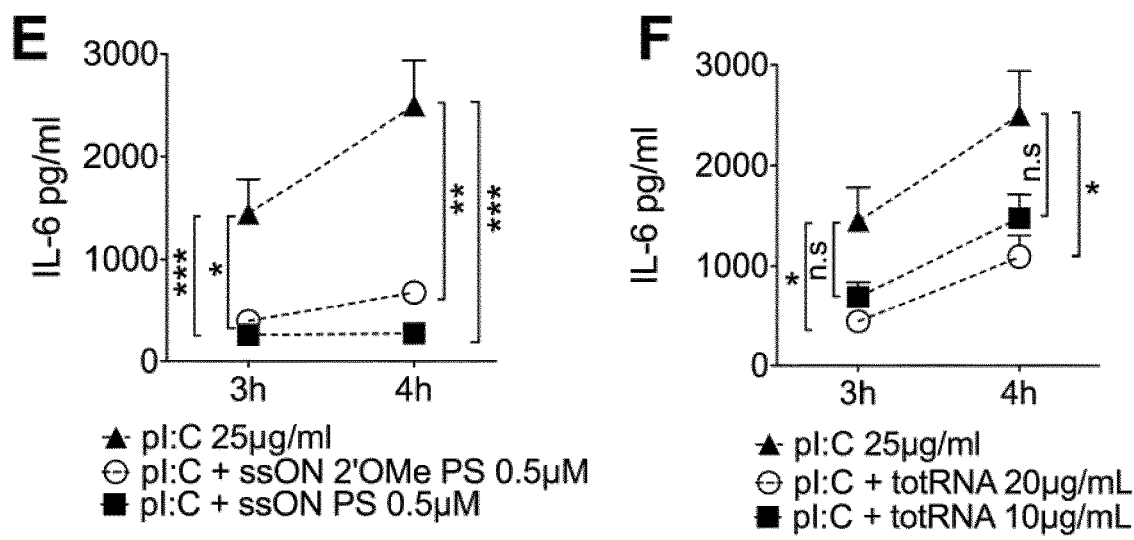

FIG. 16. SsRNA display similar ability as ssDNA to inhibit endocytic uptake in human moDC.

Human moDC were treated for 45 min at +37° C. or +4° C. with TF (Alexa 647) or LPS (Alexa 488) with or without addition of ssON 2'OMe RNA PS (Table 2).

(A) Structures of repeating units of oligonucleotides and oligonucleotide analogues included in this study.

(B, C) 0.5 µM ssON 2'OMe RNA PS inhibited uptake of fluorescently labelled TF and LPS.

(D) SsON 2'OMe RNA with a native PO backbone is able to block TF uptake in moDC.

(E) SsON 2'OMe RNA PS displayed the same efficacy as ssON 35 DNA PS in blocking pI:C-induced secretion of IL-6 from moDC.

(F) Total RNA inhibited pI:C-induced IL-6 secretion from moDC in a concentration dependent manner.

All data are from at least three donors in duplicate. Error bars are given in SEM. Nonparametric Mann-Whitney test was used to compare the data. P-value: not significant (n.s) P>0.05; *P≤0.05; P≤0.01; *P≤0.001.

Figure 17:
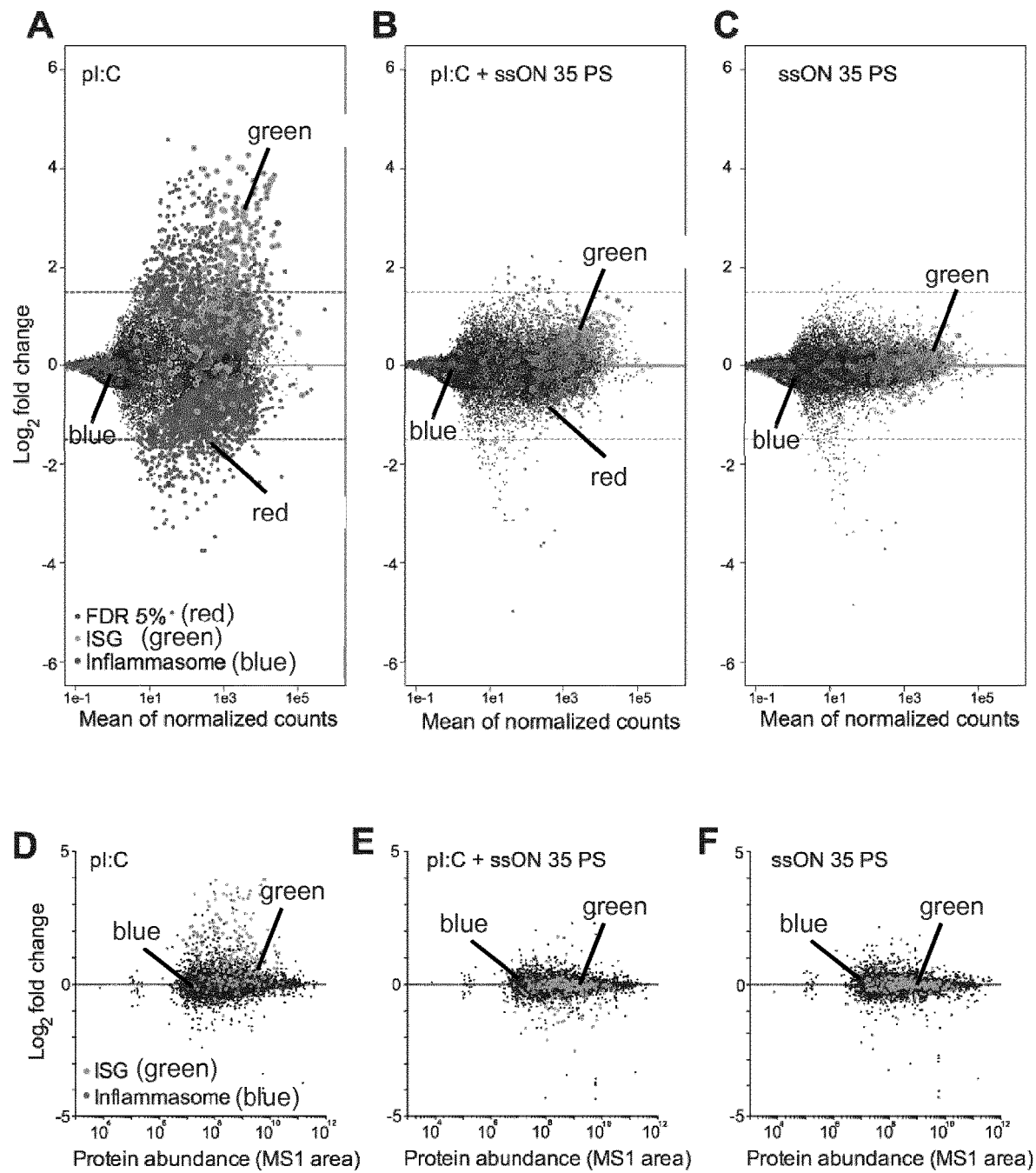

FIG. 17. SsON 35 PS inhibits pI:C induced changes in the transcriptome and proteome profile in moDC Colored circles mark genes included in specific categories (green=ISGs, blue=inflammasome related).

(A-C) RNA-seq data from moDC 24 h post treatment (3 donors). MA-plots log 2 fold changes adjusted p-values below 0.05 in red. (A) PI:C treatment vs non-treated cells shows high upregulation of ISGs. (B) Combined treatment with pI:C and ssON 35 PS (0.5 µM) vs nontreated cells show minor differences. (C) SsON 35 PS treatment (0.5 µM) vs non-treated cells show minor differences.

(D-F) Whole cell proteomic data from moDC 24 h post treatment (3 donors). MA-plots of whole cell proteomic data (protein log intensity ratio versus average intensity). (D) PI:C treatment vs non-treated cells show high upregulation of ISGs. (E) Combined treatment with pI:C and ssON 35 PS (0.5 µM) vs non-treated cells show minor differences. (F) SsON 35 PS treatment (0.5 µM) vs non-treated cells show minor differences.

Figure 18:
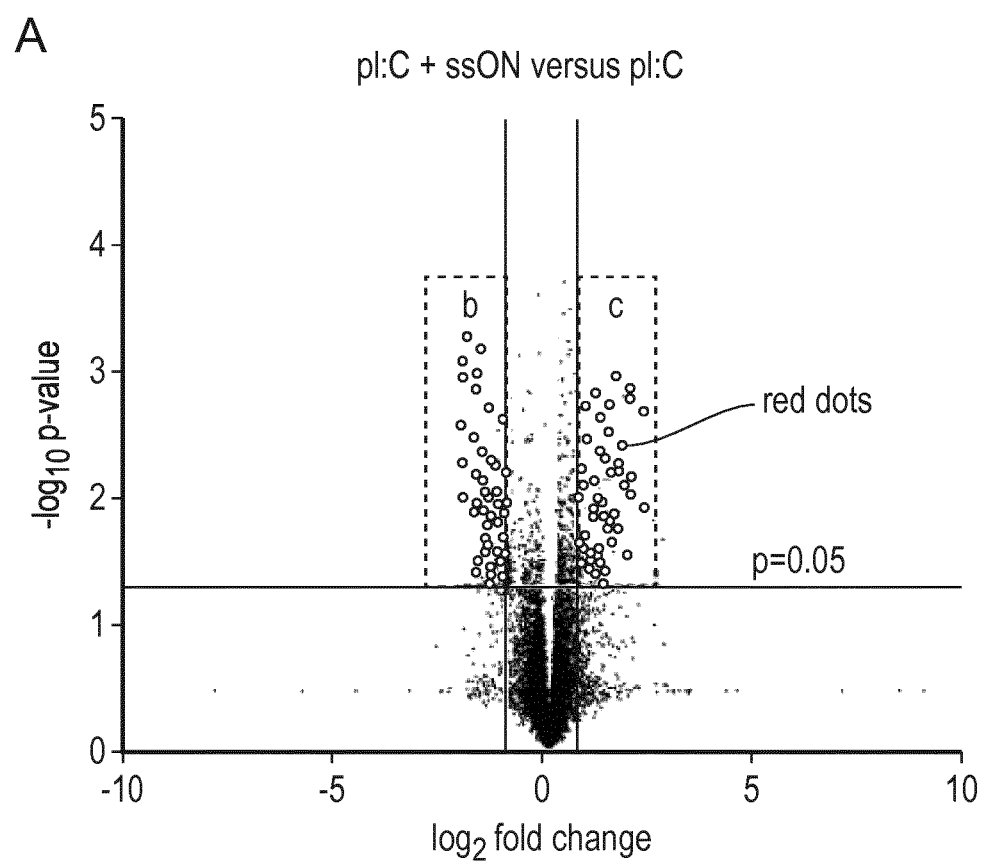
Figure 18:
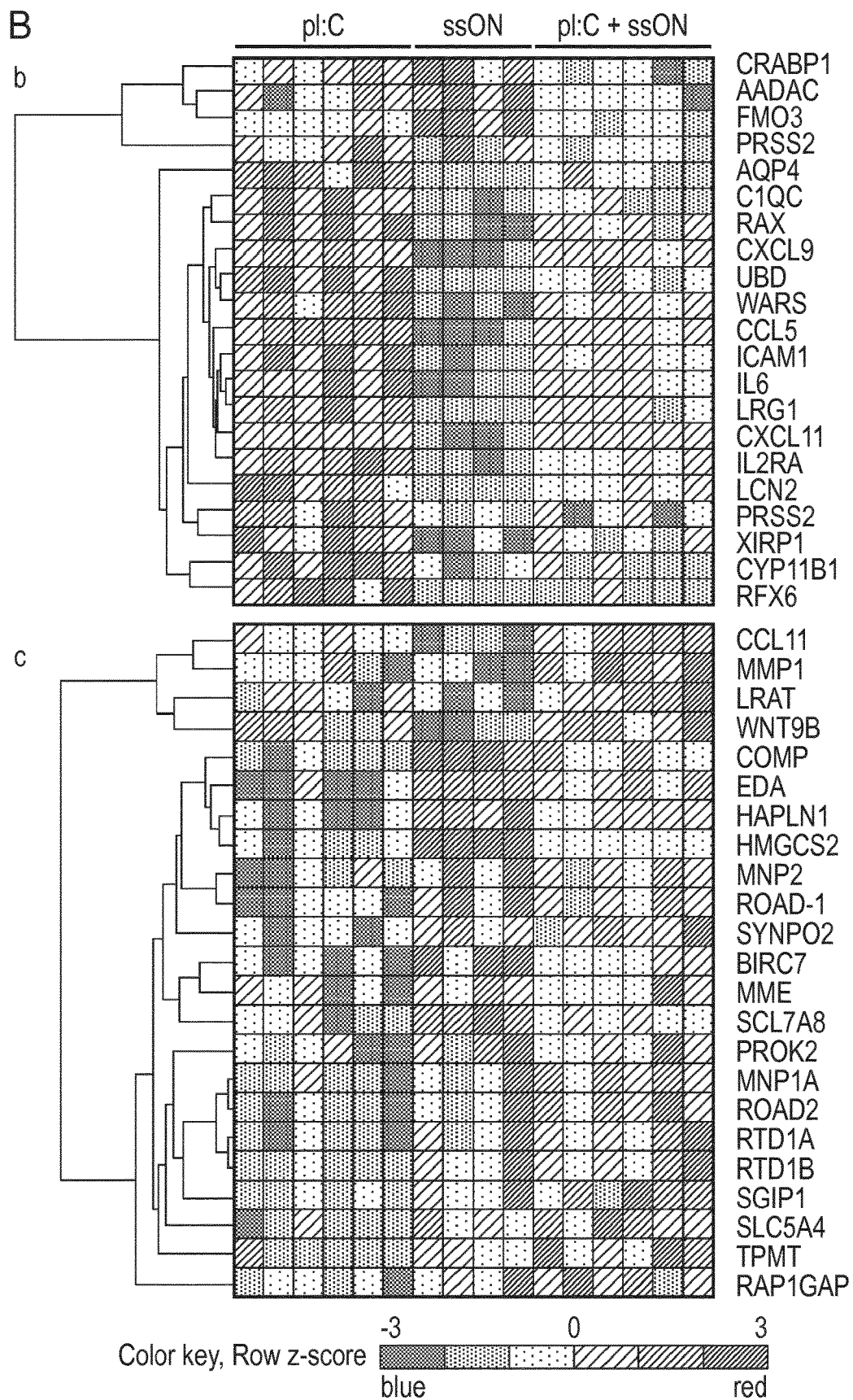
Figure 18:
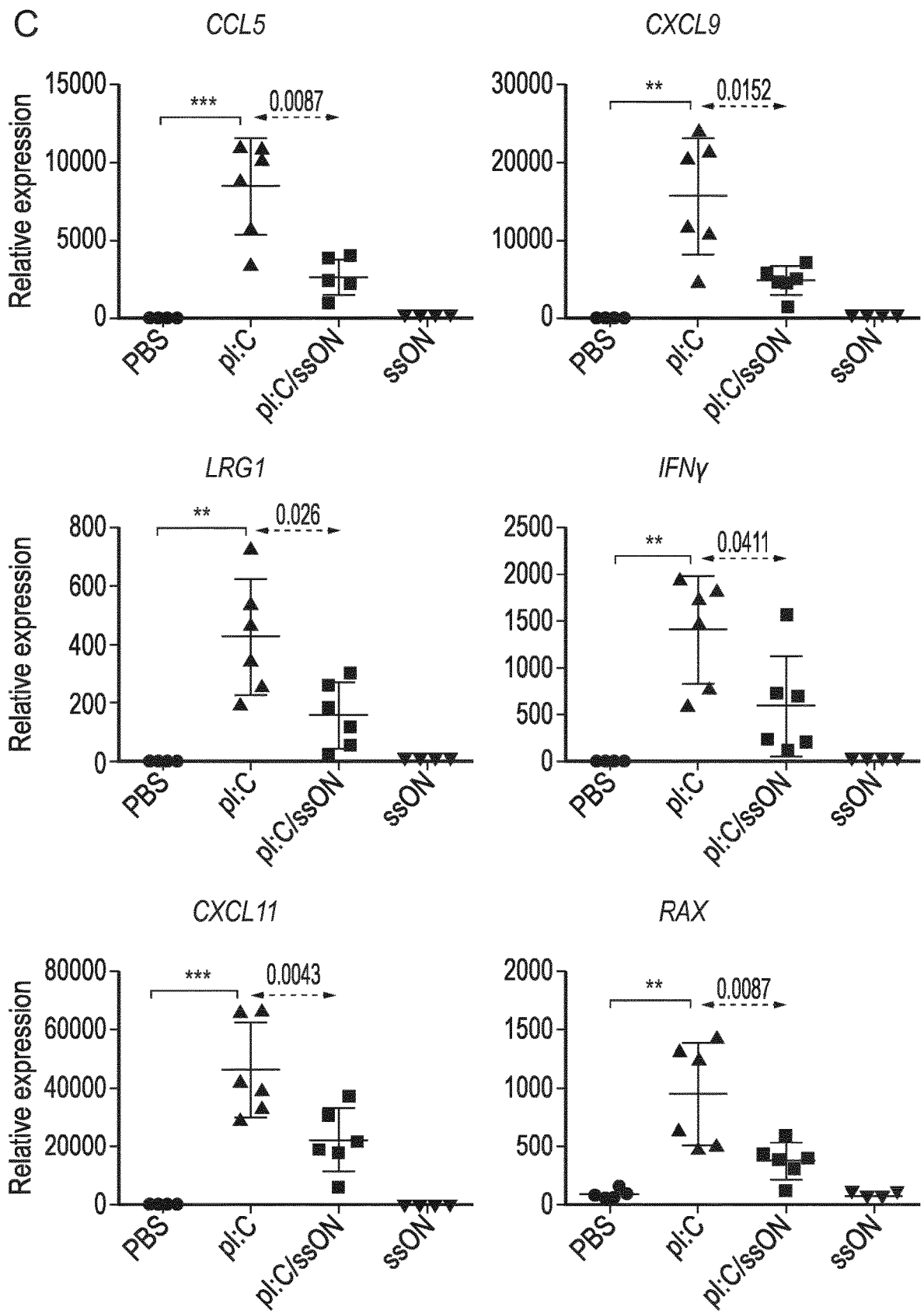
Figure 18:
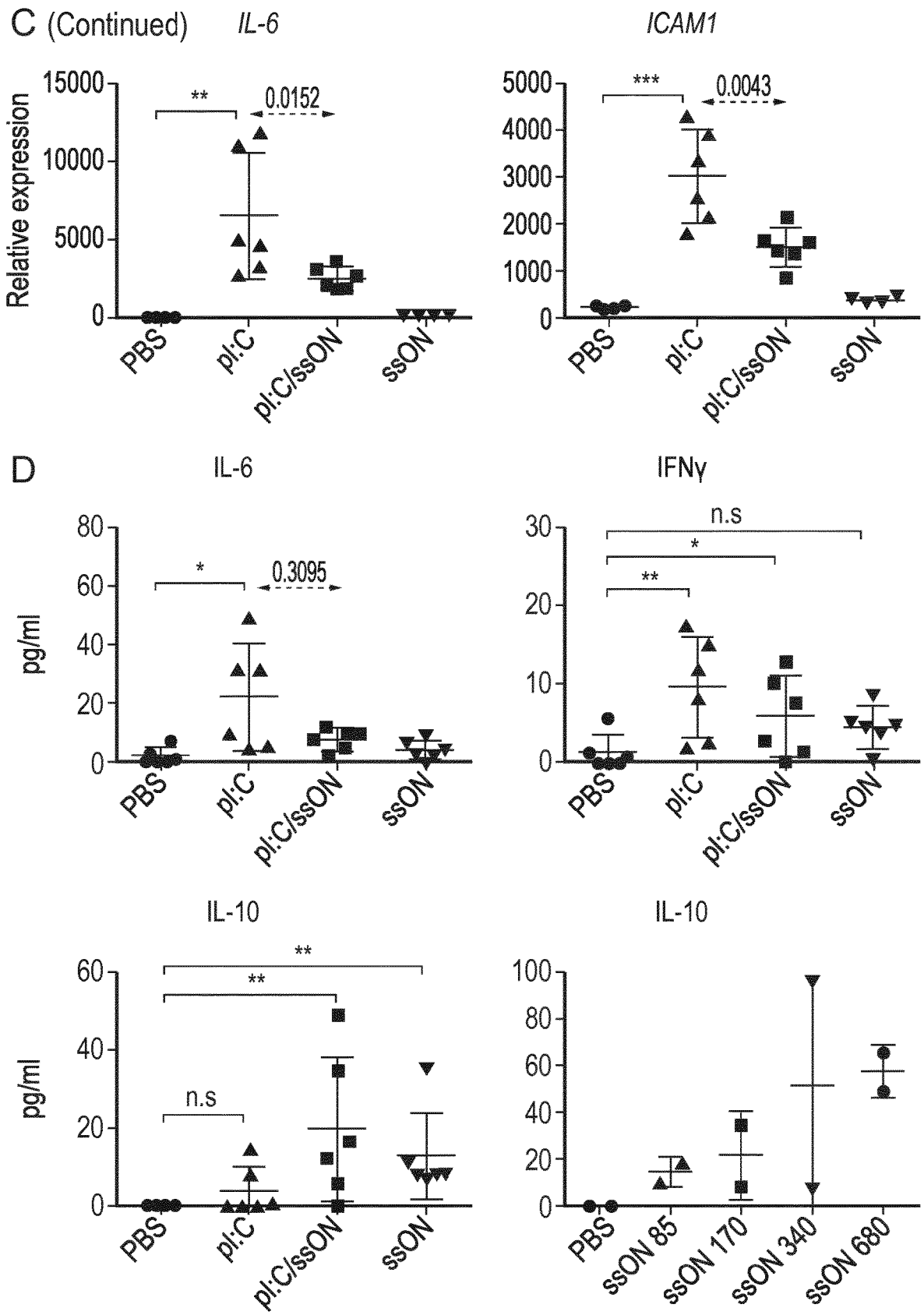

FIG. 18. SsON dampens dsRNA-mediated inflammatory signatures in macaque skin (A) RNA expression in skin following injection with dsRNA (pI:C) in the presence or absence of ssON 35 PS. Volcano plot illustrating log 2 fold-change and p<0.05 in red.

(B) Clustering of genes showing the highest differential expression comparing pI:C+ssON with ssON 35 PS treatment alone (b, c). Gene expression is represented as genewise standardized expression (Z score) with p<0.05. Red and blue correspond to up- and downregulated genes, respectively. Unsupervised hierarchical clustering of genes based on Spearman-correlation.

(C) Relative mRNA expression values from the microarray analyses of individual macaque skin biopsies 24 h post-stimulation (means±SEM).

(D) Concentrations of indicated cytokine proteins present in supernatants of enzymatically digested skin biopsies (24 h post-stimulation in vivo) (means±SEM from individual animals).

Lower right panel shows IL-10 production in a dose escalation experiment with ssON ranging from 85-680 µg per injection (n=2).

Significant differences were assessed by non-parametric Kruskal-Wallis test and Dunn's post test (* P<0.05,  P<0.01 and * P<0.001). Different treatment groups were compared using nonparametric Mann-Whitney unpaired test, as indicated.

Example 1: Extracellular Single Stranded Oligonucleotides Regulate Endocytic Uptake And Downstream Toll-Like Receptor Responses Summary Endocytic pathways need to be tightly regulated in order to maintain fundamental cellular functions and control uptake of molecules destined for endosomes. However, there is a lack of knowledge about extracellular molecules that regulate endocytic uptake. In the present study we show that single stranded oligonucleotides (ssON) inhibit some endocytic pathways in human monocyte derived cells (moDC), while leaving other pathways unaffected. Both single stranded DNA and RNA conferred the endocytic inhibition. It was affected by concentration and ssON length. The ssON-mediated inhibition modulated cell signalling downstream of pattern recognition receptors (PRR) that localize within the affected endosomal pathways. Introduction of non-natural linkages and/or modified nucleosides was not essential for inhibition, but was tolerated and might be necessary in order to retain the effect over longer periods of time. We provide evidence that ssON exerted immunomodulatory effects after intradermal injections in macaques. These studies reveal a regulatory role for extracellular ssONs in the endocytic uptake of Toll-like receptor (TLR) ligands and provide a mechanistic explanation for their immunomodulation. The identified ssON-mediated interference of endocytosis (SOMIE) is a regulatory process that temporarily dampens TLR3/4/7 signaling, thereby averting excessive immune responses.

Introduction

Endocytic mechanisms control lipid and protein compositions of the plasma membrane, thereby regulating how cells interact and communicate with their surrounding environment. In order to appropriately respond to, and influence its environment, the cell has to tightly regulate the plasma membrane composition as well as the uptake of ligands into endosomes (Doherty and McMahon, 2009). For example, cell surface removal of receptors enable long-term sensitivity to specific ligands (Irannejad and Zastrow, 2014). However, endocytosis does not only negatively regulate interactions with the external world. These processes also control fundamental mechanisms such as mitosis, cell migration, and immune-regulating processes such as initiation of the innate immune responses and antigen presentation (Doherty and McMahon, 2009). Immune regulation stems from the fact that many pathogens use endocytic pathways to mediate their cellular internalization (Cossart and Helenius, 2014). Likewise, nucleic acids released from microbes or dying cells are taken up through endocytosis enabling activation of TLRs located in the endosomes (Kawai and Akira, 2010).

Although a lot is known about the cargoes for different endocytic structures, the specific mechanisms by which these cargoes are engaged, internalized, and how their uptake is regulated, are less clear. There is an increasing stream of endocytosis pathways reported in the literature with varying degree of description and specificity. In the present study have assessed whether extracellular ssONs modulate three well defined pathways, Clathrin mediated endocytosis (CME), Caveolin dependent endocytosis (CDE), and Macropinocytosis (MPC) (Doherty and McMahon, 2009).

CME is mediated by small (100 nm diameter) vesicles, which have a coat made up by the clathrin protein. Clathrin-coated vesicles (CCVs) are found in virtually all cells and form domains of the plasma membrane termed clathrin-coated pits. These CCVs are responsible for removing GCPRs from the outer plasma membrane, reduce their signalling, and desensitise cells for specific ligands. Further, these pits can concentrate receptors responsible for the receptor-mediated endocytosis of ligands such as low-density lipoprotein, transferrin, and several others (Kumari et al., 2010), including dsRNA and its analogue pI:C (Itoh et al., 2008).

CDE is one of the most well studied non-clathrin-coated endocytosis pathways. It exists on the surface of many cell types, and consists of the protein caveolin and a bilayer enriched in cholesterol and glycolipids. Caveolae are smaller (approx. 50 nm in diameter) flask-shape pits in the membrane. The caveolar pathway is responsible for the endocytosis of ligands such as albumin, tetanus toxin, and cholera toxin subunit B (CTB) (Kumari et al., 2010).

MPC, occurs from highly ruffled regions of the plasma membrane, which then pinch off into the cell to form a larger vesicle (0.5-5 μm in diameter) filled with a large volume of extracellular fluid and molecules. Uptake indicators include fluid phase markers such as dextran (Doherty and McMahon, 2009).

Nucleic acid sensing TLRs localise distinctively to endosomes and stimulate moDC maturation in vitro (Isomura et al., 2005). TLR 3, 7, 8 and 9 initiate immune responses to infection by recognizing microbial nucleic acids in the endosomes. This localization of TLRs to distinct intracellular compartments plays a fundamental role in activating responses to foreign nucleic acids while maintaining tolerance to self-nucleic acids (Roers et al., 2016). TLR signalling constitutes a defense mechanism during viral infection in response to nucleic acids present in e.g. viral genomes or their intermediates during the replication cycle (Amarante and Watanabe, 2010; Vercammen et al., 2008). The dsRNA analogue pI:C is frequently used as a TLR3 agonist, and it has been shown to rely on CME to enter the endocytic pathway (Itoh et al., 2008).

In order to assess whether extracellular ssONs have the ability to modulate endocytic pathways, we here used a cellular model system that allows for both fluorescently based uptake studies using endocytic markers (e.g. Transferrin CTB and Dextran), and downstream cellular pathways from 'signalling endosomes' (Scita and Di Fiore, 2010; Sorkin and Zastrow, 2009). Cell signalling from endosomes occurs for receptors, such as NOTCH-family members, tumour necrosis factor receptor 1 and some TLRs (reviewed by Sorkin et al (Sorkin and Zastrow, 2009)). The TLRs that are located in endosomes (TLR3, TLR7, TLR8, and TLR9) are activated by ONs present in e.g. viral or bacterial genomes as well as viral intermediates during replication (Matsumoto et al., 2011). However, host-produced ONs also have the ability to initiate TLR signalling when released from damaged cells or tissues (Amarante and Watanabe, 2010; Pelka et al., 2016). While ON-sensing TLRs reside in and signal from specific endosomal compartments, TLR4 that senses bacterial lipopolysaccharides (LPS) has two distinct signalling pathways; one MyD88 dependent pathway that signals from the plasma membrane, and one TRIF dependent pathway that is reliant on CME and only can signal after endocytosis has occurred (Kagan et al., 2008; Rajaiah et al., 2015; Tatematsu et al., 2016).

Dendritic cells (DCs) are antigen-presenting cells that integrate stimuli from the environment leading to immune activation or induction and maintenance of immune tolerance. DCs consist of developmentally and functionally distinct subsets that differentially regulate T cell responses thereby acting as messengers between the innate and the adaptive immune systems (Merad et al., 2013). DCs subsets are present in tissues that are in contact with the external environment, such as the skin and the inner lining of the respiratory system as well as intestines. Because of their role as sensors of the external environment, DCs exhibit a wide variety of endocytic pathways. Further, as messengers between the innate and the adaptive immune systems they respond to several triggering molecules that are taken up and processed in the endocytic pathways, such as ON-sensing TLRs. Conversely, DNA that contains repetitive TTAGGG motifs originating from mammalian telomeres can inhibit immune reactions (Gursel et al., 2003). Synthetic ss-DNA molecules with immunosuppressive functions are being studied in pre-clinical models and they vary in size, sequence and nucleotide backbone but there is often a lack of understanding on their mechanism of action (Bayik et al., 2016).

It is well established that ONs do not passively cross the plasma membrane and transfection reagents or other membrane permeable approaches are required for intracellular delivery. (Sharma and Watts, 2015; Silva et al., 2015). However, free ONs have been suggested to be taken up through integrins and/or scavenger receptors (Juliano and Carver, 2015). Whether there is a difference in cellular uptake between ssONs and dsONs is to our knowledge not known. Here, we compared the endocytic capacity of ssONs with varying length and sequences. We showed that 35 bases long ssONs were not endocytosed by moDCs, and instead inhibited endocytosis of transferrin, CTB, and the dsRNA analogue polyinosinic-polycytidylic acid (pI:C) but spared uptake of dextran. Introduction of non-natural phosphorothioate linkages (PS) increased the inhibitory effect, but naturally occurring native phosphodiester (PO) ssONs and RNA purified from cells pI:C induced IL-6 production in short-term cultures.

We previously reported that a CpG containing ssON inhibited TLR3 signalling in primary human monocyte derived cells (moDC) that express TLR3/4/8, but lack TLR7/9 (Sköld et al., 2012). In the present study, we synthesized a panel of ssONs that lack CpG motifs, to identify the requirements for inhibition of dsRNA-mediated activation of moDC (Table A). We discovered that ssONs not only inhibited TLR3 activation but also activation of TLR7. Further, we show that ssON modulated signaling from TLR4 that was dependent on endosomal uptake, while leaving signaling from the plasma membrane unaffected. We provide evidence that certain ssON temporarily shut down CME without causing major harm to the cell, as shown by viability assay, cytokine production, RNAseq and whole cell proteomic analyses. Finally, we demonstrate that ssONs can shape the immune responses induced by dsRNA locally in the skin of macaques. These findings show that extracellular ssON's can inhibit CME and CDE, providing a mechanism to temporarily shut down uptake of cargo to endosomes, with subsequent alterations of the inflammatory signatures.

Results

Extracellular ssONs Inhibited Endocytosis of Transferrin and CTB

Here we investigated whether extracellular ssONs can inhibit uptake of commonly used markers of endocytic pathways in human moDCs (without any transfection method, or delivery system). Human moDCs were treated for 45 minutes at +37° C. or +4° C. with endocytic uptake markers (Transferrin, CTB, and Dextran as well as LDL) with or without addition of 0.5 μM ssONs (sequences in Table A). At +37° C. Transferrin, CTB and Dextran as well as LDL were taken up as measured by flow cytometry (FIG. 1 A-D, J). The fluorescent signals for Transferrin and CTB were significantly inhibited by the addition of 0.5 μM ssON 35 PO (FIGS. 1 A, B, G and H). Further, we found that the fluorescent uptake signals for Transferrin and CTB as well as LDL were fully blocked by the addition of 0.5 μM modified ssON 35 PS (FIGS. 1 C, D, G, H and J), while MPC remained unaffected by the treatment with ssON 35 PS, demonstrated by the same uptake of dextran at +37° C. with or without the addition of 0.5 μM ssON 35 PS (FIG. 1 E). At +4° C. no endocytosis occurs, showing that the addition of 0.5 μM ssON 35 PS (at 37° C.) completely inhibited Transferrin and CTB uptake (FIGS. 1 A, B, G and H). SsON 35 PS itself displayed the same uptake at both +4° C. and +37° C., showing that a fluorescently labeled ssON 35 PS stayed outside the cell and was not internalized into the endocytic pathways (FIGS. 1F and I). Altogether these findings show that both native ssON PO and ssON PS can significantly inhibit CME and CDE, but leave MPC intact, suggesting a regulatory role for ssONs in the uptake of cargo into endosomes.

Length Requirement for Extracellular ssONs Capacity to Inhibit Uptake of TLR3 Ligands and Subsequent TLR3 Activation in moDC The dsRNA analogue pI:C, is a TLR3 agonist that is taken up through CME (Itoh et al., 2008). We next asked whether ssON 35 PS can block pI:C mediated maturation of moDCs and if so whether it occurs by inhibition of endocytic uptake (FIG. 2). PI:C dependent moDC maturation was monitored 48 hours post treatment by measuring the expression of co-stimulatory molecules CD86 CD83 and CD80 in CD1a positive cells (CD83 and CD80 data not shown), and secretion of the pro-inflammatory cytokine IL-6 24 hours post treatment. We found that ssON significantly blocked pI:C mediated induction of CD86 in a concentration dependent manner with an $EC_{50}$ between 100-200 nM (FIG. 2 A, B). We further detected significant inhibition of pI:C mediated IL-6 secretion from moDCs by ssON 35 PS (FIG. 2 C). Similarly as with the uptake of endosomal markers transferrin and CTB, the inhibition of IL-6 was enhanced by, but not dependent on stability modifications of the ssON (FIG. 2 D). When using a naturally occurring PO backbone, the inhibitory effect was not present 48 hours post initial treatment (data not shown). However, when studying the inhibitory effect at earlier time points the ssON with a PO backbone had the same efficacy as a PS ssON. The effect remained for 3 hours, and was still present after 4 hours (FIG. 2D). After 5 h, the effect had diminished completely (data not shown). Microscopy studies further confirmed that uptake of fluorescently labelled pI:C in moDCs was efficiently blocked by the addition of 0.5 μM ssON 35 PS (FIG. 2 E, F).

We then asked if the observed inhibition of endocytosis and downstream TLR3 activation could be linked to and specific ssON sequence. We compared three different ssON sequences (ssON 35 PS, ssON GtA PS, and ssON Compl PS; Table A) they all displayed the same inhibitory effect in moDCs treated with pI:C for 48 hours (FIG. 2 G). SsON GtA was based on the parent sequence ssON 35, but all the guanosine (G) bases were substituted to adenosine (A), while ssON Compl is the complementary sequence to ssON 35. The three ssONs are all 35 bases long, and have a fully PS substituted backbone.

After concluding that the inhibitory effect was not strictly dependent on ssON sequence, we next assessed if the ssON length could influence the efficacy. We found that shorter ssONs did not possess the same inhibitory effect as longer ones with a cut off between 20 and 25 bases long ssONs (FIG. 2H, I). Microscopy studies showed that fluorescently labelled ssON 15 PS was readily taken up by moDCs, and that this cellular uptake was efficiently blocked by the addition of 0.5 μM ssON 35 PS (FIG. 2J, K). The block of endocytic uptake of the shorter ssON (ssON PS 15) was dependent on concentration of ssON 35 PS (FIG. 2L).

Altogether these data showed that ssON can inhibit endocytic uptake and downstream effects of the TLR3 agonist pI:C in a concentration dependent manner and that the effects were not linked to a specific ssON sequence or motif. The ssON length did affect the inhibitory effects, and had a cut-off between 20-25 bases.

Kinetics of ssON Mediated Inhibition of TLR Signalling

If extracellular ssONs are able to inhibit certain endocytic pathways, the biokinetics should follow previous endosomal uptake studies in moDCs (Choi et al., 2013; Smole et al., 2015). We therefore assessed the kinetics of both activation and inhibition of moDC maturation by exposing cells to either TLR3 agonist pI:C or inhibiting ssON 35 PS and subsequently pulsed cells with ssON 35 PS/pI:C over a period of time ranging from 5 minutes to 24 hours. Expression of co-stimulatory CD86 and secretion of IL-6 were measured as signs of pI:C induced moDC maturation. Cellular exposure to pI:C followed by pulsing with ssON 35 PS showed that the inhibiting effect was present up to 50 minutes, and was then rapidly reduced and vanished about 2 h post initial pI:C treatment (FIG. 3A, B). MoDCs treated in the reverse fashion with ssON 35 PS first, and then pulsed with pI:C showed no sign of maturation or cytokine production for up to 24 hours post initial treatment (FIG. 3C, D). The addition of ssON 35 PS inhibited TLR3 activation for up to 50-60 min after exposure to the agonist (FIG. 3A). According to previous studies, it takes about 35-60 min for human moDCs to endocytose extracellular compounds (Smole et al., 2015). Altogether, our findings suggested that under circumstances when the TLR3 agonist were endocytosed and initiation of TLR3 signalling had been initiated, the addition of ssON 35 PS was not able to inhibit pI:C induced moDC maturation. At earlier time points however, ssON 35 PS inhibited the processes.

SsON Prevented pI:C Mediated Cell Death in Human moDCs

PI:C can induce apoptosis in human cells (Sun et al., 2011). To assess if ssONs can prevent this, moDCs were treated with pI:C with or without the addition of ssON 35 PS and apoptosis was measured by Live/Dead cell stain kit using flow cytometry. Cells treated with only pI:C had a reduced viability by approximately 20%. The frequency of cell death was reduced back to the level of untreated cells by the addition of 0.5 µM ssON 35 PS, 48 hours post-initial treatment (FIG. 3E).

Inhibition of pI:C Uptake Occurred for ssONs but not dsONs

We provide data here showing that extracellular ssONs ability to inhibit endocytic uptake was dependent on ON length, but independent of its sequence (FIG. 2). In order to assess if the introduction of dsON influences endocytic uptake, ssON 35 PS was kept at a constant concentration (0.5 µM), while increasing concentrations of the complementary strand (ssON Compl 35 PO) were introduced (FIG. 3F). MoDCs were treated with pI:C, and the inhibitory activity of the ssON (monitored by CD86 expression 48 hours post initial treatment) was reduced when the complementary strand was introduced. The inhibitory effect was completely absent when all the ssON 35 PS had a complementary strand to hybridize with (ssON Compl PO 1 µM).

The Inhibitory Effect of ssONs Occurred for TLR3 and TLR7 Located in Endosomes but Spared Effects by Membrane Permeable TLR Agonist As ssON-sensing TLRs are dependent on endocytosis and signalling occurs from signalling endosomes (Sorkin and Zastrow, 2009), we next assessed whether ssONs have the ability to block TLR-induced moDC maturation from a membrane permeable TLR agonist. R848 is a membrane permeable TLR7/8 agonist, and is thus not dependent on endocytosis to activate TLR signalling (Govindaraj et al., 2011). CL307 is a TLR7 agonist that is coupled to spermin, and hence dependent on endocytosis for its cellular uptake (Soulet et al., 2002). MoDCs lack the expression of ssON-sensing TLR7, thus these experiments were performed in peripheral blood mononuclear cells (PBMCs). PBMCs were treated with pI:C (TLR3 agonist), CL307 (TLR7 agonist), or R848 (membrane permeable TLR7/8 agonist) in the absence or presence of ssON 35 PS (FIG. 3G). SsON 35 PS significantly reduced the secretion of IL-6 from PBMCs treated with pI:C and CL307, but not after R848 stimulation. These data showed that extracellular ssON 35 PS only has the ability to inhibit TLR induced secretion of pro-inflammatory IL-6 if the agonist is dependent on endocytosis to reach its receptor.

SsON Mediated Inhibition of TLR4 Signalling was Dependent on Endosomal Uptake

TLR4 responds to LPS stimulation and has two distinct signalling pathways (Kagan et al., 2008; Rajaiah et al., 2015; Tatematsu et al., 2016). One is mediated through MyD88 and occurs at the plasma membrane leading to NFkB activation. The second pathway is mediated through TRIF, stimulating a strong interferon response. The TRIF mediated signalling occurs from clathrin-coated endosomes, and is hence dependent on CME (FIG. 4A). We therefore reasoned that the addition of ssON 35 PS in combination with a TLR4 agonist should primarily inhibit the interferon response in moDCs, as extracellular ssONs inhibited CME pathways (FIG. 1). To test this hypothesis we treated MoDCs simultaneously with the TLR4 agonist LPS and ssON 35 PS. Signalling through the MyD88 dependent pathway was assessed by the secretion of IL-6 and IL-10, and the TRIF dependent pathway was assessed by the secretion of IL-29 and CXCL10 (Rosadini et al., 2015). When moDCs were exposed to LPS and ssON 35 PS ssON, the secretion of IL-6 and IL-10, which are downstream of the MyD88 dependent pathway remained unaffected (FIGS. 4B and C), while we found significant inhibition of CXCL10 and IL-29 (FIGS. 4D and 4E). This shows that the addition of ssON 35 PS selectively inhibited one out of two pathways originating from the same TLR. One is dependent on endocytosis, and the other is not. To verify that LPS was taken up into cells and that ssON inhibited this uptake, we exposed moDCs with Alexa-488 labelled LPS and quantified uptake by flow cytometry. We found significant increase in the fluorescent signal after incubation at 37° C. compared with 4° C. and furthermore that the uptake of LPS at 37° C. was significantly inhibited in the presence of ssON 35 PS (FIGS. 4F and G). The uptake of LPS was verified by microscopy and also showed inhibition of uptake in the presence of ssON at 37° C. (FIGS. 4 H and I).

Inhibition of Endosomal Uptake can be Achieved with Both DNA and RNA

To elucidate if the ability to inhibit endocytic uptake is exclusive for DNA, or if RNA also possesses this activity, we synthesised 35 mer ssON RNA and RNA analogues (Table A). A native unmodified RNA 35-mer had no effect on endocytic uptake in moDCs (data not shown). However, the ON RNA analogue 2'OMe and total RNA purified from moDCs had the ability to inhibit endosomal uptake (FIGS. 5A and B). PI:C induced secretion of IL-6 was reduced by ssON 2'OMe PS to levels comparable to ssON 35 PS (FIG. 5C). Using the same assay, total RNA (totRNA) purified with a cut off filter below 200b reduced the production of IL-6 in a concentration dependent manner (FIG. 5D). These data showed that ssONs with capacity to inhibit endocytic uptake in human moDCs can be of either DNA or RNA origin.

Administration of ssON 35 PS Modulated dsRNA-Mediated Inflammation in the Skin of Macaques To assess whether the stabilized ssON 35 PS can mediate effects in vivo, we measured the global innate response to pI:C in the presence or absence of ssON 35 PS by transcriptional profiling of skin biopsies taken from the site of injection. We found that intradermal injection of pI:C resulted in induction of multiple innate immune response genes as compared to injection of PBS (FIG. 6A). Gene Ontology (GO)-annotation of significantly regulated genes (p<0.05) following pI:C injection compared to PBS controls showed enrichment of genes linked to GO processes "defense response" (false discovery rate (FDR) q-value: 2.85E-48) and "immune system process" (FDR q-value: 1.14E-47). Further, the GO functions "cytokine activity" and "chemokine activity" were enriched (FDR q-value: 7.95E-14 and 2.25E-10, respectively). To get more insight as to which genes showed a modulated expression in the skin, we compared the group receiving intradermal injection of only pI:C with the group receiving pI:C/ssON, and calculated the fold change as well as the significance of the difference between the two groups (FIG. 6B). The results show that among the top down-regulated genes, comparing pI:C/ssON 35 PS co-administration with pI:C treatment alone, are chemokines and genes implicated in inflammatory conditions (FIG. 6C top). It can be noted that expression of IL-6 was among the top down-regulated genes (negative FC>2 p<0.05) (FIG. 6D), supporting the in vitro data (FIG. 2C). We further validated secretion of IL-6 by analyzing aliquots of filtered-dermis supernatant collected without additional stimulation in vitro (FIG. 6E). Significant (p<0.05) induction of IL-6 was detected after pI:C treatment, which was reduced after the pI:C/ssON 35 PS treatment. Taken together our data show that pI:C induced significant inflammatory signatures locally in the macaque skin, which is dampened by co-administration of ssON 35 PS.

Experimental Procedures

Single Stranded Oligonucleotides

Fully PS-substituted ssON 35 PS and 2'OMe PS were made by made by Integrated DNA Technologies. Other modified oligonucleotides were purchased from Eurofins. For sequences, see Table A. Total RNA was purified from moDCs using RNeasy total RNA purification kit, according to manufacturer's instructions (Qiagen).

TLR Ligands and Labeled Endosomal Markers

TLR3 ligand high molecular weight pI:C (25 µg/mL unless otherwise stated), TLR7 ligand CL307 and TLR7/8 ligand R848 were all purchased from Invivogen. Endosomal markers; Transferrin-Alexa647, Cholera toxin B-Alexa488, Dextran-Texas red 10 kDa, and LPS-Alexa488 were all purchased from Life Technologies.

Uptake Studies in MoDCs

Human Monocytes were negatively selected from buffy coats using the RosetteSep Monocyte Enrichment Kit (1 mL/10 mL buffy coat; StemCell Technologies) and differentiated into moDC, with GM-CSF (250 ng/mL; PeproTech) and IL-4 (6.5 ng/mL; R&D Systems) for 6 days at a density of $5 \times 10^5$ cells/mL in RPMI 1640 completed with 10% FCS, 1 mM sodium pyruvate, 10 mM HEPES, 2 mM L-glutamine, and 1% streptomycin and penicillin (all from Invitrogen Life Technologies). MoDCs were exposed to endosomal markers and ssON on ice in complete 10% RPMI media (or serum free media for PO ON uptake studies), and then transferred to 37° C. for 45 minutes. After incubation, the cells were put back on ice, washed and fixed and uptake was monitored by flow cytometry. CME was monitored by uptake of 50 µg/ml Alexa647 labeled Transferrin. CDE was monitored by 1 µg/ml Alexa488 labeled cholera toxin B, and MPC was monitored by 0.5 mg/ml Texas-Red labeled Dextran. Endocytic uptake of TLR4 was monitored by 1 µg Alexa488 labeled LPS. Uptake of LDL was measured by quantifying uptake of DiL labelled LDL (Molecular probes).

MoDC Maturation Studies

Human Monocytes were differentiated as described above. MoDCs were exposed to pI:C and ssON and maturation was assessed 48 hours later using monoclonal antibodies (Abs) targeting CD1a and the moDC maturation markers, CD86, CD83, and CD80 (all Abs from BD Biosciences). Flow cytometry sample data were acquired on a Fortessa (BD Biosciences) and the analysis was performed with FlowJo software (TreeStar).

Cytokine/Chemokine Secretion Studies

Supernatants were collected from cells at given time points post treatment (pI:C, CL307, R848 (Invivogen) or LPS (Sigma)) and secretion of Cytokines/Chemokines was measured by standard ELISA according to manufacturer's instructions (Mabtech; IL-6, IL-10, and IL-29. Life Technologies: CXCL10). Protein amount was monitored by 3,3',5,5'-Tetramethylbenzidine (TMB) absorbance at 450 nm, and given in pg/ml or relative absorbance units.

Wide-Field Microscopy

MoDCs were adhered in phenol red-free complete RPMI medium to poly-L-lysine coated glass slides for 2-4 h. Cells were treated with indicated ligands at 37° C. for 45 minutes in the presence of absence of ssON 35 PS. Non-bound ligands were washed away and the cells were covered with complete medium and acquired at 37° C. in a wide-field Cell Observer microscope using the 40× lens. Images were acquired and analyzed using the SlideBook 6 program (Intelligent imaging innovations).

Kinetic Analysis of TLR3 Inhibition

To elucidate the kinetics behind the observed inhibition of TLR3 signalling, moDCs were exposed to 25 µg/ml pI:C/0.5 µM ssON 35 PS and then pulsed with either 0.5 µM ssON 35 PS or pI:C respectively over a time period from 5 minutes to 24 hours. Cells were analyzed by flow cytometry 48 hours post initial exposure for expression of moDC maturation markers CD80 and CD86. Additionally, supernatant was collected from cells 48 hours post treatment and secretion of pro-inflammatory IL-6 was measured by ELISA (Mabtech).

Viability Test

Viable cells were selected from total cell populations 48 hours post initial treatment with 25 µg/ml pI:C/0.5 µM ssON 35 PS. Viable cells were assessed using a Live/Dead fixable near-IR dead cell stain kit according to manufacturer's protocol (Life Technologies). Sample data was acquired using a Fortessa (BD Biosciences) and analysed using FlowJo software (TreeStar Inc.).

MoDC Maturation Studies with dsON

SsON 35 PS was pre-incubated at 5 µM with complementary ssON 35 PO at 1-10 µM in PBS at 55° C. and then left at ambient temperature for 30 minutes. ON mixture was added to MoDC in a final concentration of 0.5 µM ssON 35 PS in combination with 25 µg/ml pI:C. MoDC maturation was assessed as described above.

Animals and Injections

Adult cynomolgus macaques (*Macaca fascicularis*) (n=18), were handled in accordance with European guidelines for NHP care (EU Directive N 63/2010). This study was approved and accredited under statement number 12-013 by the Ethical Animal Committee of the CEA "Comité d'Ethique en Expérimentation Animale" registered by the French Research Ministry under number 44. Animals were handled under sedation and intradermal injections were done in the upper left and right back flank with 170 µg of pI:C alone or with 170 µg of ssON in 100 µL of PBS, or PBS alone. Skin biopsies (8 mm in diameter) were collected from anesthetized animals 24 hours after injection.

Cytokine Secretion Assays in Macaque

To evaluate cytokine and chemokine production from macaque skin biopsies directly ex vivo, aliquots of filtered-dermis supernatants were collected and measured with the MILLIPLEX MAP NHP Cytokine Magnetic Bead Panel (Millipore) on a Bio-Plex device (Bio-Rad), according to manufacturer's instructions.

Microarray Analysis

Whole skin RNA were extracted from macaque skin biopsies, stored at least 24 hours at 4° C. in RNA Later, using Tissue Ruptor® followed by RNeasy Plus Universal Kit (QIAgen), according to manufacturer's instructions. Total RNA was quality checked on Agilent 2100 Bioanalyzer. RNA quantity was measured using NanoDrop ND-1000 Spectrophotometer. Cyanine-3 (Cy3) labeled cRNA was prepared from 200ng Total RNA using the Quick Amp Labeling Kit (Agilent) according to the manufacturer's instructions, followed by RNeasy column purification (QIAGEN, Valencia, Calif.). Dye incorporation and cRNA yield were checked with the NanoDrop ND-1000 Spectrophotometer. 1.65 µg of Cy3-labelled cRNA was fragmented at 60° C. for 30 minutes in a reaction volume of 55 µL containing 1× Agilent fragmentation buffer and 2× Agilent blocking agent following the manufacturer's instructions. On completion of the fragmentation reaction, 55 µL of 2× Agilent hybridization buffer was added to the fragmentation mixture and hybridized to Agilent Rhesus Macaque Gene Expression Microarrays v2 for 17 h at 65° C. in a rotating Agilent hybridization oven. After hybridization, microarrays were washed 1 min at room temperature with GE Wash Buffer 1 (Agilent) and 1 min with 37° C. GE Wash buffer 2 (Agilent). Slides were scanned immediately after washing on the Agilent DNA Microarray Scanner (G2505C) using one color scan setting for 4×44K array slides (Scan Area 61×21.6 mm, Scan resolution 5 µm, Dye channel is set to Green, PMT is set to 100%). The scanned images were analyzed with Feature Extraction Software 10.7.3.1 (Agilent) using default parameters to obtain background subtracted and spatially detrended Processed Signal intensities. The signals were background correction by the Robust Multi-array Average (RMA) method and quantile-normalized. For the generation of heat maps and cluster analysis, the data was $\log_2$ transformed and mean centered.

Statistical Analysis

Non-parametric Mann-Whitney test was used to compare the presented data. Number of donors and repeated experiments is stated in each figure legend. P-value: not significant (n.s) P>0.05; * P≤0.05;  P≤0.01; * P≤0.001.

Human In Vitro Derived DCs

Monocytes were negatively selected from buffy coats using the RosetteSep™ Monocyte Enrichment Cocktail (StemCell Technologies) and differentiated into DC, as described previously (Sköld, A. E. et al 2012 Blood 120: 768-777) at a density of 5×10⁵ cells/mL in RPMI 1640 completed with 10% FCS, 1 mM sodium pyruvate, 10 mM HEPES, 2 mM L-glutamine, and 1% streptomycin and penicillin (all from Invitrogen Life Technologies), with GM-CSF (250 ng/mL; PeproTech) and IL-4 (6.5 ng/mL; R&D Systems) for 6 or 7 days. 1×10⁵ MoDCs were exposed to Cy3 labeled ploy I:C (polyI:C was labeled using Mirusbio LabelIT® Nucleic Acid Labeling Kit 3600 according to manufacturer's protocol) and MedON oligonucleotides on in 100 µl complete 10% RPMI media, at 37° C. or +4° C. for 45 minutes. After incubation, the cells were washed with ice cold PBS, fixed and uptake was monitored by flow cytometry. Sample data were acquired on a FACSCalibur™ or Fortessa™ (BD Biosciences); the analysis was performed with FlowJo™ software (TreeStar).

Influenza Infection of DCs

Monocyte-derived dendritic cells (MoDCs), differentiated for 6-7 days in the presence of GM-CSF and rIL-4, were pretreated with ssONs (see Table 1; 0.5 µM) for 2 hours and then exposed to different MOI (multiplicity of infection) of influenza H1N1 Cal07/09. MoDCs (500.000/ml) were exposed to influenza at MOIs of 0.2 or 2 for two hours. The cells were thereafter washed and cultured with ssONs (see Table 1; 0.5 µM), for 24 hours. RNA was isolated from the cell culture supernatants and the viral load was measured by

TABLE A

| Name | Sequence | Length | SEQ ID NO | Med ON No |
|---|---|---|---|---|
| ssON 35 PO | GAAGTTTTGAGGTTTTGAAGTTGTTGGTGGTGGTG | 35 | 2 | 02 |
| ssON 35 PS | G*A*A*G*T*T*T*T*G*A*G*G*T*T*T*T*G*A*A*G*T*T*G*T*T*G*G*T*G*G*T* | 35 | 1 | 01 |
| ssON 30 PS | G*G*T*G | 30 | 3 | 03 |
| ssON 25 PS | A*G*T*T*T*T*G*A*G*G*T*T*T*T*G*A*A*G*T*T*G*T*T*G*G*T*G*G*T*G | 25 | 4 | 04 |
| ssON 20 PS | T*T*T*T*G*A*G*G*T*T*T*T*G*A*A*G*T*T*G*T*T*G*G*T*G*G | 20 | 5 | 05 |
| ssON 15 PS | T*G*A*G*G*T*T*T*T*G*A*A*G*T*T*G*T*T*G*G G*G*T*T*T*T*G*A*A*G*T*T*G*T*T | 15 | 6 | 06 |
| ssON GtA PS | A*A*A*A*T*T*T*A*A*A*A*T*T*T*T*A*A*A*A*T*T*A*T*T*A*A*T*A*A*T* A*A*T*A | 35 | 24 | 024 |
| ssON Compl PO | CACCACCACCAACAACTTCAAAACCTCAAAACTTC | 35 | 7 | 07 |
| ssON Compl PS | C*A*C*C*A*C*C*A*C*C*A*A*C*A*A*C*T*T*C*A*A*A*A*C*C*T*C*A*A*A*A | 35 | 7 | 07 |
| ssON 2'OMe PS | *C*T*T*C | 35 | 8 | 08 |
| totRNA | *G*A*A*G*U*U*U*U*G*A*G*G*U*U*U*U*G*A*A*G*U*U*G*U*U*G*G*U*G*G* U*G*G*U*G*<br>Random | >200 | | |

All sequences written 5' to 3'  * = PS  *italic* = RNA  _ = 2'OMe

Experimental Methods for Examples 2-8

Synthesis of Oligonucleotides Synthetic, endotoxin-free, oligonucleotides were synthesized according to methods known in the art, as disclosed in e.g. Artificial DNA: Methods and Applications (Khudyakov, Y. E. & Howard A. Fields, H. A., Eds.) CRC Press, 2002 (ISBN 9780849314261).

QT-PCR. The supernatants were harvested at the indicated time points and kept at −80° C. until RNA purification was performed. QIAamp® Viral RNA mini kit (QIAGEN) was used for viral RNA purification in supernatants, following manufacturer's protocol. Viral load was determined by qRT-PCR (SuperScript® III Platinum® One-Step Quantitative RT-PCR System, Life Technologies) using IAV Cal07/09 as internal standard. Taqman Real-Time PCR using primers and probe specific for IAV Cal07/09 HA segment.

The following primer sequences (5'-3') specific for IAV HA segment were used:

(SEQ ID NO: 26)
Forward: GGCTGCTTTGAATTTTACCACAA;

(SEQ ID NO: 27)
Reverse: TTTGGGTAGTCATAAGTCCCATTTT;

as well as the probe FAM-TGCGATAACACGTGCATG-GAAAGTGTC-TAMRA (SEQ ID NO: 28)

MoDC Maturation Studies

Human Monocytes were differentiated as described above. MoDCs were exposed to polyI:C and MedONs and maturation was assessed 48 hours later using monoclonal antibodies (Abs) targeting CD1a and the moDC maturation markers CD86 (all Abs from BD Biosciences). Flow cytometry sample data were acquired on a Fortessa (BD Biosciences) and the analysis was performed with FlowJo software (TreeStar).

Cytokine/Chemokine Secretion Studies

Supernatants were collected from cells at given time points post treatment polyI:C (Invivogen) and MedONs. Secretion of IL-6 was measured by standard ELISA according to manufacturer's instructions (Mabtech). Protein amount was monitored by 3,3',5,5'-Tetramethylbenzidine (TMB) absorbance at 450 nm, and given in pg/ml or relative absorbance units.

In Vivo Influenza a Infection of Mice

BALB/c mice were placed into groups of n=5 and housed in a fully acclimatized room. $5\times10^5$ PFU influenza H1N1 A/Eng/195/2009 virus in 100 µl were administered nasally to anesthetized mice. In indicated group ssON (25 µg) (MedON-01) were co-administered with the virus. In a third group, ssON (25 µg in 25 µl) in PBS were administered nasally to anesthetized mice day 3 post-virus infection. Mice body weights were monitored every day for productive infection as determined by weight loss. To determine lung viral loads, mice were culled 4 days post infection.

Determination of Lung Viral Titres and Cytokines

After collection of bronchoalveolar lavage (BAL), lungs were removed and homogenized by passage through 100 µm cell strainers, then centrifuged at 200×g for 5 minutes. Supernatants were removed and stored for ELISA analysis and the cell pellet treated with red blood cell lysis buffer (ACK; 0.15 M ammonium chloride, 1 M potassium hydrogen carbonate, and 0.01 mM EDTA, pH 7.2) before centrifugation at 200×g for 5 minutes. The remaining cells were resuspended in RPMI 1640 medium with 10% fetal calf serum, and viable cell numbers determined by trypan blue exclusion.

Viral load in vivo was assessed using Trizol extracted RNA from frozen lung tissue disrupted in a TissueLyzer (Qiagen, Manchester, UK). RNA was converted into cDNA and quantitative RT-PCR was carried out using bulk viral RNA, for the influenza M gene and mRNA using 0.1 µM forward primer:

(SEQ ID NO: 29)
5'-AAGACAAGACCAATYCTGTCACCTCT-3', 0.1 µM reverse primer:

(SEQ ID NO: 30)
5'-TCTACGYTGCAGTCCYCGCT-3',
and 0.2 µM probe:

(SEQ ID NO: 31)
5'-*FAM*-TYACGCTCACCGTGCCCAGTG-*TAMRA*-3', on a Stratagene Mx3005p (Agilent technologies, Santa Clara, Calif., USA). M-specific RNA copy number was determined using an influenza M gene standard plasmid.

Statistical Analysis

Statistical analyses were performed with Prism 5.0™ (Graph-Pad Software Inc.) using nonparametric Kruskal-Wallis unpaired test followed by Dunn's post-test (*P<0.05, P<0.01 and *P<0.001) or one-way ANOVA. When indicated different treatment groups were compared using non-parametric Mann-Whitney unpaired tests.

Example 2: MedON-01 Inhibits the Uptake of PolyI:C

Human monocyte-derived cells were treated for 45 min at +37° C. or +4° C. with endocytic, fluorescently labeled, uptake marker (PolyI:C) with or without addition of MedON-01. At +37° C. PolyI:C was taken up as measured by flow cytometry (FIG. 7). FIG. 7 shows dose-dependent inhibition of the uptake of PolyI:C in primary human monocyte-derived cells by treatment with MedON-01 in vitro.

Example 3: The Capacity to Inhibit Uptake of PolyI:C is not Strictly Dependent on Sequence but Requires a Certain Length and Chemical Modification of the Oligonucleotide Human monocyte-derived cells were treated for 45 min at +37° C. or +4° C. with endocytic, fluorescently labeled, uptake marker (PolyI:C) with or without addition of MedON-01-23. At +37° C. PolyI:C was taken up as measured by flow cytometry (FIG. 8). FIG. 8 shows inhibition of the uptake of PolyI:C in primary human monocyte-derived cells by treatment with MedON-01, 03, 04, 07, 08, 10, 11, 13-21 in vitro using 0.5 µM.

Example 4: Inhibition of Influenza a by Pre-Treatment with MedON-01

Human monocyte derived DCs were infected in vitro with Influenza H1N1 Cal2009 (IAV) using MOI 0.2 or MOI 2. MoDC were either untreated or pre-treated with MedON-01 shown as SEQ ID NO: 1 (0.5 µM) for 2 hours before infection. Infection with IAV was then carried out during another 2 hours. Cells were washed and incubated for 24 hours either with MedON-01 (SEQ ID NO: 1) added again or not (m=medium). The viral load in the culture supernatants were quantified by real time PCR. Data were obtained in four independent experiments using six different donors analyzed in triplicate. Statistical calculations were made using non-parametric paired Wilcoxon text.

The results (FIG. 9) show a marked and highly significant reduction in viral load using both doses of IAV (0.2 and 2 MOI).

Example 5: The Capacity to Inhibit Influenza a Infection is Sequence Independent but Requires a Certain Length and Chemical Modification of the Oligonucleotide Human monocyte derived DCs were infected in vitro with Influenza H1N1 Cal2009 (IAV) using MOI 1. MoDC were either untreated or pre-treated with MedON's shown (see FIG. 10 and Table 1 (1 µM) for 2 hours before infection. Infection with IAV was then carried out during another 2 hours. Cells were washed and incubated for 24 hours either with MedON's added again or not (m=medium). The viral load in the culture supernatants were quantified by real time PCR. Data were obtained i using two different donors analyzed in triplicate.

The results (FIG. 10) show reduction in viral load without causing cell death using MedON01,03,04,07,10,11,13-21 of IAV (1MOI).

Example 6: Inhibition of Influenza a Viral Load by MedON-01 Treatment In Vivo Balb/c mice were infected intranasal with Influenza H1N1 (Cal09). One group were untreated (FIG. 11A; circles), a second group received 25 µg of ssON (MedON01, SEQ ID NO: 1) intranasal at the same time as the viral challenge (FIG. 11A; squares) and a third group received an intranasal treatment of 25 µg ssON day 3 (FIG. 11A; triangles). The mice were sacrificed day 4 after infection and the viral load was measured in the lungs. Statistical calculations were made using 1-way ANOVA.

As shown in FIG. 11A, there was significant reduction in the viral load of the mice when MedON-01 was given either as a prophylactic treatment (squares) or as a therapeutic treatment on day 3 (triangles).

Mice were weighed every day, which is a sensitive measure of their well-being during virus infections. The mice that received the prophylactic treatment with MedON-01 were able to maintain their weight (FIG. 11B; squares).

Example 7: TNF-α and IL-6 Production in MedON-01 Treated Influenza A Infected Mice Balb/c mice were infected intranasally with Influenza H1N1 (Cal09). One group were untreated (FIG. 12; circles). The second group received 25 µg of ssON (MedON-01, SEQ ID NO: 1) intranasally at the same time as the viral challenge (FIG. 12; squares). The third group received an intranasal treatment of 25 µg MedON-01on day 3 (FIG. 12; triangles). The mice were sacrificed day 4 after infection. The levels of TNF-α and IL-6 released from lung cells (LUNG) or present in the bronchoalveolar lavage (BAL) was measured by ELISA. Statistical calculations were made using 1-way ANOVA.

The results (FIG. 12) did not show any significant differences in TNF-α or IL-6 production between the various groups of influenza A-infected mice.

Example 8: Effect of ssONs on Secretion of IL-6 by MoDCs and Expression of CD86

MoDCs were treated with the TLR3 agonist poly I:C (25 µg/ml) in the absence or presence of 0.5 µM MedONs and incubated at +37° C. 48 h post treatments, the cells were harvested and stained for immuno-maturation marker CD86. MedON-01 and MedON-13-20 are able to inhibit poly I:C mediated immune-maturation. The results are shown in FIG. 13.

MoDCs were treated with the TLR3 agonist poly I:C (25 µg/ml) in the absence or presence of 0.5 µM MedONs and incubated at +37° C. 24 h post treatments, the supernatant was collected and assessed for secretion of the pro-inflammatory cytokine IL-6. MedON-01 and MedON-13-20 are able to inhibit poly I:C mediated induction of IL-6. The results are shown in FIG. 14.

Further Experimental Data
Experimental Methods for Further Experimental Data
Primary Human Cells Human Buffy coats were acquired from Karolinska Institutet, Stockholm, Sweden. All experimental work with human peripheral blood cells were carried out in accordance with Swedish guidelines and regulations. All experimental protocols were approved by the local ethical committee in Stockholm ("Regionala etikprövningsnämnden i Stockholm", Ethical permit Dnr 2006/229-31/3). According to regulations in Sweden, experimental in vitro work with cells from buffy coats does not require informed consent. Human monocytes were generated using the RosetteSep Monocyte Enrichment Kit (1 mL/10 mL buffy coat; StemCell Technologies) and differentiated into moDC, with GM-CSF (250 ng/mL; PeproTech) and IL-4 (6.5 ng/mL; R&D Systems) for 6 days in 37° C., 5% CO2 at a density of 5×105 cells/mL in RPMI 1640 completed with 10% FCS, 1 mM sodium pyruvate, 10 mM HEPES, 2 mM Lglutamine, and 1% streptomycin and penicillin (all from Invitrogen Life Technologies) as previously described (Sköld et al (2012). Differentiation of the cells was monitored by CD1a expression. PBMCs were isolated from buffy coats after Ficoll separation (Stemcell).

Oligonucleotides

Fully PS-substituted ssON 35 PS and 2'OMe PS/PO were made by Integrated DNA Technologies. Other modified oligonucleotides were purchased from Eurofins. For sequences, see Table 2. Total RNA was purified from moDC using RNeasy total RNA purification kit, according to manufacturer's instructions (Qiagen).

TLR Ligands and Labelled Endosomal Markers

TLR3 ligand pI:C (25 µg/mL unless otherwise stated), TLR7 ligand CL307 (1 µg/mL) and TLR7/8 ligand R848 (1 µg/mL) were all purchased from Invivogen. LPS (100 ng/ml) was purchased from Sigma. Transferrin-Alexa647, Dextran-Texas red 10 kDa, and LPS-Alexa488 were all purchased from Molecular probes. Cy3 labelled pI:C was generated using an oligonucleotide Label IT-kit (Mirus), according to manufacturer's instructions.

Uptake Studies in moDCs

MoDC were exposed to endosomal markers, with or without addition of ssON, on ice in complete 10% RPMI media (or serum free media for PO ON uptake studies), and then transferred to 37° C. for 45 min. Cells were washed with cold PBS and fixed (Cytofix, BD Bioscience). Fluorescent signal was monitored by flow cytometry (Fortessa, BD Biosciences). Data were analyzed with FlowJo software (Tree Star, version 9.6.4). CME was monitored by: 25 µg/ml Transferrin-Alexa647, 5 µg/ml LDL-Dil or 1 to 5 µg/ml pI:C-Cy3. MPC: 0.5 mg/ml 10 kDa Dextran-Texas-Red. Endocytic uptake of TLR4: 1 µg LPS-Alexa488. Transfection of pI:C-Cy3 was performed with LyoVec (Invivogen) in a ratio 1:6 according to manufacturer's instructions. For microscopy, moDC were adhered poly-L-lysine coated glass slides for 2-4 h. Cells were treated with ligands at 37° C. for 45 min in the presence or absence of 0.5 µM ssON 35 PS.

Cells were washed and acquired at 37° C. in a wide-field Cell Observer microscope (Zeiss) using the 40× lens. Images were acquired and analyzed using the SlideBook 6 program (Intelligent imaging innovations). Alternatively, cells were treated with Poly I:C-Cy3 and Poly I:C-Cy3 with LyoVec the presence or absence of 0.5 μM ssON 35 PS at 37° C. for 40 min, after cell adherence. Cells were washed with PBS and stained with Wheat Germ agglutinin Alexa633 (Invitrogen) for 10 min. Cells were washed prior to fixation in 3.7% Formaldehyde (Sigma). Images were acquired in a LSM800 airy scan confocal microscope (Zeiss) using the 63× oil lens and the images were analyzed using the Zen blue software (Zeiss).

MoDC Maturation Studies

MoDC were exposed to pI:C (25 μg/ml), CL307 (1 μg/ml), R848 (1 μg/ml) LPS (100 ng/ml), or pI:C/LyoVec (1 μg/ml) (Invivogen) with or without the addition of ssON, and assessed 48 h later by flow cytometry using monoclonal antibodies (Abs) targeting CD1a and the moDC maturation markers CD86, CD83, and CD80 (CD1a-Bv510, CD86-APC, CD83-FITC, CD80-PE; all from BD Biosciences). Where chloroquine was used, cells were pre-incubated with 10 μM chloroquine for 1 h at 37° C. Dead cells were excluded using Live/Dead fixable near-IR dead cell stain kit (Life Technologies).

Cytokine/Chemokine Secretion Studies

Supernatants were collected at given time points post treatment and secretion of cytokines/chemokines was measured by standard ELISA according to manufacturer's instructions (Mabtech; IL-6, IL-10, and IL-29. Life Technologies: CXCL10) by a SpectraMax i3x, Molecular devices.

TLR3 Activation Studies in HEK Cells

TLR3 transfected HEK-blue™ cells (Invivogen) were seeded at 20 000 cells/well in 384 well plate (Corning) and left to attach for 1 h. Cells were treated with 1 μg/ml pI:C, specified concentrations of ssON 35 PS and incubated over night. TLR3 activity was measured at 640 nm in HEK-blue™ detection medium (Invivogen) with the Envision Plate Reader (Perklin Elmer), and given as % of pI:C treated cells without ssON 35 PS.

Nuclease Degradation of ssON 35 PO and PS

Nuclease degradation was performed similarly to Ciafre et al. and carried out in serum free RPMI media. DNase I (Qiagen) was used at a ratio of 1 U/μg DNA. The reaction was carried out at 37° C. for 0-24 h at a concentration of 10 μM ssON 35 PO/PS. Aliquots were removed at given time-points, frozen at −80° C. and later analyzed on a 2% agarose gel. Electrophoresis was performed in TBE buffer for 1 h at 100V. The gel was stained with ethidium bromide (0.5 μg/ml) and photographed using a gel doc ez imager (Biorad).

Kinetic Analysis of TLR3 Inhibition

MoDC were exposed to 25 μg/ml pI:C/0.5 μM ssON 35 PS and then pulsed with either 0.5 μM ssON 35 PS or 25 μg/ml pI:C respectively over a time period from 5 min to 24 h. Cells were analyzed by flow cytometry 48 h post initial exposure for expression of maturation markers CD80 and CD86 in CD1a positive cells. Additionally, supernatants were collected 48 h post treatment and IL-6 was measured by ELISA (Mabtech).

Viability Test

Viable cells were assessed using a Live/Dead fixable near-IR dead cell stain kit 48 h post initial treatment with 25 μg/ml pI:C/0.5 μM ssON 35 PS according to manufacturer's protocol (Life Technologies). Data was acquired by Flow cytometry. WST-1 assay was preformed according to the manufacturer's protocol (Sigma) and measured on Spectra-Max i3x.

MoDC Maturation Studies with dsON

SsON 35 PS was pre-incubated at 5 μM with complementary ssON 35 PO at 1-10 μM in PBS at 55° C. and then left at ambient temperature for 30 min. ON mixture was added to moDC in a final concentration of 0.5 μM ssON 35 PS in combination with 25 μg/ml pI:C. MoDC maturation was assessed as described above.

RNA Sequencing and Differential Expression Analysis

Total RNA was purified from moDC using RNeasy total RNA purification kit, according to manufacturer's instructions (Qiagen) and submitted to the National Genomics Infrastructure Sweden Stockholm (NGI) for sequencing. Bioanalyzer traces and concentration values were obtained following the guidelines in the Sample requirements for genomics documentation available at the NGI website. The RNA sequencing was performed with the TruSeq RiboZero kit from Illumina.

Mass Spectrometry Based Proteomics Analysis of moDC

2×8 samples were collected at given timepoints, after moDC stimulation with either pI:C (25 μg/ml) or ssON 35 PS (0.5 μM), and snap frozen. For a complete Liquid chromatography tandem mass spectrometry (LC-MS/MS) analysis was performed using an Agilent 1200 nano-LC system coupled online to a Q Exactive Orbitrap (Thermo Fischer Scientific). The software Proteome Discoverer vs.1.4.0.288 including Sequest-Percolator for improved identification (Käll, L., et al (2007)) was used to search the data against the human Ensembl database (version 37) for protein identification (false discovery rate (FDR) of <1%).

Hierarchical Clustering and Network Generation

The analyses were performed using the software Morpheus (https://software.broadinstitute.org/morpheus/index-.html) on log 2 transformed data. Network analysis to identify directly interconnected genes within the hierarchical clusters was performed using MetaCore™ version 6.22 (Thomson Reuters), and results displayed using Cytoskape version 3.2.1 (Shannon P. et al (2003).

Animals and Injections

Adult cynomolgus macaques (*Macaca fascicularis*) (n=18, both females and males), were handled in accordance with European guidelines for NHP care (EU Directive N 63/2010). This study was approved and accredited under statement number 12-013 by the Ethical Animal Committee of the CEA "Comité d'Ethique en Experimentation Animale" registered by the French Research Ministry under number 44. Animals were handled under sedation and intradermal injections were done in the upper left and right back flank with 170 μg of pI:C alone or with 170 μg of ssON 35 PS in 100 μL of PBS, or PBS alone. Alternatively, a dose escalation with ssON 35 PS was performed as indicated in figure legends. Skin biopsies (8 mm in diameter) were collected from anesthetized animals 24 h after injection.

NHP Tissue Collection and Flow Cytometry

Cells were extracted from fresh skin biopsies collected 24 h after injections. Epidermal and dermal cells were stained with a mix of monoclonal antibodies (HLA-DRV500, CD123-PECy7, CD45-V450, CD11c-APC, CD14-APC-H7 from BD Bioscience; CD66-APC, CD66-FITC from Miltenyi; CD1a from DAKO; CD163-PcPCy5.5 from Biolegend) and acquired by flow cytometry.

Histochemistry

Live CD66+CD45+NHP cells were FACS-sorted (FACSAria, BD Biosciences) and put on Superfrost® Plus gold slides (Thermo Scientific) by cytospin and stained using Giemsa according to clinical routine procedures at the Clinical Pathology Laboratory at Karolinska University Hospital Huddinge.

Cytokine Secretion Assays

Aliquots of filtered-dermis supernatants isolated ex vivo, without further stimulation, were measured with the MILLIPLEX MAP NHP Cytokine Magnetic Bead Panel (Millipore, France) on a Bio-Plex device (Bio-Rad, France).

Microarray Analysis

Whole skin RNA was extracted from macaque skin biopsies. For detailed sample preparation and protocol, see supplementary Material and Methods section. RNA was hybridized to Agilent Rhesus Macaque Gene Expression Microarrays v2 for 17 h at 65° C. in a rotating Agilent hybridization oven. Microarrays were washed and scanned on the Agilent DNA Microarray Scanner (G2505C) using one color scan setting for 4×44K array slides (Scan Area 61×21.6 mm, Scan resolution 5 µm, Dye channel is set to Green, PMT is set to 100%). Images were analyzed with Feature Extraction Software 10.7.3.1 (Agilent) using default parameters to obtain a background adjusted signal (gProcessedSignal) for each gene. The signals were subsequently quantile normalized to increase inter-sample comparability.

Pathway Analysis

Ingenuity Pathway Analysis software (Build version 456367M, Content version 39480507 release date 20170914) (Ingenuity Systems) was used to identify canonical signalling pathways. To calculate significance of enrichment (Fisher's exact test, performed within the software), the reference molecule set was Ingenuity Knowledge Base (Genes only). Three input molecule sets depending on analysis; (i) proteome clusters of proteins with correlating expression (mass spectrometry data, human moDC in vitro) selected based on hierarchical clustering (ii) RNAseq data (human moDC in vitro) filtered by absolute log 2 fold change above 2 and (iii) microarray data from macaque skin biopsies filtered by absolute log 2 fold change above 5. Gene Ontology (GO) enrichment analyses were performed using the Gorilla (Gene Ontology enRIchment anaLysis and visuaLizAtion tool) web tool (Eden E. et al (2009)).

Quantification and Statistical Analysis

Non-parametric Kruskal-Wallis unpaired test followed by Dunn's post-test or Mann-Whitney test was used to compare the presented data in FIGS. 15-16 and FIG. 18B. Data for statistical calculations are from at least three donors in biological replicates in independent experiments. Data from macaque studies are shown for individual animals. Statistical calculations for transcriptomic and proteomic data are described above. P-value: not significant (n.s) P>0.05;* P≤0.05;  P≤0.01; * P≤0.001. Statistics were calculated using GraphPad Prism 7 software.

Further Experimental Data

Length Requirement of at Least 25 Bases for ssON's Capacity to Inhibit TLR3 Activation CpG motifs in DNA can bind to TLR9, leading to activation of TLR9+ cells such as plasmacytoid dendritic cells and B cells. We previously showed that a CpG containing ssON (35 bases) inhibited TLR3 activation in moDC lacking both TLR7 and TLR9 (Sköld et al (2012)). In the present study, we have exclusively used ssON without CpG motifs to address their capacity to inhibit TLR3 activation. To get further insight as to whether the observed inhibition of endocytosis and downstream TLR3 activation could be linked to a particular ssON sequence, three different sequences were compared (Table 2). SsON GtA 35 PS was based on the parent sequence ssON 35 PS, but all the guanosine (G) bases were substituted for adenosine (A), while ssON Compl 35 PS is the complementary sequence to ssON 35 PS. All displayed the same inhibitory effect in moDC treated with pI:C for 48 h (FIG. 15A). To get further insights to the structural requirement, we assessed if the length of ssON influences its efficacy. We found that shorter ssON (Table 2) did not possess the same inhibitory capability as longer versions, with a length cut off between 20 and 25 bases for effective ssON (FIGS. 15B and 15C). Therapeutic ssON for anti-sense purposes delivered without transfection agents (gymnotic delivery) are usually less than 20 bases (Soifer H S et al (2012) and Stein Calif. et al (2010)). Therefore, we next evaluated the uptake of ssON composed of 15 bases. Microscopy studies showed that fluorescently labelled ssON 15 PS was readily internalized by moDC and that this cellular uptake was efficiently blocked by the addition of ssON 35 PS (FIGS. 15D and 15E) in a concentration dependent manner (FIG. 15F). Hence, these data provide clues as to why therapeutic anti-sense ssON that rely on endocytic uptake should be shorter than 20 bases.

We next investigated whether the inhibitory effect is induced by other classes of extracellular nucleic acids, or if it requires ssON. In order to assess if the introduction of double-stranded (ds)DNA influences endocytic uptake, ssON 35 PS was kept at a constant concentration (0.5 µM), while increasing concentrations of a non-stabilized complementary strand (ssON Compl 35 PO) were introduced (FIG. 15G). MoDC were treated with pI:C and the inhibitory activity of the ssON was reduced when the complementary strand was introduced. The inhibitory effect was absent when all ssON 35 PS had a complementary strand to hybridize to (ssON Compl PO 1 µM). Naturally occurring PO ssON is degraded unless it can hybridize to ssON 35 PS. A PO backbone containing ssON (ssON 35 PO) had no inhibitory effect on pI:C-induced maturation 48 h post initial treatment, consistent with its degradation. The inhibitory effect of ssON 35 PS remained with the addition of non-complementary ssON 35 PO (FIG. 15G). Altogether, these data show that ssON, but not dsDNA, can inhibit endocytic uptake and downstream effects of the TLR3 agonist pI:C in a concentration dependent manner, and that the effects are not linked to a specific ssON sequence or motif. However, the inhibition is dependent on the length of the ssON, with a full effect reached at or above 25 bases.

Both ssDNA and ssRNA Inhibit Clathrin-Dependent Endocytic Pathways

To elucidate if the ability to inhibit endocytosis is exclusive for ssDNA, or if ssRNA also possess similar inhibitory capability, we synthesized a 35mer ON, comprised of the non-toxic, modification 2'-O-Methyl RNA (2'OMe) often found in ribosomal RNA and small nuclear RNAs (FIG. 16A) (Table 2). This ssON 2'OMe RNA analogue with a PS backbone effectively inhibited uptake of both TF and LPS (FIGS. 16B and 16C). As with ssDNA, 2'OMe ssRNA with an unmodified PO backbone could inhibit TF uptake albeit with a lower efficacy (FIG. 16D). Further evidence of transient inhibition was found by showing decreased IL-6 secretion from moDC after incubation with pI:C and ssON 2'OMe PS, with a reduction comparable to ssON 35 PS (FIG. 16E). In addition, purified total RNA (totRNA), using a cut off filter below 200 bases, reduced production of IL-6 in a concentration dependent manner, when measured after 3-4 h (FIG. 16F). These data show that ssON, with the capacity to temporarily inhibit clathrin-mediated endocytic uptake in human moDC, can be of either ssDNA or ssRNA origin.

No Major Changes in the Transcriptome or Proteome after Inhibition of Clathrin-Mediated Endocytosis in moDC To gain insight to the cellular response occurring after the shut-down of the clathrin-mediated endocytosis in moDC, we performed combined transcriptomic and proteomic studies after exposure to ssON (FIG. 17). These studies were also conducted after stimulation with pI:C with and without ssON, to get an overall picture of ssON capacity to inhibit TLR3 activation (FIG. 17). RNAseq analyses revealed that there was a strong upregulation of IFN-stimulated genes (ISG) but not inflammasome related genes (Barouch et al (2016)) in pI:C-stimulated moDC after 24 h (FIG. 17A). Ingenuity pathway analyses (IPA) showed upregulation of genes in the canonical pathways "Interferon signaling", "Role of Pattern Recognition Receptors in Recognition of Bacteria and Viruses" and "Crosstalk between Dendritic Cells and Natural Killer Cells" (FIG. 17A). The addition of ssON 35 PS abrogated the pI:C-mediated induction of ISGs, supporting an effective inhibition of TLR3 activation by ssON (FIG. 17B). Treatment with ssON 35 PS alone did not lead to any clear changes in the transcriptome, which was measured for up to 24 h (FIG. 17C).

The proteomic analyses similarly showed up-regulation of ISGs, but not inflammasome-related proteins in pI:C-stimulated moDC after 24 h (FIG. 17D). Proteomic analyses confirmed that ssON 35 PS abrogated pI:C-mediated induction of ISGs (FIG. 17E). Stimulation with ssON 35 PS alone did not lead to any major changes of the proteome (FIG. 17F). The time course of overall proteome changes in moDC was measured at seven timepoints; before stimulation, at 15, 30 and 60 min as well as 3, 8 and 24 h post treatment with ssON (data not shown). To select protein subsets with correlating protein expression levels for further interpretation of the data, hierarchical clustering and networks analyses were performed (FIG. 17). IPA analysis revealed that pI:C stimulation of moDC resulted in a clear time-dependent up-regulation of protein subsets linked to "Interferon signaling", "Role of Pattern Recognition Receptors in Recognition of Bacteria and Viruses" and "Crosstalk between Dendritic Cells and Natural Killer Cells" (FIG. 17D), in accordance with the RNAseq data and previous studies (Amit et al (2009) and Shalek et al (2014)). Up-regulated proteins after pI:C stimulation included MHC class I and class II molecules, and markers associated with moDC maturation, such as CD83 (data not shown). As expected, many molecules were detected that play a role after PRR engagements, interferon signaling and activation of IRF. Network analysis performed on the up-regulated cluster after pI:C stimulation identified IRF1, 7, 8 and STAT1 as the most interconnected proteins (>10 edges) (data not shown), whereas the protein-level changes following ssON stimulation were less pronounced (FIG. 17F). No clear trends or clusters could be detected in the protein subset of up- or down-regulated proteins after ssON stimulation of steady state human moDC. Altogether, these data show that stimulation of pI:C leads to up-regulation of ISGs detected at both the transcriptional and proteome level in moDC, while the addition of ssON blunted this response. Moreover, there were no major changes occurring in the transcriptome in moDC treated with ssON alone, with minor changes starting to occur in the proteome after 8-24 h. The lack of changes in the proteome and transcriptome does however not exclude that ssON induce other changes occurring in the cell. Modulations in the cytoskeleton, phosphorylation patterns or alterations in protein-protein interactions might all contribute to the SOMIE effect.

Administration of ssON 35 PS Modulates dsRNA-Mediated Inflammation in the Skin of Macaques To assess whether ssON 35 PS can mediate effects in vivo, we measured the local infiltration of cells and their innate immune signatures after intradermal injection of pI:C in the presence or absence of ssON 35 PS in macaque skin biopsies taken from the site of injection. Multicolor flow cytometry was used to phenotype cells isolated from epidermal and dermal layers (Adam et al (2015) and Epaulard et al (2014)) (FIG. 18) and revealed that injection of pI:C led to influx of polymorphonuclear neutrophils (PMN) and HLA-DR+ CD1− antigen presenting cells (APC), while addition of ssON reduced the infiltration of epidermal HLA-DR+ CD1a− cells, but not PMN (FIG. 18).

To assess the global innate response to pI:C in the presence or absence of ssON, transcriptional profiling was performed on the skin biopsies. IPA analyses revealed that several pathways for innate immunity, such as "Communication between Innate and Adaptive Immune Cells", "TREM1 signaling", "Role of Pattern Recognition Receptors in Recognition of Bacteria and Viruses", and "Crosstalk between Dendritic cells and Natural Killer cells", were engaged after injection of pI:C (FIG. 18). We next compared the group receiving intradermal injection of pI:C alone with the group receiving pI:C in combination with ssON, and calculated the fold change as well as significant differences between the two groups (FIG. 18A). The results show that among the top down-regulated genes, after addition of ssON 35 PS, are chemokines and genes implicated in inflammatory conditions (FIG. 18A). RC treatment alone resulted in significant induction of the chemokines Ccl5, Cxcl9, and Cxcl1 as well as Rax, a cellular activator for dsRNA-dependent serine/threonine protein kinase (Bennet R L et al (2006)), which were all significantly reduced with combined pI:C and ssON treatment (FIG. 18B). Similarly, Icam-1 and Lrg1, involved in cell adhesion, were upregulated in tissue after pI:C injection, but this induction was reduced by co-injection with ssON (FIG. 18B).

IFN-γ regulate many chemokines (Antonelli et al (2014)). PI:C injection indeed resulted in increased expression of both IFN-γ and IL-6, while the combined pI:C and ssON treatment reduced this expression in concordance with modulation of chemokine expression (FIG. 18B). To validate cytokine protein secretion in the skin, aliquots of filtered-dermis supernatant were collected and, without additional in vitro stimulation, analyzed using bioplex analyses (FIG. 18C). Significant induction of IL-6 and IFN-γ was detected after pI:C treatment. There was a clear trend that addition of ssON decreased IL-6 and IFN-γ production and instead provoked significant IL-10 release. Notably, ssON alone induced dose-dependent IL-10 secretion in vivo (FIG. 18C). Altogether, these findings show that there was a local dampened inflammatory signature in animals that received combined pI:C and ssON treatment as compared with pI:C alone, in agreement with ssON's ability to inhibit TLR3 activation.

TABLE 2

Primary structure of oligonucleotides.

| Name | Sequence | Length |
|---|---|---|
| ssON 35 PO | GAAGTTTTGAGGTTITGAAGTTGTTGGTGGTGGTG | 35 |
| ssON 35 PS | G*A*A*G*T*T*T*T*G*A*G*G*T*T*T*T*G*A*A*G*T*T*G*T*T*G*G*T*G*G*T*G*G*T*G | 35 |
| ssON 30 PS | A*G*T*T*T*T*G*A*G*G*T*T*T*T*G*A*A*G*T*T*G*T*T*G*G*T*G*G*T*G | 30 |
| ssON 25 PS | T*T*T*G*A*G*G*T*T*T*T*G*A*A*G*T*T*G*T*T*G*G*T*G*G | 25 |
| ssON 20 PS | T*G*A*G*G*T*T*T*T*G*A*A*G*T*T*G*T*T*G*G | 20 |
| ssON 15 PS | G*G*T*T*T*T*G*A*A*G*T*T*G*T*T | 15 |
| ssON GtA PS | A*A*A*A*T*T*T*T*A*A*A*A*T*T*T*T*A*A*A*A*T*T*A*T*T*A*A*T*A*A*T*A*A*T*A | 35 |
| ssON Compl PO | CACCACCACCAACAACTICAAAACCTCAAAACTTC | 35 |
| ssON Compl PS | C*A*C*C*A*C*C*A*C*C*A*A*C*A*A*C*T*T*C*A*A*A*A'A*C*C*T*C*A*A*A*A*C*T*T*C | 35 |
| ssON 2'OMe PO | *GAAGUUUUGAGGUUUUGARGUUGUUGGUGGUGGUG* | 35 |
| ssON 2'OMe PS | *G*A*A*G*U*U*U*U*G*A*G*G*U*U*U*U*G*A*A*G*U*U*G*U*U*G*G*U*G*G*U*G*G*U*G* | 35 |

All sequences written 5' to 3'  * = PS  *italic* = RNA  _ = 2'OMe

Discussion of Experimental Findings

Herein, we revealed that certain ssON can abolish uptake of ligands and thereby inhibit the activation of TLR3, 4 and 7 signaling endosomes, which supports and extends our previous publication that a CpG ssON (35 bases) inhibited TLR3 signaling (Sköld et al (2012)). We here also demonstrated that ssON block the uptake of TF, LDL, LPS and pI:C as shown by microscopy and quantified by flow cytometry. Functional inhibition of TLR3, 4 and 7 signaling was shown by measuring cytokine secretion and expression of co-stimulatory molecules from stimulated moDC and PBMC. We further assessed global changes by performing RNAseq and whole cell proteomic analyses, which support the block in endosomal signaling. Characterization of structural requirements for inhibition of clathrin-mediated endocytosis revealed that either ssDNA or ssRNA, but not dsDNA conferred the inhibition. The capability was not strictly dependent on the ssON sequence, but required that it was composed of at least 25 bases to have a full inhibitory effect. Hence, the inhibitory effect was not dependent on CpG motifs. We further provide evidence that ssON 35 PS modulated TLR3 activation in vivo in macaques by measuring local responses in the skin after injection.

The transient shut down of clathrin-mediated endocytosis did not severely hamper the cells. This was supported by the finding that cytokine secretion occurred in the presence of ssON provided that pI:C was taken up prior to the addition of ssON. Further, we show that ssON did not induce any apparent toxicity, and that it can rescue cells from pI:C-induced cell death. RNAseq and whole cell proteomic analyses supported this conclusion and no major changes occurred in the transcriptome or proteome after ssON treatment alone, which was measured for up to 24 h post stimulation. Injection of ssON in macaques did not induce inflammation, instead a dampening of dsRNA (pI:C)-mediated inflammation was observed. We also show that macropinocytosis (measured by uptake of dextran), was not affected by ssON, allowing continued uptake of nutrients in fluid phase.

Our findings that either ssDNA or ssRNA of at least 25 nucleotides have the capacity to temporarily (provided that they are not degraded) shut down clathrin-mediated endocytosis opens up intriguing questions in host-viral interactions, RNA biology and autoimmunity. Our data have implications for 1) viral endocytosis 2) cellular uptake of miRNA 3) role of stabilizing modifications of endogenous RNA 4) immune regulatory function of noncoding RNAs 5) development of ssON based therapeutics (anti-sense ONs, splice switching ONs, immunosuppressive ONs, siRNA, CpG adjuvant).

Altogether, these studies reveal a regulatory role for extracellular ssON in the endocytic uptake of TLR ligands and we have termed this regulatory process SOMIE (SsON-Mediated Interference of Endocytosis).

Infection by pathogens and cellular damages lead to an accumulation of extracellular nucleic acids that can be degraded by RNases and DNases, but also internalized into endosomes for subsequent TLR activation. To avoid excessive endosomal TLR activation under circumstances of heavy load on these systems, it is crucial to tightly control innate immune responses, thereby mitigating potential self-destructive events. An increasing number of molecules such as A20, CYLD, USP4, USP25, OTUB1/2, DUBA, and MYSM1 have been implicated in the dampening of intracellular signaling cascades triggered by PRR (Panda et al (2015)). However, there is a growing appreciation that the effects exerted by these enzymes cannot solely explain the rigorous regulation of PRR activation. Here we demonstrate that ssON, both native ssDNA and ssRNA 2'OMe, temporarily interfere with CME and downstream endosomal TLR activation. SOMIE serves as a regulatory process to temporarily limit activation of the innate immune system. Treatment with stabilized ssON 35 PS displayed a more prolonged block of endocytosis, while the MPC remained unaffected, showing that the inhibitory effect was specific for certain endocytic pathways. Phagocytosis is known to be controlled by both activating (prophagocytic; 'eat me') and inhibitory ('don't eat me') receptors. The inhibitory signal-regulatory protein (SIRP)α provides a blockade of phagocytosis after binding to the ligand CD47, a checkpoint of phagocytosis (Veilette et al (2018)).

Endocytosis of cargo was quantified by flow cytometry and visualized by microscopy, while functional activation of TLRs were measured by induction of costimulatory molecules CD80 and CD86 in moDC and secretion of cytokines. To reveal if ssON specifically affect activation from TLRs localized in endosomal compartments, we selected TLR agonists with distinct properties and assessed if ssON 35 PS inhibited secretion of IL-6. The TLR7/8 agonist R848 is membrane permeable (Govindaraj et al (2011)) and was not affected by the addition of ssON. In comparison, the activity of the endocytosis-dependent TLR7 agonist CL307 was significantly inhibited by ssON 35 PS. Furthermore, we studied LPS-sensing TLR4 that has two distinct signaling pathways in moDC. SsON 35 PS selectively decreased LPS-mediated secretion of IL-29/CXCL10, which is primarily downstream of TRIF and dependent on endocytosis, while it left the MyD88-dependent IL-6/IL-10 secretion unaffected. It remains to be further elucidated in which cell types TLR4 are coupled to both the Myd88 and TRIF signaling pathways and to reveal potential species differences.

Kinetic analyses revealed that the inhibitory capability of ssON 35 PS decreased if added more than 50 min post stimulation with pI:C and was almost negligible after 2 h. It therefore seems likely that ssON cannot inhibit ongoing TLR3 signaling. When treating moDC in the reverse fashion, starting with a single treatment of ssON 35 PS, pI:C-induced maturation was completely blocked for up to 24 h. PS substituted ssON have a half-life in serum-containing cell culture media that exceed 24 h (Ciafrè et al (1995)). PI:C, on the other hand, is rapidly degraded in serum containing media (Levy et al (1975)) and was not able to trigger TLR3 in moDC after pretreatment with ssON 35 PS. It can be envisioned that the interference with endocytic activity allows moDC to respond to cargo recently taken up, without receiving excessive additional stimulus or contra-orders prior to fulfilling the response to the first endocytosed cargo. In addition, the finding that moDC can mature and produce IL-6 production in the presence of ssON, provided that the cargo (pI:C) was first allowed to be taken up, suggests that a temporal shut-down of clathrin-mediated endocytosis does not severely impair the cell. Transcriptomic and proteomic moDC data provided further evidence that ssON effectively blunted the pI:Cmediated response and that no major changes occurred in ssON treated cells for up to 24 h.

We synthesized a panel of ON (Table 2) to determine the structural requirements for SOMIE. The SOMIE effect was not strictly dependent on the sequence or motif because the complementary strand to ssON 35 PS and a mutated ssON, in which all G were changed to A, showed similar efficacy. The interference with endosomal TLR activation by ssON was potent with an IC50 of about 150 nM. This led us to speculate that we are monitoring a biologically conserved function. However, to our knowledge the source of ssDNA in the cell is limited and primarily found in exosomes (Balaj et al (2011)), while ssRNA on the other hand are abundant. We demonstrated that a 35mer fully PS substituted RNA analogue 2'OMe ssON has the ability to block pI:C-induced moDC maturation and that total RNA (totRNA) inhibited pI:C-induced secretion of IL-6. Taken together, the SOMIE activity is not strictly dependent on ssON sequence, can occur with both ssDNA and ssRNA, and stability modifications (i.e. PS) are not essential for inhibition, but needed for retained activity over time. It remains to be further elucidated whether the metabolism of oligonucleotides and differential addition of stabilizing base modifications, such as 2'OMe or locked nucleic acid (LNA), can influence susceptibility to autoimmunity by setting the threshold of endosomal TLR activation.

The mammalian cell contains a plethora of both coding and non-coding ONs with varying lengths (Cech et al (2014)). Immuno-regulatory micro RNAs (miRNA) consist of 18-23 bases ssON (Mehta et al (2016)). However, cells also contain ssON that are longer in size (Cech et al (2014)). During cell death with release of cellular content, it is conceivable that both coding and non-coding DNA and RNA of varying length can be released into the extracellular space, becoming accessible to degradation by DNases and RNases. It can be postulated that the activity of these enzymes will greatly affect the size composition of ONs in the extracellular space, and ultimately affect triggering of nucleic acid sensing PRR. We here show that there is a length requirement of at least 20-25 bases to exert SOMIE activity. SsON (25-35 bases) inhibited uptake of shorter ssON (15 bases), while ssON 15 PS did not display SOMIE activity. This is consistent with recent data suggesting that miRNA (18-23 bases) released into the circulation and extracellular space during ischemia may instead trigger cytokine production via endosomal TLR7/MyD88 signaling (Feng et al (2017)). The revealed length requirement for SOMIE allude to an unknown function of longer non-coding RNAs and shows that miRNA are too short to provide endocytic checkpoint control.

Our finding that ssON of at least 20-25 bases interfere with endocytosis provides a rational as to why ssON used as antisense, or exon skipping ssON with gymnotic delivery, should be shorter than 20 bases to allow cellular uptake through endocytic pathways. Similarly, CpG ssON aimed for TLR9 agonistic actions should be less than 20 bases (Scheiermann et al (2014)), to avoid inhibition of endocytosis, which may inadvertently cause off-target effects in cells lacking TLR9 (Sköld et al (2012). It is conceivable that the size and the relative ds:ss composition of ON in the extracellular space will depend on the local microbial milieu, with an overflow of ON during infections. To our knowledge, there is currently no technique available to enable measurement of the intracellular or extracellular concentrations of naturally occurring ON with varying length. Hence, to what extent and the timeframes for the observed ssON-mediated TLR inhibition occurring by natural ligands cannot be truly estimated at the present time. Nevertheless, we provide evidence that ssON 35 PS exerted immunomodulatory effects in vivo after intradermal injection in macaques. Skin biopsies showed dampened pI:C-mediated inflammation in the dermis of macaques after injection of ssON and reduced secretion of IL-6 was confirmed in supernatants obtained from skin biopsies ex vivo (without additional in vitro stimulation). Notably, ssON induced dose-dependent IL-10 secretion in vivo, suggesting that inoculation with ssON may shift the direction of local immune responses. It remains to be elucidate which cell type(s) in the skin produce IL-10 after ssON treatment. We did not find any signs of IL-10 production in moDC in the genomic and proteomic studies after stimulation with ssON. We hypothesize that the local environment and cellular cross-talk might be pivotal for induction of IL-10 and a wide range of cell populations can be induced to produce human IL-10, including T cells (Tregs, Th1, Th2, and Th17), subsets of DC, macrophages, neutrophils, B cells, mast cells, fibroblasts, and keratinocytes (Berti et a; (2017)).

Immunosuppressive ssON have been suggested to dampen or prevent diseases characterized by pathologic immune stimulation and autoimmunity (Dong et al (2004); Klinman et al (2005); Peter et al (2008)). Several immunosuppressive ssON were previously shown to contain sequences or motifs required for direct binding, to for example, TLR7 or TLR9 (Bayik et al (2016) and Sarvestani et al (2015)), or repeats (TTAGGG) that interact with STAT1 and STAT4 (Shirota et al (2015)). We, and others, have previously suggested that TLR3 signaling can be inhibited by ssON in order to dampen over-reactive responses contributing to TLR3 linked pathogenesis (Skold et al (2012) and Ranjith-Kumar et al (2008)). Here we provide evidence that ssON might have a broader immune regulatory role than previously anticipated by acting as gatekeepers for uptake of cargo into endosomes, thereby providing a fluctuating threshold for potential autoimmune reactions triggered by endosomal TLR3/4/7 activation.

REFERENCES

Adam, L., Rosenbaum, P., Cosma, A., Le Grand, R. & Martinon, F. Identification of skin immune cells in non-human primates. J. Immunol. Methods 426, 42-49 (2015).

Akira, S. & Takeda, K. Toll-like receptor signalling. Nat. Rev. Immunol. 4, 499-511 (2004).

Amarante, M. K., Oda, J. M. M., Reiche, E. M. V., Morimoto, H. K., Aoki, M. N., Watanabe, M. A. E., 2011. Human endogenous RNAs: Implications for the immunomodulation of Toll-like receptor 3. Exp Ther Med 2, 925-929. doi:10.3892/etm.2011.303

Amarante, M. K., Watanabe, M. A. E., 2010. Toll-like receptor 3: involvement with exogenous and endogenous RNA. Int. Rev. Immunol. 29, 557-573. doi:10.3109/08830185.2010.525723

Amit, I. et al. Unbiased reconstruction of a mammalian transcriptional network mediating pathogen responses. Science 326, 257-263 (2009).

Antonelli, A. et al. Chemokine (C-X-C motif) ligand (CXCL) 10 in autoimmune diseases. Autoimmun Rev 13, 272-280 (2014).

Balaj, L., Lessard, R., Dai, L., Cho, Y.-J., Pomeroy, S. L., Breakefield, X. O., Skog, J., 2011. Tumour microvesicles contain retrotransposon elements and amplified oncogene sequences. Nature Communications 2, 180. doi:10.1038/ncomms1180

Barouch, D. H. et al. Rapid Inflammasome Activation following Mucosal SIV Infection of Rhesus Monkeys. Cell 165, 656-667 (2016).

Bayik, D., Gursel, I., Klinman, D. M., 2016. Structure, mechanism and therapeutic utility of immunosuppressive oligonucleotides. Pharmacol. Res. 105, 216-225. doi:10.1016/j.phrs.2015.11.010

Bennett, R. L. et al. RAX, the PKR activator, sensitizes cells to inflammatory cytokines, serum withdrawal, chemotherapy, and viral infection. Blood 108, 821-829 (2006).

Berti, F. C. B., Pereira, A. P. L., Cebinelli, G. C. M., Trugilo, K. P. & Brajão de Oliveira, K. The role of interleukin 10 in human papilloma virus infection and progression to cervical carcinoma. Cytokine Growth Factor Rev. 34, 1-13 (2017).

Cavassani, K. A. et al. TLR3 is an endogenous sensor of tissue necrosis during acute inflammatory events. J. Exp. Med. 205, 2609-2621 (2008).

Cech, T. R. & Steitz, J. A. The noncoding RNA revolution-trashing old rules to forge new ones. Cell 157, 77-94 (2014).

Choi, C. H. J., Hao, L., Narayan, S. P., Auyeung, E., Mirkin, C. A., 2013. Mechanism for the endocytosis of spherical nucleic acid nanoparticle conjugates. PNAS 110, 7625-7630. doi:10.1073/pnas.1305804110

Ciafrè, S. A., Rinaldi, M., Gasparini, P., Seripa, D., Bisceglia, L., Zelante, L., Farace, M. G., Fazio, V. M., 1995. Stability and functional effectiveness of phosphorothioate modified duplex DNA and synthetic 'mini-genes'. Nucleic Acids Res. 23, 4134-4142.

Cossart, P., Helenius, A., 2014. Endocytosis of viruses and bacteria. Cold Spring Harb Perspect Biol 6, a016972-a016972. doi:10.1101/cshperspect.a016972 de Bouteiller, O. et al. Recognition of double-stranded RNA by human toll-like receptor 3 and downstream receptor signaling requires multimerization and an acidic pH. J Biol Chem. 280, 38133-38145 (2005).

Doherty, G. J., McMahon, H. T., 2009. Mechanisms of endocytosis. Annu. Rev. Biochem. 78, 857-902. doi:10.1146/annurev.biochem.78.081307.110540

Dong, L., Ito, S.-I., Ishii, K. J., Klinman, D. M., 2004. Suppressive oligonucleotides protect against collagen-induced arthritis in mice. Arthritis Rheum. 50, 1686-1689. doi:10.1002/art.20263

Duan, Y., Zhang, S., Wang, B., Yang, B. & Zhi, D. The biological routes of gene delivery mediated by lipid-based non-viral vectors. Expert Opin Drug Deliv 6, 1351-1361 (2009).

Eden, E., Navon, R., Steinfeld, I., Lipson, D. & Yakhini, Z. GOrilla: a tool for discovery and visualization of enriched GO terms in ranked gene lists. BMC Bioinformatics 10, 48 (2009).

Epaulard, O. et al. Macrophage- and neutrophil-derived TNF-α instructs skin langerhans cells to prime antiviral immune responses. J. Immunol. 193, 2416-2426 (2014).

Feng, Y. et al. Extracellular MicroRNAs Induce Potent Innate Immune Responses via TLR7/MyD88-Dependent Mechanisms. J. Immunol. 199, 2106-2117 (2017).

Gitlin, L. et al. Essential role of mda-5 in type I IFN responses to polyriboinosinic:polyribocytidylic acid and encephalomyocarditis picornavirus. Proc. Natl. Acad. Sci. 103, 8459-8464 (2006).

Govindaraj, R. G., Manavalan, B., Basith, S., Choi, S., 2011. Comparative analysis of species-specific ligand recognition in Toll-like receptor 8 signaling: a hypothesis. PLoS ONE 6, e25118. doi:10.1371/journal.pone.0025118

Gursel, I., Gursel, M., Yamada, H., Ishii, K. J., Takeshita, F., Klinman, D. M., 2003. Repetitive elements in mammalian telomeres suppress bacterial DNA-induced immune activation. The Journal of Immunology 171, 1393-1400.

Husebye, H. et al. Endocytic pathways regulate Toll-like receptor 4 signaling and link innate and adaptive immunity. EMBO J. 25, 683-692 (2006).

Irannejad, R., Zastrow, von, M., 2014. GPCR signaling along the endocytic pathway. Curr. Opin. Cell Biol. 27, 109-116. doi:10.1016/j.ceb.2013.10.003

Isomura, I., Yasuda, Y., Tsujimura, K., Takahashi, T., Tochikubo, K., Morita, A., 2005. Recombinant cholera toxin B subunit activates dendritic cells and enhances antitumor immunity. Microbiol. Immunol. 49, 79-87.

Itoh, K., Watanabe, A., Funami, K., Seya, T., Matsumoto, M., 2008. The clathrin-mediated endocytic pathway participates in dsRNA-induced IFN-beta production. J. Immunol. 181, 5522-5529.

Juliano, R. L., Carver, K., 2015. Cellular uptake and intracellular trafficking of oligonucleotides. Advanced Drug Delivery Reviews 87, 35-45. doi:10.1016/j.addr.2015.04.005

Kagan, J. C., Su, T., Horng, T., Chow, A., Akira, S., Medzhitov, R., 2008. TRAM couples endocytosis of Toll-like receptor 4 to the induction of interferon-beta. Nature Publishing Group 9, 361-368. doi:10.1038/ni1569

Kato, H. et al. Cell type-specific involvement of RIG-I in antiviral response. Immunity 23, 19-28 (2005).

Kawai, T., Akira, S., 2010. The role of pattern-recognition receptors in innate immunity: update on Toll-like receptors. Nature Publishing Group 11, 373-384. doi:10.1038/ni.1863

Käll, L., Canterbury, J. D., Weston, J., Noble, W. S. & MacCoss, M. J. Semisupervised learning for peptide identification from shotgun proteomics datasets. Nat. Methods 4, 923-925 (2007).

Klein, D. C. G. et al. CD14, TLR4 and TRAM Show Different Trafficking Dynamics During LPS Stimulation. Traffic 16, 677-690 (2015).

Klinman, D. M., Gursel, I., Klaschik, S., Dong, L., Currie, D., Shirota, H., 2005. Therapeutic potential of oligonucleotides expressing immunosuppressive TTAGGG motifs. Ann. N. Y. Acad. Sci. 1058, 87-95. doi:10.1196/annals.1359.015

Kumari, S., Mg, S., Mayor, S., 2010. Endocytosis unplugged: multiple ways to enter the cell. Cell Res. 20, 256-275. doi:10.1038/cr.2010.19

Levy, H. B., Baer, G., Baron, S., Buckler, C. E., Gibbs, C. J., Iadarola, M. J., London, W. T., Rice, J., 1975. A modified polyriboinosinic-polyribocytidylic acid complex that induces interferon in primates. J. Infect. Dis. 132, 434-439.

Matsumoto, M., Oshiumi, H., Seya, T., 2011. Antiviral responses induced by the TLR3 pathway. Rev. Med. Virol. 21, 67-77. doi:10.1002/rmv.680

Mehta, A., Baltimore, D., 2016. MicroRNAs as regulatory elements in immune system logic. Nat Rev Immunol 16, 279-294. doi:10.1038/nri.2016.40

Merad, M., Sathe, P., Helft, J., Miller, J., Martha, A., 2013. The dendritic cell lineage: ontogeny and function of dendritic cells and their subsets in the steady state and the inflamed setting. Annu. Rev. Immunol. 31, 563-604. doi: 10.1146/annurev-immunol-020711-074950

Panda, S., Nilsson, J. A. & Gekara, N. O. Deubiquitinase MYSM1 Regulates Innate Immunity through Inactivation of TRAF3 and TRAF6 Complexes. Immunity 43, 647-659 (2015).

Pandey, S., Kawai, T. & Akira, S. Microbial sensing by Toll-like receptors and intracellular nucleic acid sensors. Cold Spring Harb Perspect Biol 7, a016246 (2014).

Pelka, K., Shibata, T., Miyake, K., Latz, E., 2016. Nucleic acid-sensing TLRs and autoimmunity: novel insights from structural and cell biology. Immunol. Rev. 269, 60-75. doi:10.1111/imr.12375

Peter, M., Bode, K., Lipford, G. B., Eberle, F., Heeg, K., Dalpke, A. H., 2008. Characterization of suppressive oligodeoxynucleotides that inhibit Toll-like receptor-9-mediated activation of innate immunity. Immunology 123, 118-128. doi:10.1111/.1365-2567.2007.02718.x Politz, J. C., Taneja, K. L., Singer, R. H., 1995. Characterization of hybridization between synthetic oligodeoxynucleotides and RNA in living cells. Nucleic Acids Res. 23, 4946-4953.

Rajaiah, R., Perkins, D. J., Ireland, D. D. C., Vogel, S. N., 2015. CD14 dependence of TLR4 endocytosis and TRIF signaling displays ligand specificity and is dissociable in endotoxin tolerance. PNAS 112, 8391-8396. doi:10.1073/pnas.1424980112

Ranjith-Kumar, C. T., Duffy, K. E., Jordan, J. L., Eaton-Bassiri, A., Vaughan, R., Hoose, S. A., Lamb, R. J., Sarisky, R. T., Kao, C. C., 2008. Single-stranded oligonucleotides can inhibit cytokine production induced by human toll-like receptor 3. Mol. Cell. Biol. 28, 4507-4519. doi:10.1128/MCB.00308-08

Roers, A., Hiller, B., Hornung, V., 2016. Recognition of Endogenous Nucleic Acids by the Innate Immune System. Immunity 44, 739-754. doi:10.1016/j.immuni.2016.04.002

Rosadini, C. V., Zanoni, I., Odendall, C., Green, E. R., Paczosa, M. K., Philip, N. H., Brodsky, I. E., Mecsas, J., Kagan, J. C., 2015. A Single Bacterial Immune Evasion Strategy Dismantles Both MyD88 and TRIF Signaling Pathways Downstream of TLR4. Cell Host and Microbe 18, 682-693. doi:10.1016/j.chom.2015.11.006

Sacre, S., Lo, A., Gregory, B., Stephens, M., Chamberlain, G., Stott, P., Brennan, F., 2015. Oligodeoxynucleotide inhibition of Toll-like receptors 3, 7, 8 and 9 suppresses cytokine production in a human rheumatoid arthritis model. Eur. J. Immunol. n/a-n/a. doi:10.1002/eji.201546123

Sarvestani, S. T. et al. Sequence-dependent off-target inhibition of TLR7/8 sensing by synthetic microRNA inhibitors. Nucleic Acids Res. 43, 1177-1188 (2015).

Scita, G., Di Fiore, P. P., 2010. The endocytic matrix. Nature 463, 464-473. doi:10.1038/nature08910

Scheiermann, J. & Klinman, D. M. Clinical evaluation of CpG oligonucleotides as adjuvants for vaccines targeting infectious diseases and cancer. Vaccine 32, 6377-6389 (2014).

Shalek, A. K. et al. Single-cell RNA-seq reveals dynamic paracrine control of cellular variation. Nature 510, 363-369 (2014).

Shannon, P. et al. Cytoscape: a software environment for integrated models of biomolecular interaction networks. Genome Res. 13, 2498-2504 (2003).

Sharma, V. K., Watts, J. K., 2015. Oligonucleotide therapeutics: chemistry, delivery and clinical progress. Future Med Chem 7, 2221-2242. doi:10.4155/fmc.15.144

Shirota, H., Gursel, I., Gursel, M., Klinman, D. M., 2005. Suppressive Oligodeoxynucleotides Protect Mice from Lethal Endotoxic Shock. The Journal of Immunology 174, 4579-4583. doi:10.4049/jimmunol.174.8.4579

Silva, A. C., Lopes, C. M., Sousa Lobo, J. M., Amaral, M. H., 2015. Nucleic Acids Delivery Systems: A Challenge for Pharmaceutical Technologists. Curr. Drug Metab. 16, 3-16.

Sköld, A. E., Hasan, M., Vargas, L., Saidi, H., Bosquet, N., Le Grand, R., Smith, C. I. E., Spetz, A.-L., 2012. Single-stranded DNA oligonucleotides inhibit TLR3-mediated responses in human monocyte-derived dendritic cells and in vivo in cynomolgus macaques. Blood 120, 768-777. doi:10.1182/blood-2011-12-397778

Smole, U., Radauer, C., Lengger, N., Svoboda, M., Rigby, N., Bublin, M., Gaier, S., Hoffmann-Sommergruber, K., Jensen-Jarolim, E., Mechtcheriakova, D., Breiteneder, H., 2015. The major birch pollen allergen Bet v 1 induces different responses in dendritic cells of birch pollen allergic and healthy individuals. PLoS ONE 10, e0117904. doi:10.1371/journal.pone.0117904

Soifer, H. S., Koch, T., Lai, J., Hansen, B., Hoeg, A., Oerum, H., Stein, C. A., 2012. Silencing of gene expression by gymnotic delivery of antisense oligonucleotides. Methods Mol. Biol. 815, 333-346. doi:10.1007/978-1-61779-424-7_25

Sorkin, A., Zastrow, von, M., 2009. Endocytosis and signalling: intertwining molecular networks. Nat. Rev. Mol. Cell Biol. 10, 609-622. doi:10.1038/nrm2748

Soulet, D., Covassin, L., Kaouass, M., Charest-Gaudreault, R., Audette, M., Poulin, R., 2002. Role of endocytosis in the internalization of spermidine-C(2)-BODIPY, a highly fluorescent probe of polyamine transport. Biochem. J. 367, 347-357. doi:10.1042/BJ20020764

Stein, C. A., Hansen, J. B., Lai, J., Wu, S., Voskresenskiy, A., Hog, A., Worm, J., Hedtjarn, M., Souleimanian, N., Miller, P., Soifer, H. S., Castanotto, D., Benimetskaya, L., (Drum, H., Koch, T., 2010. Efficient gene silencing by delivery of locked nucleic acid antisense oligonucleotides, unassisted by transfection reagents. Nucleic Acids Res. 38, e3-e3. doi:10.1093/nar/gkp841

Sun, R., Zhang, Y., Lv, Q., Liu, B., Jin, M., Zhang, W., He, Q., Deng, M., Liu, X., Li, G., Li, Y., Zhou, G., Xie, P., Xie, X., Hu, J., Duan, Z., 2011. Toll-like receptor 3 (TLR3) induces apoptosis via death receptors and mitochondria by up-regulating the transactivating p63 isoform alpha (TAP63alpha). J. Biol. Chem. 286, 15918-15928. doi: 10.1074/jbc.M110.178798

Takeda, K., Kaisho, T. & Akira, S. Toll-like receptors. Annu. Rev. Immunol. 21, 335-376 (2003).

Tatematsu, M., Yoshida, R., Morioka, Y., Ishii, N., Funami, K., Watanabe, A., Saeki, K., Seya, T., Matsumoto, M., 2016. Raftlin Controls Lipopolysaccharide-Induced TLR4 Internalization and TICAM-1 Signaling in a Cell Type-Specific Manner. J. Immunol. 196, 3865-3876. doi: 10.4049/jimmunol.1501734

Veillette, A. & Chen, J. SIRPα-CD47 Immune Checkpoint Blockade in Anticancer Therapy. Trends in Immunology 39, 173-184 (2018).

Vercammen, E., Staal, J., Beyaert, R., 2008. Sensing of viral infection and activation of innate immunity by toll-like receptor 3. Clin. Microbiol. Rev. 21, 13-25. doi:10.1128/CMR.00022-07

Weber, C., Müller, C., Podszuweit, A., Montino, C., Vollmer, J., Forsbach, A., 2012. Toll-like receptor (TLR) 3 immune modulation by unformulated small interfering RNA or DNA and the role of CD14 (in TLR-mediated effects). Immunology 136, 64-77. doi:10.1111/j.365-2567.2012.03559.x Zhu, F.-G., Reich, C. F., Pisetsky, D. S., 2002. Inhibition of murine macrophage nitric oxide production by synthetic oligonucleotides. J. Leukoc. Biol. 71, 686-694.

TABLE 1

Primary structure of oligonucleotides. All sequences are written 5' to 3'. All oligonucleotides were fully phosphorothioated (except MedON-02, 22, 23) and consist of deoxynucleotides (except MedON-08).

| Name | MedON# | Sequence (3'-5') * = PS _ = 2'Ome |
|---|---|---|
| ssON 35 PS | MedON01 | G*A*A*G*T*T*T*T*G*A*G*G*T*T*T*T*G*A*A*G*T*T*G*T*T*G*G*T*G*G*T*G |
| ssON 35 PO | MedON02 | GAAGTTTTGAGGTTTTGAAGTTGTTGGTGGTG |
| ssON 30 PS | MedON03 | A*G*T*T*T*T*G*A*G*G*T*T*T*T*G*A*A*G*T*T*G*T*T*G*G*T*G*G*T*G |
| ssON 25 PS | MedON04 | T*T*T*G*A*G*G*T*T*T*T*G*A*A*G*T*T*G*T*T*G*G*T*G*G |
| ssON 20 PS | MedON05 | T*G*A*G*G*T*T*T*T*G*A*A*G*T*T*A*T*T*G*G |
| ssON 15 PS | MedON06 | G*G*T*T*T*T*G*A*A*G*T*T*G*T*T |
| ssON 35 PS Complementary | MedON07 | C*A*C*C*A*C*C*A*C*C*A*A*C*A*A*C*T*T*C*A*A*A*A*C*C*T*C*A*A*A*A*C*T*T*C |
| ssON 35 2'OMe PS | MedON08 | G*A*A*G*U*U*U*U*G*A*G*G*U*U*U*U*G*A*A*G*U*U*G*U*U*G*G*U*G*G*U*G |
| ssON A-rich PS | MedON09 | A*A*A*A*T*A*A*A*A*T*A*A*A*A*T*A*A*A*A*T*A*A*A*A*T*A*A*A*A*T*A*A*A*A*T |
| ssON T-rich PS | MedON10 | T*T*T*T*T*T*T*T*T*T*T*T*T*T*T*T*T*T*T*T*T*T*T*T*T*T*T*T*T*T*T*T*T*T*T |
| ssON C-rich PS | MedON11 | C*C*C*C*T*C*C*C*C*T*C*C*C*C*T*C*C*C*C*T*C*C*C*C*T*C*C*C*C*T*C*C*C*C*T |
| ssON C-rich PS | MedON12 | G*G*G*A*A*G*G*G*A*A*G*G*G*A*A*G*G*G*A*A*G*G*G*A*A*G*G*G*A*A*G*G*G*A*A |
| G-ssON 35 0% PS | MedON13 | C*A*C*T*C*C*A*C*T*C*A*A*T*C*C*A*T*C*A*C*C*A*C*A*C*T*C*T*C*T*C*A*T*C*T |
| G-ssON 35 8% PS | MedON14 | G*A*C*T*C*C*A*C*T*C*A*A*T*C*C*A*T*C*A*C*C*A*C*A*C*T*C*T*G*T*G*A*T*C*T |
| G-ssON 35 15% PS | MedON15 | G*A*C*T*C*C*A*C*T*G*A*A*T*C*C*A*T*C*A*C*C*A*C*A*G*T*C*T*G*T*G*A*T*C*T |
| G-ssON 35 23% PS | MedON16 | G*A*G*T*C*C*C*A*C*T*G*A*A*T*C*C*A*T*G*A*C*C*A*C*A*G*T*C*T*G*T*G*A*T*G*T |
| G-ssON 35 29% PS | MedON17 | G*A*G*T*C*C*A*G*T*G*A*A*T*C*C*A*T*G*A*C*C*A*G*A*G*T*C*T*G*T*G*A*T*G*T |
| G-ssON 35 37% PS | MedON18 | G*A*G*T*C*C*A*G*T*G*A*A*T*G*G*A*T*G*A*C*C*A*G*A*G*T*G*T*G*T*G*A*T*G*T |
| G-ssON 35 49% PS | MedON19 | G*A*G*T*G*G*A*G*T*G*A*A*T*G*G*A*T*G*A*G*G*A*G*A*G*T*G*T*G*T*G*A*T*G*T |
| ssON 35 AT PS | MedON020 | A*A*T*T*A*A*T*T*A*T*A*T*A*T*A*T*A*A*T*A*T*A*A*T*T*A*A*T*T*A*A*A*T*A |
| ssON 70 PS | MedON21 | G*A*A*G*T*T*T*T*G*A*G*G*T*T*T*T*G*A*A*G*T*T*G*T*T*G*G*T*G*G*T*G*G*T*G* |
| ssON 35 3ePS | MedON22 | G*A*A*G*T*T*T*T*G*A*G*G*T*T*T*T*G*A*A*G*T*T*G*T*T*G*G*T*G*G*T*G*G*T*G<br>G*A*A*GTTTTGAGGTTTTGAAGTTGTTGGTGGTG*G*T*G |

TABLE 1-continued

Primary structure of oligonucleotides. All sequences are written 5' to 3'. All oligonucleotides were fully phosphorothioated (except MedON-02, 22, 23) and consist of deoxynucleotides (except MedON-08).

| | | |
|---|---|---|
| ssON 35 3eOMe | MedON23 | G*A*A*GTTTTGAGGTTTTGAAGTTGTTGGTGGTG*<u>G*T*G</u> |
| ssON GtA PS | MedON24 | A*A*A*A*T*T*T*A*A*A*A*T*T*T*T*A*A*A*A*T*T*A*T*T*A*A*T*A*A*T*A |

| Name | Length | Comment | SEQ ID No |
|---|---|---|---|
| ssON 35 PS | 35 | Also named: non-CpG | 1 |
| ssON 35 PO | 35 | | 2 |
| ssON 30 PS | 30 | | 3 |
| ssON 25 PS | 25 | | 4 |
| ssON 20 PS | 20 | | 5 |
| ssON 15 PS | 15 | | 6 |
| ssON 35 PS Complementary | 35 | | 7 |
| ssON 35 2'OMe PS | 35 | RNA analogue | 8 |
| ssON A-rich PS | 35 | | 9 |
| ssON T-rich PS | 35 | | 10 |
| ssON C-rich PS | 35 | | 11 |
| ssON C-rich PS | 35 | | 12 |
| G-ssON 35 0% PS | 35 | | 13 |
| G-ssON 35 8% PS | 35 | | 14 |
| G-ssON 35 15% PS | 35 | | 15 |
| G-ssON 35 23% PS | 35 | Also named: generic ssON 35 PS | 16 |
| G-ssON 35 29% PS | 35 | | 17 |
| G-ssON 35 37% PS | 35 | | 18 |
| G-ssON 35 49% PS | 35 | | 19 |
| ssON 35 AT PS | 35 | | 20 |
| ssON 70 PS | 70 | double ssON 3 PS | 21 |
| ssON 35 3ePS | 35 | | 22 |
| ssON 35 3eOMe | 35 | | 23 |
| ssON GtA PS | 35 | | 24 |

The invention claimed is:

1. A single-stranded oligonucleotide (ssON) that comprises or consists of a polynucleotide (i) having a sequence of any one of SEQ ID NOs: 13-21, or a complementary sequence thereof, wherein up to five nucleotides are replaced by another nucleotide; and/or (ii) having a sequence sharing at least 85% sequence identity with a sequence of any one of SEQ ID NOs: 13-21, or a complementary sequence thereof, wherein the ssON inhibits endocytosis, and wherein the ssON does not contain a CpG motif.

2. The ssON according to claim 1, wherein the ssON comprises or consists of a polynucleotide having a sequence of any one of SEQ ID NOs: 13-21, or a complementary sequence thereof.

3. The ssON according to claim 1, wherein the ssON comprises at least six phosphorothioate internucleotide linkages and at least six 2'-O-methyl modifications.

4. The ssON according to claim 1, wherein all internucleotide linkages in the ssON are phosphorothioate internucleotide linkages.

5. The ssON according to claim 1, wherein the length of the ssON is between 30 and 70 nucleotides.

6. The ssON according to claim 1, wherein not more than 16 consecutive nucleotides in the ssON are complementary with any human mRNA sequence and/or wherein the ssON is not self-complementary.

7. The ssON according to claim 1, wherein the ssON does not contain TTAGGG.

8. A pharmaceutical composition comprising the ssON according to claim 1, and a pharmaceutically acceptable carrier.

9. A composition comprising the ssON according to claim 1, and an additional therapeutic agent.

10. A method for preventing or treating an influenza virus infection in a subject, comprising administering a single-stranded oligonucleotide (ssON) to the subject,
wherein the ssON is one that inhibits endocytosis;
wherein the ssON does not contain a CpG motif; and
wherein the ssON is at least 25 nucleotides in length.

11. The method according to claim 10, wherein the ssON is one that modulates Toll-like receptor signalling, preferably wherein the ssON is one which inhibits TLR3 signalling.

12. The method according to claim 10, wherein either (i) at least 90% of the internucleotide linkages in the ssON are phosphorothioate internucleotide linkages; or (ii) the ssON comprises at least four phosphorothioate internucleotide linkages and at least four 2'-O-methyl modifications.

13. The method according to claim 10, wherein the length of the ssON is between 25 and 70 nucleotides.

14. The method according to claim 10, wherein not more than 16 consecutive nucleotides in the ssON are complementary with any human mRNA sequence and/or wherein the ssON is not self-complementary.

15. The method according to claim 10, wherein the monosaccharides in the ssON are selected from the group consisting of 2'-deoxyribose and 2'-O-methylribose.

16. The method according to claim 10, wherein the ssON does not contain TTAGGG.

17. The method according to claim 10, wherein the ssON is administered as a monotherapy.

18. The method according to claim 10, wherein the subject is administered an additional therapeutic agent.

19. The method according to claim 10, wherein the subject is not administered poly (I:C).

* * * * *

UNITED STATES PATENT AND TRADEMARK OFFICE
CERTIFICATE OF CORRECTION

PATENT NO. : 11,345,916 B2
APPLICATION NO. : 16/644151
DATED : May 31, 2022
INVENTOR(S) : Peter Järver et al.

It is certified that error appears in the above-identified patent and that said Letters Patent is hereby corrected as shown below:

In the Claims

In Column 79, Claim 6, Line 24, please unbold the number "16";

In Column 80, Claim 10, Line 1, please delete the words "preventing or";

In Column 80, Claim 10, Line 5, please delete the word "and"; and

In Column 80, Claim 10, Line 6, please delete "." after length, and add ---; and wherein the ssON is a ssON of claim 32.---.

Signed and Sealed this
Twenty-sixth Day of July, 2022

Katherine Kelly Vidal
*Director of the United States Patent and Trademark Office*

SEQUENCE LISTING

<160> NUMBER OF SEQ ID NOS: 34

<210> SEQ ID NO 1
<211> LENGTH: 35
<212> TYPE: DNA
<213> ORGANISM: Artificial Sequence
<220> FEATURE:
<223> OTHER INFORMATION: ssON 35 PS
<220> FEATURE:
<221> NAME/KEY: misc_feature
<222> LOCATION: (1)..(35)
<223> OTHER INFORMATION: /note="Phosphorothioate linkages"

```
<400> SEQUENCE: 1
gaagttttga ggttttgaag ttgttggtgg tggtg                              35

<210> SEQ ID NO 2
<211> LENGTH: 35
<212> TYPE: DNA
<213> ORGANISM: Artificial Sequence
<220> FEATURE:
<223> OTHER INFORMATION: ssON 35 PO

<400> SEQUENCE: 2
gaagttttga ggttttgaag ttgttggtgg tggtg                              35

<210> SEQ ID NO 3
<211> LENGTH: 30
<212> TYPE: DNA
<213> ORGANISM: Artificial Sequence
<220> FEATURE:
<223> OTHER INFORMATION: ssON 30 PS
<220> FEATURE:
<221> NAME/KEY: misc_feature
<222> LOCATION: (1)..(30)
<223> OTHER INFORMATION: /note="Phosphorothioate linkages"

<400> SEQUENCE: 3
agttttgagg ttttgaagtt gttggtggtg                                   30

<210> SEQ ID NO 4
<211> LENGTH: 25
<212> TYPE: DNA
<213> ORGANISM: Artificial Sequence
<220> FEATURE:
<223> OTHER INFORMATION: ssON 25 PS
<220> FEATURE:
<221> NAME/KEY: misc_feature
<222> LOCATION: (1)..(25)
<223> OTHER INFORMATION: /note="Phosphorothioate linkages"

<400> SEQUENCE: 4
tttgaggttt tgaagttgtt ggtgg                                        25

<210> SEQ ID NO 5
<211> LENGTH: 20
<212> TYPE: DNA
<213> ORGANISM: Artificial Sequence
<220> FEATURE:
<223> OTHER INFORMATION: ssON 20 PS
<220> FEATURE:
<221> NAME/KEY: misc_feature
<222> LOCATION: (1)..(20)
<223> OTHER INFORMATION: /note="Phosphorothioate linkages"

<400> SEQUENCE: 5
tgaggttttg aagttattgg                                              20

<210> SEQ ID NO 6
<211> LENGTH: 15
<212> TYPE: DNA
<213> ORGANISM: Artificial Sequence
<220> FEATURE:
<223> OTHER INFORMATION: ssON 15 PS
<220> FEATURE:
<221> NAME/KEY: misc_feature
<222> LOCATION: (1)..(15)
<223> OTHER INFORMATION: /note="Phosphorothioate linkages"

<400> SEQUENCE: 6
```
ggttttgaag ttgtt                                                    15

<210> SEQ ID NO 7
<211> LENGTH: 35
<212> TYPE: DNA
<213> ORGANISM: Artificial Sequence
<220> FEATURE:
<223> OTHER INFORMATION: ssON 35 PS Complementary
<220> FEATURE:
<221> NAME/KEY: misc_feature
<222> LOCATION: (1)..(35)
<223> OTHER INFORMATION: /note="Phosphorothioate linkages"

<400> SEQUENCE: 7
caccaccacc aacaacttca aaacctcaaa acttc                              35

<210> SEQ ID NO 8
<211> LENGTH: 35
<212> TYPE: RNA
<213> ORGANISM: Artificial Sequence
<220> FEATURE:
<223> OTHER INFORMATION: ssON 35 2OMe PS
<220> FEATURE:
<221> NAME/KEY: modified_base
<222> LOCATION: (1)..(1)
<223> OTHER INFORMATION: /mod_base="gm"
<220> FEATURE:
<221> NAME/KEY: misc_feature
<222> LOCATION: (1)..(35)
<223> OTHER INFORMATION: /note="Phosphorothioate linkages"
<220> FEATURE:
<221> NAME/KEY: modified_base
<222> LOCATION: (2)..(3)
<223> OTHER INFORMATION: /mod_base="OTHER" /note="2'-O-methyladenosine"
<220> FEATURE:
<221> NAME/KEY: modified_base
<222> LOCATION: (4)..(4)
<223> OTHER INFORMATION: /mod_base="gm"
<220> FEATURE:
<221> NAME/KEY: modified_base
<222> LOCATION: (5)..(8)
<223> OTHER INFORMATION: /mod_base="OTHER" /note="2'-O-methyluridine"
<220> FEATURE:
<221> NAME/KEY: modified_base
<222> LOCATION: (9)..(9)
<223> OTHER INFORMATION: /mod_base="gm"
<220> FEATURE:
<221> NAME/KEY: modified_base
<222> LOCATION: (10)..(10)
<223> OTHER INFORMATION: /mod_base="OTHER" /note="2'-O-methyladenosine "
<220> FEATURE:
<221> NAME/KEY: modified_base
<222> LOCATION: (11)..(12)
<223> OTHER INFORMATION: /mod_base="gm"
<220> FEATURE:
<221> NAME/KEY: modified_base
<222> LOCATION: (13)..(16)
<223> OTHER INFORMATION: /mod_base="OTHER" /note="2'-O-methyluridine "
<220> FEATURE:
<221> NAME/KEY: modified_base
<222> LOCATION: (17)..(17)
<223> OTHER INFORMATION: /mod_base="gm"
<220> FEATURE:
<221> NAME/KEY: modified_base
<222> LOCATION: (18)..(19)
<223> OTHER INFORMATION: /mod_base="OTHER" /note="2'-O-methyladenosine "
<220> FEATURE:
<221> NAME/KEY: modified_base
<222> LOCATION: (20)..(20)
<223> OTHER INFORMATION: /mod_base="gm"
<220> FEATURE:
<221> NAME/KEY: modified_base
<222> LOCATION: (21)..(22)
<223> OTHER INFORMATION: /mod_base="OTHER" /note="2'-O-methyluridine "
<220> FEATURE:
<221> NAME/KEY: modified_base -continued

```
<222> LOCATION: (23)..(23)
<223> OTHER INFORMATION: /mod_base="gm"
<220> FEATURE:
<221> NAME/KEY: modified_base
<222> LOCATION: (24)..(25)
<223> OTHER INFORMATION: /mod_base="OTHER" /note="2'-O-methyluridine "
<220> FEATURE:
<221> NAME/KEY: modified_base
<222> LOCATION: (26)..(27)
<223> OTHER INFORMATION: /mod_base="gm"
<220> FEATURE:
<221> NAME/KEY: modified_base
<222> LOCATION: (28)..(28)
<223> OTHER INFORMATION: /mod_base="OTHER" /note="2'-O-methyluridine "
<220> FEATURE:
<221> NAME/KEY: modified_base
<222> LOCATION: (29)..(30)
<223> OTHER INFORMATION: /mod_base="gm"
<220> FEATURE:
<221> NAME/KEY: modified_base
<222> LOCATION: (31)..(31)
<223> OTHER INFORMATION: /mod_base="OTHER" /note="2'-O-methyluridine "
<220> FEATURE:
<221> NAME/KEY: modified_base
<222> LOCATION: (32)..(33)
<223> OTHER INFORMATION: /mod_base="gm"
<220> FEATURE:
<221> NAME/KEY: modified_base
<222> LOCATION: (34)..(34)
<223> OTHER INFORMATION: /mod_base="OTHER" /note="2'-O-methyluridine "
<220> FEATURE:
<221> NAME/KEY: modified_base
<222> LOCATION: (35)..(35)
<223> OTHER INFORMATION: /mod_base="gm"

<400> SEQUENCE: 8
gaaguuuuga gguuuugaag uuguuggugg uggug                              35

<210> SEQ ID NO 9
<211> LENGTH: 35
<212> TYPE: DNA
<213> ORGANISM: Artificial Sequence
<220> FEATURE:
<223> OTHER INFORMATION: ssON A-rich PS
<220> FEATURE:
<221> NAME/KEY: misc_feature
<222> LOCATION: (1)..(35)
<223> OTHER INFORMATION: /note="Phosphorothioate linkages"

<400> SEQUENCE: 9
aaaataaaat aaaataaaat aaaataaaat aaaat                              35

<210> SEQ ID NO 10
<211> LENGTH: 35
<212> TYPE: DNA
<213> ORGANISM: Artificial Sequence
<220> FEATURE:
<223> OTHER INFORMATION: ssON T-rich PS
<220> FEATURE:
<221> NAME/KEY: misc_feature
<222> LOCATION: (1)..(35)
<223> OTHER INFORMATION: /note="Phosphorothioate linkages"

<400> SEQUENCE: 10
tttttttttt tttttttttt tttttttttt ttttt                              35

<210> SEQ ID NO 11
<211> LENGTH: 35
<212> TYPE: DNA
<213> ORGANISM: Artificial Sequence
<220> FEATURE:
<223> OTHER INFORMATION: ssON C-rich PS
<220> FEATURE:
```

<221> NAME/KEY: misc_feature
<222> LOCATION: (1)..(35)
<223> OTHER INFORMATION: /note="Phosphorothioate linkages"

<400> SEQUENCE: 11 ccctccctt cccctccct cccctccct ccct                       35

<210> SEQ ID NO 12
<211> LENGTH: 35
<212> TYPE: DNA
<213> ORGANISM: Artificial Sequence
<220> FEATURE:
<223> OTHER INFORMATION: ssON G-rich PS
<220> FEATURE:
<221> NAME/KEY: misc_feature
<222> LOCATION: (1)..(35)
<223> OTHER INFORMATION: /note="Phosphorothioate linkages"

<400> SEQUENCE: 12
gggaagggaa gggaagggaa gggaagggaa gggaa                       35

<210> SEQ ID NO 13
<211> LENGTH: 35
<212> TYPE: DNA
<213> ORGANISM: Artificial Sequence
<220> FEATURE:
<223> OTHER INFORMATION: G-ssON 35 0% PS
<220> FEATURE:
<221> NAME/KEY: misc_feature
<222> LOCATION: (1)..(35)
<223> OTHER INFORMATION: /note="Phosphorothioate linkages"

<400> SEQUENCE: 13
cactccactc aatccatcac cacactctct catct                       35

<210> SEQ ID NO 14
<211> LENGTH: 35
<212> TYPE: DNA
<213> ORGANISM: Artificial Sequence
<220> FEATURE:
<223> OTHER INFORMATION: G-ssON 35 8% PS
<220> FEATURE:
<221> NAME/KEY: misc_feature
<222> LOCATION: (1)..(35)
<223> OTHER INFORMATION: /note="Phosphorothioate linkages"

<400> SEQUENCE: 14
gactccactc aatccatcac cacactctgt gatct                       35

<210> SEQ ID NO 15
<211> LENGTH: 35
<212> TYPE: DNA
<213> ORGANISM: Artificial Sequence
<220> FEATURE:
<223> OTHER INFORMATION: G-ssON 35 15% PS
<220> FEATURE:
<221> NAME/KEY: misc_feature
<222> LOCATION: (1)..(35)
<223> OTHER INFORMATION: /note="Phosphorothioate linkages"

<400> SEQUENCE: 15
gactccactg aatccatcac cacagtctgt gatct                       35

<210> SEQ ID NO 16
<211> LENGTH: 35
<212> TYPE: DNA
<213> ORGANISM: Artificial Sequence
<220> FEATURE:
<223> OTHER INFORMATION: G-ssON 35 23% PS

```
<220> FEATURE:
<221> NAME/KEY: misc_feature
<222> LOCATION: (1)..(35)
<223> OTHER INFORMATION: /note="Phosphorothioate linkages"

<400> SEQUENCE: 16
gagtccactg aatccatgac cacagtctgt gatgt                                   35

<210> SEQ ID NO 17
<211> LENGTH: 35
<212> TYPE: DNA
<213> ORGANISM: Artificial Sequence
<220> FEATURE:
<223> OTHER INFORMATION: G-ssON 35 29% PS
<220> FEATURE:
<221> NAME/KEY: misc_feature
<222> LOCATION: (1)..(35)
<223> OTHER INFORMATION: /note="Phosphorothioate linkages"

<400> SEQUENCE: 17
gagtccagtg aatccatgac cagagtctgt gatgt                                   35

<210> SEQ ID NO 18
<211> LENGTH: 35
<212> TYPE: DNA
<213> ORGANISM: Artificial Sequence
<220> FEATURE:
<223> OTHER INFORMATION: G-ssON 35 37% PS
<220> FEATURE:
<221> NAME/KEY: misc_feature
<222> LOCATION: (1)..(35)
<223> OTHER INFORMATION: /note="Phosphorothioate linkages"

<400> SEQUENCE: 18
gagtccagtg aatggatgac caaggtgtgt gatgt                                   35

<210> SEQ ID NO 19
<211> LENGTH: 35
<212> TYPE: DNA
<213> ORGANISM: Artificial Sequence
<220> FEATURE:
<223> OTHER INFORMATION: G-ssON 35 49% PS
<220> FEATURE:
<221> NAME/KEY: misc_feature
<222> LOCATION: (1)..(35)
<223> OTHER INFORMATION: /note="Phosphorothioate linkages"

<400> SEQUENCE: 19
gagtggagtg aatggatgag gagagtgtgt gatgt                                   35

<210> SEQ ID NO 20
<211> LENGTH: 35
<212> TYPE: DNA
<213> ORGANISM: Artificial Sequence
<220> FEATURE:
<223> OTHER INFORMATION: ssON 35 AT PS
<220> FEATURE:
<221> NAME/KEY: misc_feature
<222> LOCATION: (1)..(35)
<223> OTHER INFORMATION: /note="Phosphorothioate linkages"

<400> SEQUENCE: 20
aattaattat aatatatata atattaataa taata                                   35

<210> SEQ ID NO 21
<211> LENGTH: 70
<212> TYPE: DNA
<213> ORGANISM: Artificial Sequence
<220> FEATURE:
```

<223> OTHER INFORMATION: ssON 70 PS
<220> FEATURE:
<221> NAME/KEY: misc_feature
<222> LOCATION: (1)..(70)
<223> OTHER INFORMATION: /note="Phosphorothioate linkages"

<400> SEQUENCE: 21
gaagttttga ggttttgaag ttgttggtgg tgtggaagt tttgaggttt tgaagttgtt       60
ggtggtggtg                                                             70

<210> SEQ ID NO 22
<211> LENGTH: 35
<212> TYPE: DNA
<213> ORGANISM: Artificial Sequence
<220> FEATURE:
<223> OTHER INFORMATION: ssON 35 3ePS
<220> FEATURE:
<221> NAME/KEY: misc_feature
<222> LOCATION: (1)..(3)
<223> OTHER INFORMATION: /note="Phosphorothioate linkages"
<220> FEATURE:
<221> NAME/KEY: misc_feature
<222> LOCATION: (33)..(35)
<223> OTHER INFORMATION: /note="Phosphorothioate linkages"

<400> SEQUENCE: 22
gaagttttga ggttttgaag ttgttggtgg tggtg                                 35

<210> SEQ ID NO 23
<211> LENGTH: 35
<212> TYPE: DNA
<213> ORGANISM: Artificial Sequence
<220> FEATURE:
<223> OTHER INFORMATION: ssON 35 3eOMe
<220> FEATURE:
<221> NAME/KEY: modified_base
<222> LOCATION: (1)..(1)
<223> OTHER INFORMATION: /mod_base="gm"
<220> FEATURE:
<221> NAME/KEY: misc_feature
<222> LOCATION: (1)..(3)
<223> OTHER INFORMATION: /note="Phosphorothioate linkages"
<220> FEATURE:
<221> NAME/KEY: modified_base
<222> LOCATION: (2)..(3)
<223> OTHER INFORMATION: /mod_base="OTHER" /note="2'-O-methyladenosine"
<220> FEATURE:
<221> NAME/KEY: modified_base
<222> LOCATION: (33)..(33)
<223> OTHER INFORMATION: /mod_base="gm"
<220> FEATURE:
<221> NAME/KEY: misc_feature
<222> LOCATION: (33)..(35)
<223> OTHER INFORMATION: /note="Phosphorothioate linkages"
<220> FEATURE:
<221> NAME/KEY: modified_base
<222> LOCATION: (34)..(34)
<223> OTHER INFORMATION: /mod_base="OTHER" /note="2'-O-methylthymidine "
<220> FEATURE:
<221> NAME/KEY: modified_base
<222> LOCATION: (35)..(35)
<223> OTHER INFORMATION: /mod_base="gm"

<400> SEQUENCE: 23
gaagttttga ggttttgaag ttgttggtgg tggtg                                 35

<210> SEQ ID NO 24
<211> LENGTH: 35
<212> TYPE: DNA
<213> ORGANISM: Artificial Sequence
<220> FEATURE:
<223> OTHER INFORMATION: ssON GtA PS

```
<220> FEATURE:
<221> NAME/KEY: misc_feature
<222> LOCATION: (1)..(35)
<223> OTHER INFORMATION: /note="Phosphorothioate linkages"

<400> SEQUENCE: 24
aaaattttaa aattttaaaa ttattaataa taata                                35

<210> SEQ ID NO 25
<211> LENGTH: 35
<212> TYPE: DNA
<213> ORGANISM: Artificial Sequence
<220> FEATURE:
<223> OTHER INFORMATION: CpG ssON

<400> SEQUENCE: 25
gtcgttttgt cgttttgtcg ttgttggtgg tggtg                                35

<210> SEQ ID NO 26
<211> LENGTH: 23
<212> TYPE: DNA
<213> ORGANISM: Artificial Sequence
<220> FEATURE:
<223> OTHER INFORMATION: Forward primer IAV HA segment

<400> SEQUENCE: 26
ggctgctttg aattttacca caa                                             23

<210> SEQ ID NO 27
<211> LENGTH: 25
<212> TYPE: DNA
<213> ORGANISM: Artificial Sequence
<220> FEATURE:
<223> OTHER INFORMATION: Reverse primer IAV HA segment

<400> SEQUENCE: 27
tttgggtagt cataagtccc atttt                                           25

<210> SEQ ID NO 28
<211> LENGTH: 27
<212> TYPE: DNA
<213> ORGANISM: Artificial Sequence
<220> FEATURE:
<223> OTHER INFORMATION: IAV HA segment probe
<220> FEATURE:
<221> NAME/KEY: misc_feature
<222> LOCATION: (1)..(1)
<223> OTHER INFORMATION: /note="FAM"
<220> FEATURE:
<221> NAME/KEY: misc_feature
<222> LOCATION: (27)..(27)
<223> OTHER INFORMATION: /note="TAMRA"

<400> SEQUENCE: 28
tgcgataaca cgtgcatgga aagtgtc                                         27

<210> SEQ ID NO 29
<211> LENGTH: 26
<212> TYPE: DNA
<213> ORGANISM: Artificial Sequence
<220> FEATURE:
<223> OTHER INFORMATION: Forward primer influenza M gene

<400> SEQUENCE: 29
aagacaagac caatyctgtc acctct                                          26

<210> SEQ ID NO 30
```

```
<211> LENGTH: 20
<212> TYPE: DNA
<213> ORGANISM: Artificial Sequence
<220> FEATURE:
<223> OTHER INFORMATION: Reverse primer influenza M gene

<400> SEQUENCE: 30
tctacgytgc agtccycgct                                                      20

<210> SEQ ID NO 31
<211> LENGTH: 21
<212> TYPE: DNA
<213> ORGANISM: Artificial Sequence
<220> FEATURE:
<223> OTHER INFORMATION: Influenza M gene probe
<220> FEATURE:
<221> NAME/KEY: misc_feature
<222> LOCATION: (1)..(1)
<223> OTHER INFORMATION: /note="FAM"
<220> FEATURE:
<221> NAME/KEY: misc_feature
<222> LOCATION: (21)..(21)
<223> OTHER INFORMATION: /note="TAMRA"

<400> SEQUENCE: 31
tyacgctcac cgtgcccagt g                                                    21

<210> SEQ ID NO 32
<211> LENGTH: 35
<212> TYPE: DNA
<213> ORGANISM: Artificial Sequence
<220> FEATURE:
<223> OTHER INFORMATION: Non-CpG ssON

<400> SEQUENCE: 32
gaagttttga ggttttgaag ttgttggtgg tggtg                                     35

<210> SEQ ID NO 33
<211> LENGTH: 35
<212> TYPE: DNA
<213> ORGANISM: Artificial Sequence
<220> FEATURE:
<223> OTHER INFORMATION: ssON Compl PO

<400> SEQUENCE: 33
caccaccacc aacaacttca aaacctcaaa acttc                                     35

<210> SEQ ID NO 34
<211> LENGTH: 35
<212> TYPE: RNA
<213> ORGANISM: Artificial Sequence
<220> FEATURE:
<223> OTHER INFORMATION: ssON 35 2OMe PO
<220> FEATURE:
<221> NAME/KEY: modified_base
<222> LOCATION: (1)..(1)
<223> OTHER INFORMATION: /mod_base="gm"
<220> FEATURE:
<221> NAME/KEY: modified_base
<222> LOCATION: (2)..(3)
<223> OTHER INFORMATION: /mod_base="OTHER" /note="2'-O-methyladenosine"
<220> FEATURE:
<221> NAME/KEY: modified_base
<222> LOCATION: (4)..(4)
<223> OTHER INFORMATION: /mod_base="gm"
<220> FEATURE:
<221> NAME/KEY: modified_base
<222> LOCATION: (5)..(8)
<223> OTHER INFORMATION: /mod_base="OTHER" /note="2'-O-methyluridine"
<220> FEATURE:
<221> NAME/KEY: modified_base
```

```
<222> LOCATION: (9)..(9)
<223> OTHER INFORMATION: /mod_base="gm"
<220> FEATURE:
<221> NAME/KEY: modified_base
<222> LOCATION: (10)..(10)
<223> OTHER INFORMATION: /mod_base="OTHER" /note="2'-O-methyladenosine "
<220> FEATURE:
<221> NAME/KEY: modified_base
<222> LOCATION: (11)..(12)
<223> OTHER INFORMATION: /mod_base="gm"
<220> FEATURE:
<221> NAME/KEY: modified_base
<222> LOCATION: (13)..(16)
<223> OTHER INFORMATION: /mod_base="OTHER" /note="2'-O-methyluridine "
<220> FEATURE:
<221> NAME/KEY: modified_base
<222> LOCATION: (17)..(17)
<223> OTHER INFORMATION: /mod_base="gm"
<220> FEATURE:
<221> NAME/KEY: modified_base
<222> LOCATION: (18)..(19)
<223> OTHER INFORMATION: /mod_base="OTHER" /note="2'-O-methyladenosine "
<220> FEATURE:
<221> NAME/KEY: modified_base
<222> LOCATION: (20)..(20)
<223> OTHER INFORMATION: /mod_base="gm"
<220> FEATURE:
<221> NAME/KEY: modified_base
<222> LOCATION: (21)..(22)
<223> OTHER INFORMATION: /mod_base="OTHER" /note="2'-O-methyluridine "
<220> FEATURE:
<221> NAME/KEY: modified_base
<222> LOCATION: (23)..(23)
<223> OTHER INFORMATION: /mod_base="gm"
<220> FEATURE:
<221> NAME/KEY: modified_base
<222> LOCATION: (24)..(25)
<223> OTHER INFORMATION: /mod_base="OTHER" /note="2'-O-methyluridine "
<220> FEATURE:
<221> NAME/KEY: modified_base
<222> LOCATION: (26)..(27)
<223> OTHER INFORMATION: /mod_base="gm"
<220> FEATURE:
<221> NAME/KEY: modified_base
<222> LOCATION: (28)..(28)
<223> OTHER INFORMATION: /mod_base="OTHER" /note="2'-O-methyluridine "
<220> FEATURE:
<221> NAME/KEY: modified_base
<222> LOCATION: (29)..(30)
<223> OTHER INFORMATION: /mod_base="gm"
<220> FEATURE:
<221> NAME/KEY: modified_base
<222> LOCATION: (31)..(31)
<223> OTHER INFORMATION: /mod_base="OTHER" /note="2'-O-methyluridine "
<220> FEATURE:
<221> NAME/KEY: modified_base
<222> LOCATION: (32)..(33)
<223> OTHER INFORMATION: /mod_base="gm"
<220> FEATURE:
<221> NAME/KEY: modified_base
<222> LOCATION: (34)..(34)
<223> OTHER INFORMATION: /mod_base="OTHER" /note="2'-O-methyluridine "
<220> FEATURE:
<221> NAME/KEY: modified_base
<222> LOCATION: (35)..(35)
<223> OTHER INFORMATION: /mod_base="gm"

<400> SEQUENCE: 34
gaaguuuuga gguuuugaag uuguuggugg uggug          35
```